United States Patent [19]
Nakamura et al.

[11] Patent Number: 5,653,913
[45] Date of Patent: Aug. 5, 1997

[54] MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

[75] Inventors: Shinichi Nakamura, Isehara; Takao Takiguchi, Tokyo; Takashi Iwaki, Machida; Takeshi Togano, Yokohama; Yoko Kosaka, Atsugi, all of Japan

[73] Assignee: Canon Kabushiki Kaishai, Tokyo, Japan

[21] Appl. No.: 628,446

[22] Filed: Apr. 5, 1996

Related U.S. Application Data

[63] Continuation of Ser. No. 297,840, Aug. 30, 1994, abandoned.

[30] Foreign Application Priority Data

Aug. 31, 1993 [JP] Japan ................................. 5-237215
Sep. 6, 1993 [JP] Japan ................................. 5-243580

[51] Int. Cl.$^6$ ............... C09K 19/52; C09K 19/06; C09K 19/34; C09K 19/32
[52] U.S. Cl. ............ 252/299.01; 252/299.63; 252/299.65; 252/299.66; 252/299.61; 252/299.62; 252/299.6; 252/299.67
[58] Field of Search ............ 252/299.01, 299.6, 252/299.61, 299.62, 299.63, 299.66, 299.67, 299.65

[56] References Cited

U.S. PATENT DOCUMENTS

| | | | |
|---|---|---|---|
| 4,367,924 | 1/1983 | Clark et al. ................... | 359/56 X |
| 5,075,030 | 12/1991 | Togano et al. ................ | 252/299.61 |
| 5,082,587 | 1/1992 | Janulis ......................... | 252/299.01 |
| 5,091,109 | 2/1992 | Takiguchi et al. ............ | 252/299.61 |
| 5,118,441 | 6/1992 | Mori et al. .................... | 252/299.61 |

(List continued on next page.)

FOREIGN PATENT DOCUMENTS

| | | |
|---|---|---|
| 4034123 | 4/1992 | Germany. |
| 4215277 | 11/1993 | Germany. |
| 56-107216 | 8/1981 | Japan. |
| 61-293288 | 12/1986 | Japan. |
| 62-093248 | 4/1987 | Japan. |

(List continued on next page.)

OTHER PUBLICATIONS

Fukuda et al., "Structures and Properties of Ferroelectric Liquid Crystals" (1990), Corona Publishing Co. Ltd., Tokyo, Japan,(pp. 344–349).

A. Fukuda, Future Liquid Crystal Display and its Materials (1992) K. K. CMC, Tokyo, Japan (pp. 36–51).

D. Demus, H. Zaschke; Flüssige Kristalle in Tabellen II,1984 (VEB Deutscher Verlag für Grundstoffindustrie).

A.D.L. Chandani et al. J. Journal Appl. Phys.v27(5), L729–732, May 1988.

M. Schadt & W. Helfrich, Appl. Phys. Lett.v18(4), 15 Feb.1971 pp. 127–128.

M. Schadt and W. Helfrich, Voltage–Dependent Optical Activity of a Twisted Nemantic Liquid Crystal, Feb. 1971, pp. 127 and 128, Applied Physics Letters, vol. 18, No. 4, 1971.

*Primary Examiner*—C. H. Kelly
*Attorney, Agent, or Firm*—Fitzpatrick, Cella, Harper & Scinto

[57] ABSTRACT

A mesomorphic compound of the formula (I) according to claim 1 characterized by having at least one $CF_2$ group between $CH_2$ groups in a specific alkoxy alkyl terminal group is suitable as a component for a liquid crystal composition providing improved response characteristics and a high contrast. A liquid crystal device is constituted by disposing the liquid crystal composition between a pair of substrates. The liquid crystal device is used as a display panel constituting a liquid crystal apparatus providing good display characteristics.

13 Claims, 8 Drawing Sheets

U.S. PATENT DOCUMENTS

| | | | |
|---|---|---|---|
| 5,176,845 | 1/1993 | Yamada et al. | 252/299.61 |
| 5,190,688 | 3/1993 | Sage et al. | 252/299.01 |
| 5,190,690 | 3/1993 | Takiguchi et al. | 252/299.61 |
| 5,196,140 | 3/1993 | Poetsch et al. | 252/299.6 |
| 5,198,151 | 3/1993 | Kuratate et al. | 252/299.66 |
| 5,262,082 | 11/1993 | Janulis et al. | 252/299.01 |
| 5,284,599 | 2/1994 | Iwaki et al. | 252/299.61 |
| 5,318,720 | 6/1994 | Takiguchi et al. | 252/299.61 |
| 5,356,560 | 10/1994 | Reiffenrath et al. | 252/299.61 |

FOREIGN PATENT DOCUMENTS

| | | |
|---|---|---|
| 62-198633 | 9/1987 | Japan . |
| 63-022042 | 1/1988 | Japan . |
| 63-044551 | 2/1988 | Japan . |
| 63-088161 | 4/1988 | Japan . |
| 63-122651 | 5/1988 | Japan . |
| 63-107951 | 5/1988 | Japan . |
| 63-104949 | 5/1988 | Japan . |
| 63-196571 | 8/1988 | Japan . |
| 63-196553 | 8/1988 | Japan . |
| 63-192732 | 8/1988 | Japan . |
| 63-218647 | 9/1988 | Japan . |
| 63-225337 | 9/1988 | Japan . |
| 63-216878 | 9/1988 | Japan . |
| 63-215661 | 9/1988 | Japan . |
| 63-243059 | 10/1988 | Japan . |
| 63-303951 | 12/1988 | Japan . |
| 1022990 | 1/1989 | Japan . |
| 1038077 | 2/1989 | Japan . |
| 1031740 | 2/1989 | Japan . |
| 1121244 | 5/1989 | Japan . |
| 1160986 | 6/1989 | Japan . |
| 1207280 | 8/1989 | Japan . |
| 1242543 | 9/1989 | Japan . |
| 1272571 | 10/1989 | Japan . |
| 1265052 | 10/1989 | Japan . |
| 2028158 | 1/1990 | Japan . |
| 2000227 | 1/1990 | Japan . |
| 2000127 | 1/1990 | Japan . |
| 2069467 | 3/1990 | Japan . |
| 2069440 | 3/1990 | Japan . |
| 2069427 | 3/1990 | Japan . |
| 2115145 | 4/1990 | Japan . |
| 2295943 | 12/1990 | Japan . |
| 3043488 | 2/1991 | Japan . |
| 3058980 | 3/1991 | Japan . |
| 3083971 | 4/1991 | Japan . |
| 3193774 | 8/1991 | Japan . |
| 3236353 | 10/1991 | Japan . |
| 3227980 | 10/1991 | Japan . |
| 3223232 | 10/1991 | Japan . |
| 4013797 | 1/1992 | Japan . |
| 4264052 | 9/1992 | Japan . |
| 4253789 | 9/1992 | Japan . |
| 4272989 | 9/1992 | Japan . |
| 4300871 | 10/1992 | Japan . |
| 6234749 | 8/1994 | Japan . |
| WO08441 | 11/1988 | WIPO . |
| WO11418 | 8/1991 | WIPO . |
| WO93022396 | 11/1993 | WIPO . |

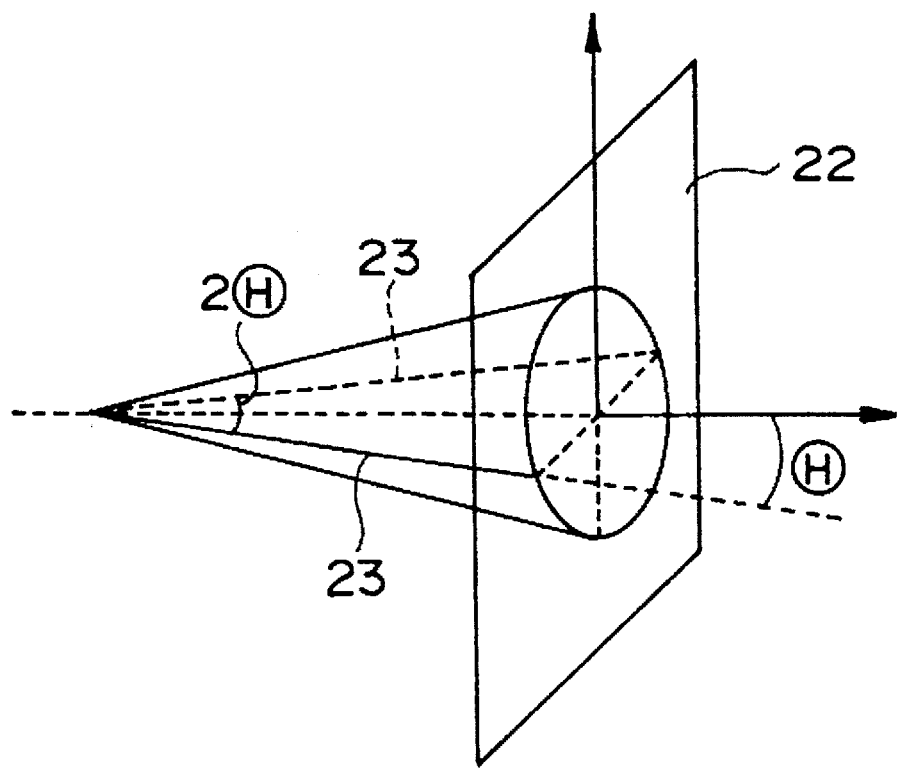
F I G. 4

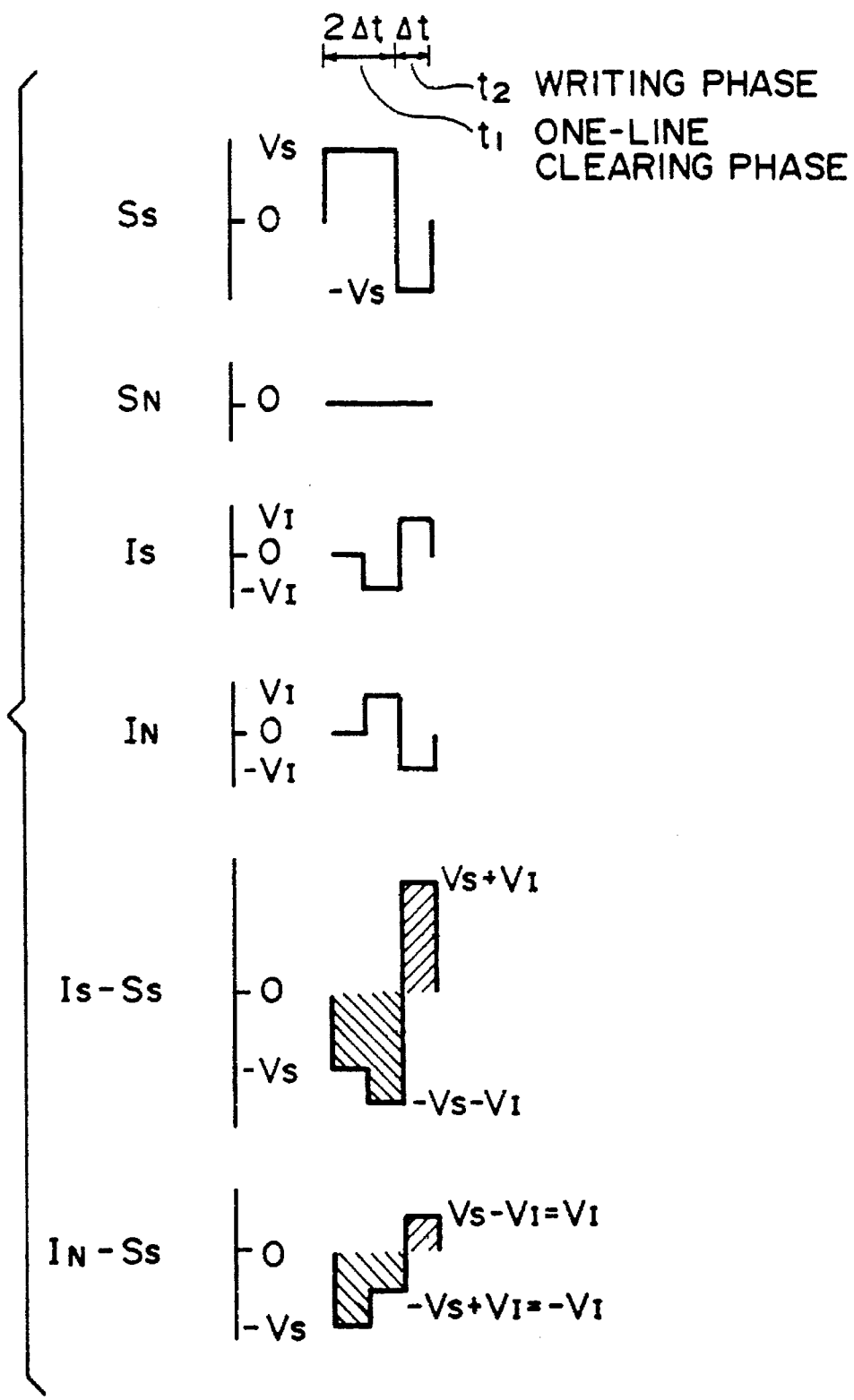
F I G. 5A

MESOMORPHIC COMPOUND, LIQUID CRYSTAL COMPOSITION CONTAINING THE COMPOUND, LIQUID CRYSTAL DEVICE USING THE COMPOSITION, LIQUID CRYSTAL APPARATUS AND DISPLAY METHOD

This application is a continuation of application No. 08/297,840, filed Aug. 30, 1994, now abandoned.

FIELD OF THE INVENTION AND RELATED ART

The present invention relates to a mesomorphic compound, a liquid crystal composition, a liquid crystal device, a display apparatus and a display method, and more particularly to a mesomorphic compound, a liquid crystal composition containing the compound with improved responsiveness to an electric field, a liquid crystal device using the composition for use in a display device, a liquid crystal-optical shutter, etc., a liquid crystal apparatus using the device particularly as a display device, and a display method of using the composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of μsec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix and for driving, a multiplex driving scheme is adapted wherein an address signal is sequentially, periodically and selectively applied to the scanning electrodes and prescribed data signals are selectively applied in parallel to the signal electrodes in with the address signal.

When the above-mentioned TN-type liquid crystal is used in device of such a driving system, a certain electric is applied to regions where a scanning electrode is selected and signal electrodes are not selected (or regions where a scanning electrode is not selected and a signal electrode is selected), which are called "half-selected points". If the difference between a voltage applied to the selected and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. have been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optic modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an field.

In to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, high contrast, etc.

More specifically, among a response time τ, the magnitude of spontaneous polarization Ps and viscosity η, the following relationship (II) exists: $\tau = \eta/(Ps \cdot E)$ ... (II), where E is an applied voltage. Accordingly, a high response speed can be obtained by (a) increasing the spontaneous polarization Ps, (b) lowering the viscosity η, or (c) increasing the applied voltage E. However, the driving voltage has a certain upper limit in view of driving with IC, etc., and should desirably be as low as possible. Accordingly, it is a actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, it is assumed that the operation temperature of an actual display device is 5°–40° C., the response speed changes by a factor of about 20, so that it actually exceeds the range controllable by driving voltage and frequency.

In general, in a liquid crystal device utilizing birefringence of a liquid crystal, the transmittance under right angle cross nicols is given by the following equation:

$$I/I_0 = \sin^2 4\theta \cdot \sin^2(\Delta nd/\lambda)\pi,$$

wherein $I_0$: incident light intensity,

I: transmitted light intensity,

θ: tilt angle,

Δn: refractive index anisotropy, d: thickness of the liquid crystal layer,

λ: wavelength of the incident light.

Tilt angle θ in a ferroelectric liquid crystal with non-helical structure is recognized as a half of an angle between the average molecular axis directions of liquid crystal molecules in a twisted alignment in a first orientation state and a second orientation state. According to the above equation, it is shown that a tilt angle θ of 22.5 degrees provides a maximum transmittance and the tilt angle θ in a non-helical structure for realizing bistability should desirably be as close as possible to 22.5 degrees in order to provide a high transmittance and a high contrast.

However, when a birefringence of a liquid crystal is utilized in a liquid crystal device using a ferroelectric liquid crystal in a non-helical structure exhibiting bistability reported by Clark and Lagerwall, the following problems are encountered, thus leading to a decrease in contrast.

First, a tile angle θ in a ferroelectric liquid crystal with non-helical structure obtained by alignment with a polyimide film treated by rubbing of the prior art has become smaller as compared with a tilt angle Ⓗ (the angle Ⓗ is a half of the apex angle of the cone shown in FIG. 4 as described below) in the ferroelectric liquid crystal having a helical structure, thus resulting in a lower transmittance.

Secondly, even if the device provides a high contrast in a static state, i.e., under no electric field application, liquid crystal molecules fluctuate due to a slight electric field at a non-selection period of time in a matrix drive scheme in the case of applying a voltage to the liquid crystal molecules for providing a display image, thus resulting in the display image including a light (or pale) black display state, i.e., a decrease in a contrast.

Thus, as described hereinabove, commercialization of a ferroelectric liquid crystal device requires a liquid crystal composition assuming a chiral smectic phase which provides a high contrast, a high-speed responsiveness and a small temperature-dependence of response speed.

In order to afford uniform switching characteristics at display, a good view-angle characteristic, a good storage stability at a low temperature, a decrease in a load to a driving IC (integrated circuit) etc. to the above-mentioned ferroelectric liquid crystal device or a display apparatus including the ferroelectric liquid crystal device, the above-mentioned liquid crystal composition is required to optimize its properties such as spontaneous polarization, an chiral smectic C (SmC*) pitch, a cholesteric (Ch) pitch, a temperature range showing a mesomorphic phase, optical anisotropy, a tilt angle and dielectric anisotropy.

SUMMARY OF THE INVENTION

An object of the present invention is to provide a mesomorphic compound providing a high speed responsiveness, a high contrast and a decreased temperature-dependence of response speed; a liquid crystal composition, particularly a chiral smectic liquid crystal composition containing the mesomorphic compound for providing a practical ferroelectric liquid crystal device as described above; a liquid crystal device including the liquid crystal composition and affording good display performances; a liquid crystal apparatus including the device; and a display method using the composition.

According to the present invention, there is provided a mesomorphic compound represented by the following formula (I):

wherein $R^1$ denotes H, halogen, CN, or a linear, branched or cyclized alkyl group having 1–30 carbon atoms capable of including at least one —$CH_2$— group which can be replaced with —O—, —S—, —CO—, —CH(Cl)—, —CH(CN)—, —$CCH_3$(CN)—, —CH=CH— or —C≡C— provided that heteroatoms are not adjacent to each other and capable of including at least one H which can be replaced with F;

m, n, p and q independently denote an integer of 1–16 provided that m+n+p+q≦19;

$Y^1$ denotes a single bond, —O—, —CO—, —COO—, —OCO—, —CH=CH— or —C≡C—; and $A^1$ denotes —$A^2$—, —$A^2$—$X^1$—$A^3$— or —$A^2$—$X^1$—$A^3$—$X^2$—$A^4$— in which $A^2$, $A^3$ and $A^4$ independently denote a divalent cyclic group selected from 1,4-phenylene capable of having one or two substituents comprising F, Cl, Br, $CH_3$, $CF_3$ or CN; pyridine-2,5-diyl; pyrimidine-2,5-diyl; pyrazine-2,5-diyl; pyridazine-3,6-diyl; 1,4-cyclohexylene; 1,3-dioxane-2,5-diyl; 1,3-dithiane-2,5-diyl; thiophene-2,5-diyl; thiazole-2,5-diyl; thiadiazole-2,5-diyl; benzoxazole-2,5-diyl; benzoxazole-2,6-diyl; benzothiazole-2,5-diyl; benzothiazole-2,6-diyl; quinoxaline-2,6-diyl; quinoline-2,6-diyl; 2,6-naphthylene; indan-2,5-diyl 2-alkylindan-2,5-diyl having a linear or branched alkyl group having 1–18 carbon atoms; indanone-2,6-diyl; 2-alkylindanone-2,6-diyl having a linear or branched alkyl group having 1–18 carbon atoms; coumaran-2,5-diyl; and 2-alkylcumaran-2,5-diyl having a linear or branched alkyl group having 1–18 carbon atoms; and $X^1$ and $X^2$ independently denote a single bond, —COO—, —OCO—, —$CH_2$O—, —O$CH_2$—, —$CH_2CH_2$—, —CH=CH— or —C≡C—.

According to the present invention, there is further provided a liquid crystal composition containing at least one species of the above-mentioned mesomorphic compound.

The present invention provides a liquid crystal device comprising a pair of electrode plates and the liquid crystal composition described above disposed between the electrode plates.

The present invention further provides a liquid crystal apparatus including the liquid crystal device, particularly including a display panel comprising the liquid crystal device.

The present invention still further provides a display method using the liquid crystal composition described above and controlling the alignment direction of liquid crystal molecules to effect display.

We have found that a mesomorphic compound, represented by the formula (I) having at least one $CF_2$ group between $CH_2$ groups in at least one terminal alkoxy alkyl group provides a wider temperature range showing a mesomorphic phase, a good compatibility with another compound and a low viscosity, and thus is suitable as a component of a liquid crystal composition, particularly a ferroelectric liquid crystal composition and a liquid crystal device including the liquid crystal composition which provide good display characteristics based on improvements in various characteristics such as an alignment characteristic, switching characteristic, responsiveness, a temperature-dependence of response speed, and a contrast. As the mesomorphic compound of the formula (I) according to the present invention has a good compatibility with another (mesomorphic or optically active) compound used herein, it is possible to use the mesomorphic compound of the formula (I) for controlling various properties such as spontaneous polarization, SmC* pitch, Ch pitch, a temperature range showing a mesomorphic phase, optical anisotropy, a tilt angle and dielectric anisotropy, with respect to a liquid crystal mixture or composition.

These and other objects, features and advantages of the present invention will become more apparent upon a consideration of the following description of the preferred embodiments of the present invention taking in conjunction with the accompanying drawings.

BRIEF DESCRIPTION OF THE DRAWINGS

FIG. 4 is a schematic view for illustrating a tilt angle ⊕ in ferroelectric liquid crystal with a helical structure.

FIG. 5A shows unit driving waveforms used in an embodiment of the present invention.

DETAILED DESCRIPTION OF THE INVENTION

Figure 1:
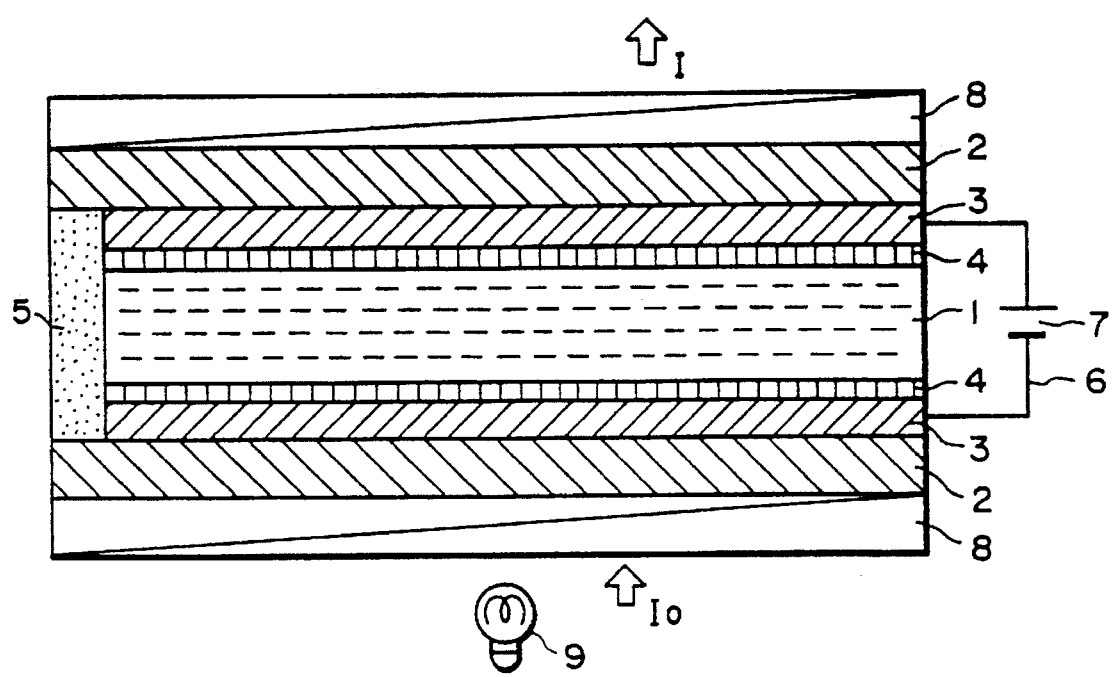
FIG. 1 is a schematic sectional view of a liquid crystal device using a liquid crystal composition assuming a chiral smectic phase.

Hereinbelow, the respective symbols m, n, p, q, $Y^1$, $A^1$, $A^2$, $A^3$, $A^4$, $X^1$, $X^2$ and $R^1$ have the meanings defined in the description with respect to the mesomorphic compound of the formula (I), unless expressly indicated otherwise.

The mesomorphic compound of the formula (I) according to the present invention is characterized by a specific alkoxy alkyl group: $C_mH_{2m+1}O(CH_2)_m(CF_2)_p(CH_2)_q$ in which at least one $CF_2$ group is disposed between $CH_2$ group.

The mesomorphic compound of the formula (I) may be an optically active compound or an optically inactive compound.

When the mesomorphic compound of the formula (I) is an optically inactive compound, $R^1$ in the formula (I) may preferably be H, halogen, CN, or a linear, branched or cyclized alkyl group having 1–20 carbon atoms capable of including at least one —$CH_2$— group which can be replaced with —O—, —S—, —CO—, —CH(CN)—, —CH=CH— or —C≡C— provided that heteroatoms are not adjacent to each other and capable of including at least H which can be replaced with F.

When the mesomorphic compound of the formula (I) is an optically active compound, $R^1$ in the formula (I) may preferably be a linear, branched or cyclized alkyl group having 2–30 carbon atoms capable of including at least one —$CH_2$— group which can be replaced with —O—, —S—, —CO—, —CH(Cl)—, —CH(CN)—, —CCH$_3$(CN)—, —CH=CH— or —C≡— provided that heteroatoms are not adjacent to each other and capable of including at least one H which can be replaced with F.

When the mesomorphic compound of the formula (I) is an optically active compound or an optically inactive compound, preferred examples of such a mesomorphic compound may include those comprising any one of the mesomorphic compounds (Ia) to (Ic) of the formula (I) below in view of control of various properties including a temperature range of a mesomorphic phase, miscibility, viscosity and alignment characteristic.

Compound (Ia) wherein $A^1$ is —$A^2$— and $A^2$ is a divalent cyclic group selected from 1,4-phenylene capable of having one or two substituents comprising F, Cl, Br, $CH_3$, $CF_3$ or CN; 1,4-cyclohexylene; quinoxaline-2,6-diyl; quinoline-2,6-diyl; and 2,6-naphthylene;

Compound (Ib) wherein $A^1$ is —$A^2$—$X^1$—$A^3$— in which at least one of $A^2$ and $A^3$ is a divalent cyclic group selected from 1,4-phenylene capable of having one or two substituents comprising F, Cl, Br, $CH_3$, $CF_3$ or CN; 1,4-cyclohexylene; pyridine-2,5-diyl; and pyrimidine-2,5-diyl; and Compound (Ic) wherein $A^1$ is —$A^2$—$X^1$—$A^3$—$X^2$—$A^4$— in which at least one of $A^2$, $A^3$ and $A^4$ is 1,4-phenylene capable of having one or two substituents comprising F, Cl, Br, $CH_3$, $CF_3$ or CN and the remainder of $A^2$, $A^3$ and $A^4$ is a divalent group selected from 1,4-phenylene capable of having one or two substituents comprising F, Cl, Br, $CH_3$, $CF_3$ or CN; pyridine-2,5-diyl; pyrimidine-2,5-diyl; 1,4-cyclohexylene; thiazole-2,5-diyl; thiadiazole-2,5-diyl; indan-2,5-diyl; and coumaran-2,5-diyl.

Further preferred examples of the mesomorphic compound of the formula (I) which is optically active or optically inactive (not optically active) may include those comprising any one of the following mesomorphic compound: (Iba) to (Ice) of the formula (I):

Compounds (Iba) wherein $A^1$ is —$A^2$—$X^1$—$A^3$— in which each of $A^2$ and $A^3$ is 1,4-phenylene capable of having one or two substituents comprising F, Cl, Br, $CH_3$, $CF_3$ or CN; and $X^1$ is a single bond, —COO—, —$CH_2$O—, —$CH_2CH_2$— or —C≡C—;

Compound (Ibb) wherein $A^1$ is —$A^2$—$X^1$—$A^3$— in which one of the groups $A^2$ and $A^3$ is 1,4-phenylene capable of having one or two substituents comprising F, Cl, Br, $CH_3$, $CF_3$ or CN; the other group $A^2$ or $A^3$ is a divalent cyclic group selected from pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiadiazole-2,5-diyl, benzoxazole-2,5-diyl, benzothiazole-2,6-diyl, quinoxaline-2,6-diyl, quinoline-2,6-diyl, 2,6-naphthylene, indan-2,5-diyl and coumaran-2,5-diyl; and $X^1$ is a single bond;

Compound (Ibc) wherein $A^1$ is —$A^2$—$X^1$—$A^3$— in which one of the groups $A^2$ and $A^3$ is pyridine-2,5-diyl; the other group $A^2$ or $A^3$ is a divalent cyclic group selected from 1,4-cyclohexylene, 2,6-naphthylene, indan-2,5-diyl and coumaran-2,5-diyl; and $X^1$ is a single bond;

Compound (Ibd) wherein $A^1$ is —$A^2$—$X^1$—$A^3$— in which one of the groups $A^2$ and $A^3$ is pyrimidine-2,5-diyl; the other group $A^2$ or $A^3$ is a divalent cyclic group selected from 1,4-cyclohexylene, 2,6-naphthylene, indan-2,5-diyl and coumaran-2,5-diyl; and $X^1$ is a single bond;

Compound (Ica) wherein $A^1$ is —$A^2$—$X^1$—$A^3$—$X^2$—$A^4$— in which each of $A^2$, $A^3$ and $A^4$ is 1,4-phenylene capable of having one or two substituents comprising F, Cl, Br, $CH_3$, $CF_3$ or CH; and at least one of $X^1$ and $X^2$ is a single bond;

Compound (Icb) wherein $A^1$ is —$A^2$—$X^1$—$A^3$—$X^2$—$A^4$— in which two of $A^2$, $A^3$ and $A^4$ is 1,4-phenylene capable of having one or two substituents comprising F, Cl, Br, $CH_3$, $CF_3$ or CN; and the remainder of $A^2$, $A^3$ and $A^4$ is a divalent cyclic group selected from pyridine-2,5-diyl, pyrimidine-2,5-diyl, 1,4-cyclohexylene, thiazole-2,5-diyl, thiadiazole-2,5-diyl, indan-2,5-diyl and coumaran-2,5-diyl; and $X^1$ and $X^2$ are a single bond;

Compound (Icc) wherein $A^1$ is —$A^2$—$X^1$—$A^3$—$X^2$—$A^4$— in which one of the groups $A^2$ and $A^4$ is pyridine-2,5-diyl and the other group $A^2$ or $A^4$ is a divalent cyclic group selected from 1,4-phenylene capable of having one or two substituents comprising F, Cl, Br, $CH_3$, $CF_3$ or CN, 1,4-cyclohexylene, thiophene-2,5-diyl, and indan-2,5-diyl; $A^3$ is 1,4-phenylene capable of having one or two substituents comprising F, Cl, Br, $CH_3$, $CF_3$ or CN; and one of the groups $X^1$ and $X^2$ is a single bond and the other group $X^1$ or $X^2$ is —OCO—, —$OCH_2$— or —$CH_2CH_2$—;

Compound (Icd) wherein $A^1$ is —$A^2$—$X^1$—$A^3$—$X^2$—$A^4$— in which one of the groups $A^2$ and $A^4$ is pyrimidine-2,5-diyl and the other group $A^2$ or $A^4$ is a divalent cyclic group selected from 1,4-phenylene capable of having one or two substituents comprising F, Cl, Br, $CH_3$, $CF_3$ or CN, 1,4-cyclohexylene, thiophene-2,5-diyl, and indan-2,5-diyl; $A^3$ is 1,4-phenylene capable of having one or two substituents comprising F, Cl, Br, $CH_3$, $CF_3$ or CN; and one of the groups $X^1$ and $X^2$ is a single bond and the other group $X^1$ or $X^2$ is —OCO—, —$OCH_2$— or —$CH_2CH_2$—; and Compound (Ice) wherein $A^1$ is —$A^2$—$X^1$—$A^3$—$X^2$—$A^4$— in which one of the groups $A^2$ and $A^4$ is 1,4-cyclohexylene and the other group $A^2$ or $A^4$ is a divalent cyclic group selected from 1,4-phenylene capable of having one or two substituents comprising F, Cl, Br, $CH_3$, $CF_3$ or CN, 1,4-cyclohexylene, thiophene-2,5-diyl, and indan-2,5-diyl; $A^3$ is 1,4-phenylene capable of having one or two substituents comprising F, Cl, Br, $CH_3$, $CF_3$ or CN; and one of the groups $X^1$ and $X^2$ is a single bond and the other group $X^1$ and $X^2$ is —OCO—, —$OCH_2$— or —$CH_2CH_2$—.

When the mesomorphic compound of the formula (I) is an optically inactive compound, such a compound may, in particular, preferably be any one of the the formula (I):

Compounds (Ibaa) wherein $A^1$ is —$A^2$—$X^1$—$A^3$— in which each of $A^2$ and $A^3$ is 1,4-phenylene capable of having one or two substituents comprising F, Cl, Br, $CH_3$, $CF_3$ or CN; and $X^1$ is a single bond, —COO—, —$CH_2O$—, —$CH_2CH_2$— or —C≡C—;

Compound (Ibba) wherein $A^1$ is —$A^2$—$A^1$—$A^3$— in which $A^2$ is 1,4-phenylene capable of having one or two substituents comprising F, Cl, Br, $CH_3$, $CF_3$ or CN; $A^3$ is a divalent cyclic group selected from pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiadiazole-2,5-diyl, benzoxazole-2,5-diyl, benzothiazole-2,6-diyl, quinoxaline-2,6-diyl, quinoline-2,6-diyl, 2,6-naphthylene, indan-2,5-diyl and coumaran-2,5-diyl; and $X^1$ is a single bond;

Compound (Ibca) wherein $A^1$ is —$A^2$—$X^1$—$A^3$— in which $A^2$ is pyridine-2,5-diyl; $A^3$ is a divalent cyclic group selected from 1,4-cyclohexylene, 2,6-naphthylene, indan-2,5-diyl and coumaran-2,5-diyl; and $X^1$ is a single bond;

Compound (Ibda) wherein $A^1$ is —$A^2$—$X^1$—$A^3$— in which $A^2$ is pyrimidine-2,5-diyl; $A^3$ is a divalent cyclic group selected from 1,4-cyclohexylene, 2,6-naphthylene, indan-2,5-diyl and coumaran-2,5-diyl; and $X^1$ is a single bond;

Compound (Icaa) wherein $A^1$ is —$A^2$—$X^1$—$A^3$—$X^2$—$A^4$— in which each of $A^2$, $A^3$ and $A^4$ is 1,4-phenylene capable of having or two substituents comprising F, Cl, Br, $CH_3$, $CF_3$ or CN; and at least one of $X^1$ and $X^2$ is a single bond;

Compound (Icba) wherein $A^1$ is —$A^2$—$X^1$—$A^3$—$X^2$—$A^4$— in which two of $A^2$, $A^3$ and $A^4$ is 1,4-phenylene capable of having one or two substituents comprising F, Cl, Br, $CH_3$, $CF_3$ or CN; and the remainder of $A^2$, $A^3$ and $A^4$ is a divalent cyclic group selected from pyridine-2,5-diyl, pyrimidine-2,5-diyl, 1,4-cyclohexylene, thiazole-2,5-diyl, thiadiazole-2,5-diyl, indan-2,5-diyl and coumaran-2,5-diyl; and $X^1$ and $X^2$ are a single bond;

Compound (Icca) wherein $A^1$ is —$A^2$—$X^1$—$A^3$—$X^2$—$A^4$— in which $A^2$ is pyridine-2,5-diyl; $A^4$ is a divalent cyclic group selected from 1,4-phenylene capable of having one or two substituents comprising F, Cl, Br, $CH_3$, $CF_3$ or CN, 1,4-cyclohexylene, thiophene-2,5-diyl, and indan-2,5-diyl; $A^3$ is 1,4-phenylene capable of having one or two substituents comprising F, Cl, Br, $CH_3$, $CF_3$ or CN; $X^1$ is a single bond; and $X^2$ is —OCO—, —$OCH_2$— or —$CH_2CH_2$—;

Compound (Icda) wherein $A^1$ is —$A^2$—$X^1$—$A^3$—$X^2$—$A^4$— in which $A^2$ is pyrimidine-2,5-diyl; $A^4$ is a divalent cyclic group selected from 1,4-phenylene capable of having one or two substituents comprising F, Cl, Br, $CH_3$, $CF_3$ or CN, 1,4-cyclohexylene, thiophene-2,5-diyl, and indan-2,5-diyl; $A^3$ is 1,4-phenylene capable of having one or two substituents comprising F, Cl, Br, $CH_3$, $CF_3$ or CN; $X^1$ is a single bond; and $X^2$ is —OCO—, —$OCH_2$— or —$CH_2CH_2$—; and Compound (Icea) wherein $A^1$ is —$A^2$—$X^1$—$A^3$—$X^2$—$A^4$— in which $A^2$ is 1,4-cyclohexylene; $A^4$ is a divalent cyclic group selected from 1,4-phenylene capable of having one or two substituents comprising F, Cl, Br, $CH_3$, $CF_3$ or CN, 1,4-cyclohexylene, thiophene-2,5-diyl, and indan-2,5-diyl; $A^3$ is 1,4-phenylene capable of having one or two substituents comprising F, Cl, Br, $CH_3$, $CF_3$ or CN; $X^1$ is a single bond; and $X^2$ is —OCO—, —$OCH_2$— or —$CH_2CH_2$—.

When the mesomorphic compound of the formula (I) is optically active or not optically active, at least one of $A^2$ and $A^3$ may preferably be a divalent cyclic group selected from thiophene-2,5-diyl; thiazole-2,5-diyl; thiadiazole-2,5-diyl; benzoxazole-2,5-diyl; benzoxazole-2,6-diyl; benzothiazole-2,5-diyl; benzothiazole-2,6-diyl; quinoxaline-2,6-diyl; quinoline--2,6-diyl; indan-2,5-diyl; 2-alkylindanone-2,5-diyl having a linear or branched alkyl group having 1–18 carbon atoms; indanone-2,6-diyl; 2-alkylindanone-2,6-diyl having a linear or branched alkyl group having 1–18 carbon atoms; coumaran-2,5-diyl; and 2-alkylcumaran-2,5-diyl having a linear or branched alkyl group having 1–18 carbon atoms.

When the mesomorphic compound of the formula (I) is an optically inactive compound, $R^1$ in the formula (I) may preferably be any one of the following groups (1-i) to (1-vii):

$$C_mH_{2m+1}O(CH_2)_n(CF_2)_p(CH_2)_q-Y^1-, \qquad (1\text{-i})$$

$$n\text{-}C_aH_{2a+1}-Y^1-, \qquad (1\text{-ii})$$

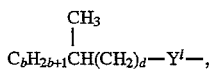  (1-iii)

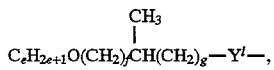  (1-iv)

$$C_hF_{2h+1}(CH_2)_i-Y^1-, \qquad (1\text{-v})$$

F, and  (1-vi)

H,  (1-vii)

in which a is an integer of 1–16; m is an integer of 1–13; n and q each are an integer of 1–5; d, g and i each are an integer of 0–7; p, b, e and h each are an integer of 1–10; f is 0 or 1 with the proviso that m+n+p+q≦16, b+d≦16, e+f+g≦16, and h+i≦16, and $Y^1$ is a single bond, —O—, —COO— or —OCO—.

When the mesomorphic compound of the formula (I) is an optically active compound, $R^1$ in the formula (I) may preferably be any one of the following optically active groups (2-i) to (2-x):

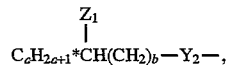  (2-i)

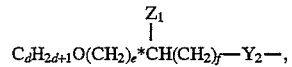  (2-ii)

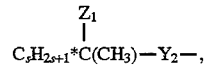  (2-iii)

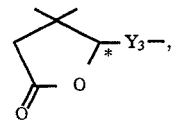  (2-iv)

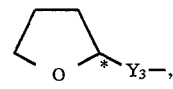  (2-v)

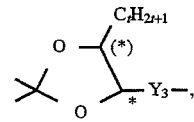  (2-vi)

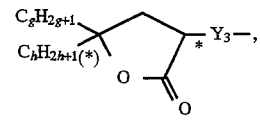  (2-vii)

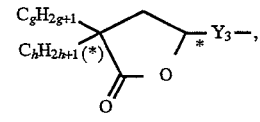  (2-viii)

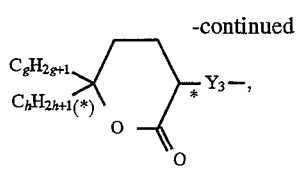  (2-ix)

and

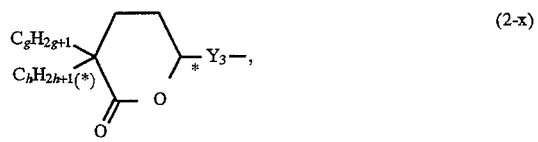  (2-x)

in which a, s and d each are an integer of 1–16; b, g, h and t each are an integer of 0–10; e is an integer of 0–3; f is an integer of 0–7 with the proviso that a+b≦16 and d+e+f≦15, $Z_1$ is $CH_3$, $CF_3$, F or CN; $Y_2$ is a single bond, —O—, —COO— or —OCO—; $Y_3$ is a single bond, —O—, —COO—, —OCO—, —$CH_2$O— or —$CH_2$OCO—; and * denotes the location of an optically active center.

$R^1$ may be a cyclized alkyl group (e.g., the groups (2-iv) to (2-x) as described above. Herein, "cyclized alkyl group" means a cyclic alkyl group or an alkyl group having a partially cyclized structure in which the cyclized structure can be constituted by methylene group and/or at least one heteroatom (e.g., oxygen) and at least one methylene group in the alkyl group can be replaced with —O— or —CO—.

The mesomorphic compound of the formula (I) (optically active or optically inactive) may generally be synthesized through, e.g., the following reaction schemes.

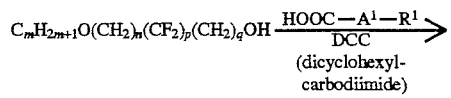
(dicyclohexyl-
carbodiimide)

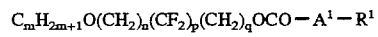

Herein, the term "mesomorphic compound" covers not only a compound assuming a mesomorphic (liquid crystal) phase but also a compound not assumes a mesomorphic phase per se as long as a liquid crystal composition containing such a compound assumes a mesomorphic phase.

Specific examples of the optically inactive mesomorphic compound of the formula (I) may include those represented by the following structural formulae 1-1 to 1-232 including abbreviations for respective cyclic groups listed below.

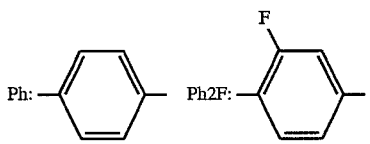

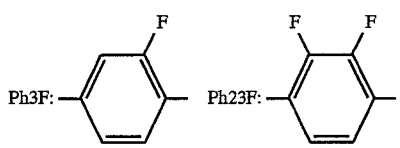

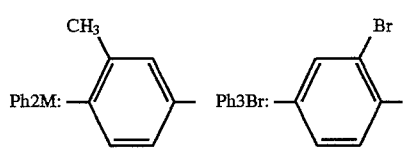

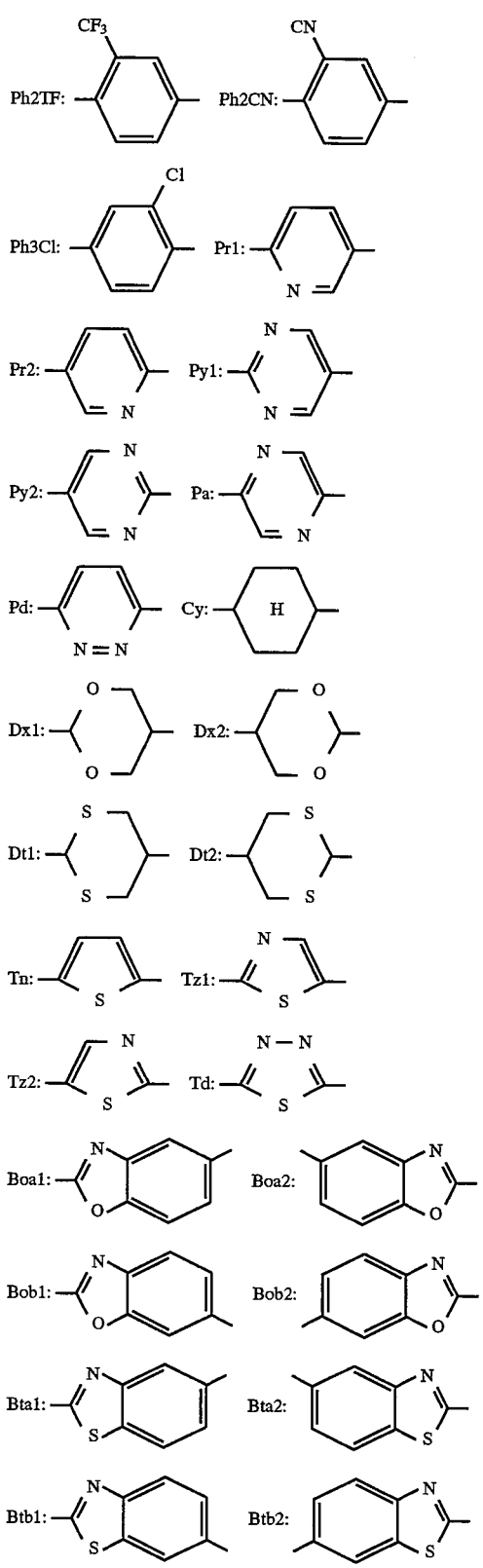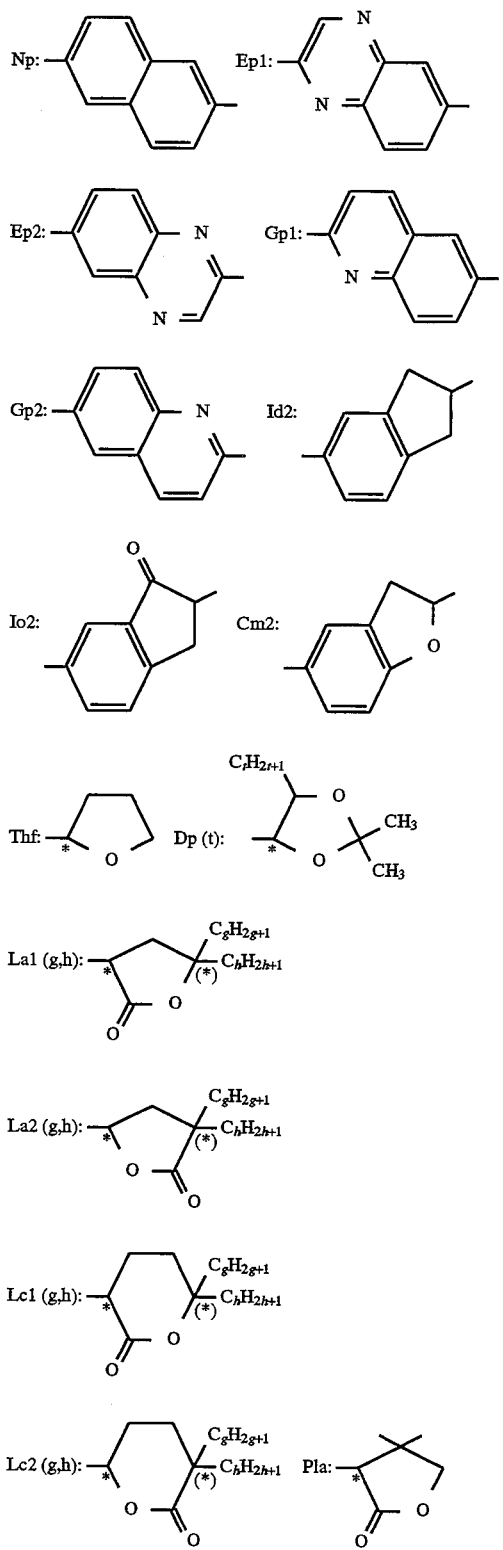
In the above t, g and h each are an integer of 0–10.

| Ex. Comp. No. | $C_mH_{2m+1}O(CH_2)_n(CF_2)_p(CH_2)_q-Y^1$ | | | | | $A^1$ | | | | | $R^1$ |
|---|---|---|---|---|---|---|---|---|---|---|---|
| | m | n | p | q | —$Y^1$— | $A^2$ | $X^1$ | $A^3$ | $X^2$ | $A^4$ | |
| 1-1 | 1 | 4 | 1 | 4 | —O— | Ph | — | Ph | — | — | $OC_6H_{13}$ |
| 1-2 | 2 | 1 | 1 | 1 | —O— | Py2 | — | Ph | — | — | $C_5H_{11}$ |
| 1-3 | 2 | 2 | 1 | 2 | —O— | Ph | — | Py1 | — | — | $C_7H_{15}$ |
| 1-4 | 3 | 7 | 1 | 7 | —O— | Ep2 | — | Ph | — | — | $C_8H_{17}$ |
| 1-5 | 3 | 4 | 1 | 4 | —O— | Py2 | — | Ph | —OCO— | Ph | $C_{10}H_{21}$ |
| 1-6 | 4 | 1 | 1 | 1 | —O— | Ph | — | BtB1 | — | — | $C_{13}H_{27}$ |
| 1-7 | 4 | 1 | 1 | 1 | —O— | Ph | —COO— | Ph2F | — | — | $C_7H_{15}$ |
| 1-8 | 4 | 2 | 1 | 2 | —O— | Ph | — | Py1 | — | — | $C_6H_{13}$ |
| 1-9 | 5 | 1 | 1 | 1 | — | Ph | —COO— | Ph | — | — | $OCOC_9H_{19}$ |
| 1-10 | 5 | 1 | 1 | 1 | —O— | Ph | — | Ph | — | Py1 | $C_{12}H_{25}$ |
| 1-11 | 5 | 1 | 1 | 8 | —O— | Ph | — | Py1 | — | — | $OC_6H_{13}$ |
| 1-12 | 6 | 1 | 1 | 1 | —O— | Ph | — | Cy | — | — | $C_8H_{17}$ |
| 1-13 | 6 | 3 | 1 | 3 | —O— | Ph | — | Py2 | — | — | $C_4H_9$ |
| 1-14 | 6 | 2 | 1 | 2 | —COO— | Ph | —OCO— | Ph | — | — | $OCH_2CH(CH_3)C_2H_5$ |
| 1-15 | 7 | 2 | 1 | 2 | — | Ph | — | Py1 | — | — | $C_{11}H_{23}$ |
| 1-16 | 4 | 1 | 3 | 1 | —O— | Ph | — | Ep1 | — | — | $C_8H_{17}$ |
| 1-17 | 8 | 1 | 1 | 1 | —O— | Py2 | — | Ph | $CH_2CH_2$ | Tn | $C_7H_{15}$ |
| 1-18 | 8 | 2 | 1 | 2 | —O— | Ph | CH=CH | Ph | — | — | $C_6H_{13}$ |
| 1-19 | 9 | 1 | 1 | 1 | —O— | Ph | — | Boa1 | — | — | $C_3H_7$ |
| 1-20 | 10 | 1 | 1 | 1 | —O— | Ph | — | Bta1 | — | — | $C_{15}H_{31}$ |
| 1-21 | 11 | 1 | 1 | 1 | —O— | Py2 | — | Cm2 | — | — | $C_6H_{13}$ |
| 1-22 | 12 | 2 | 1 | 2 | — | Ph | — | Ph | — | Pr1 | $C_9H_{19}$ |
| 1-23 | 13 | 2 | 1 | 2 | —O— | Ph | —$OCH_2$— | Ph | — | — | $OC_6H_{11}$ |
| 1-24 | 14 | 1 | 1 | 1 | —O— | Ph | — | Py1 | — | Ph | $C_6H_{13}$ |
| 1-25 | 15 | 1 | 1 | 1 | —O— | Ph | — | — | — | — | $OC_8H_{17}$ |
| 1-26 | 16 | 1 | 1 | 1 | —O— | Ph | — | Gp1 | — | — | $C_{10}H_{21}$ |
| 1-27 | 1 | 1 | 2 | 1 | —O— | Ph | — | Pr1 | — | — | $C_{11}H_{23}$ |
| 1-28 | 1 | 2 | 2 | 2 | —O— | Py2 | — | Ph | —OCO— | Cy | $C_6H_{13}$ |
| 1-29 | 2 | 1 | 2 | 1 | —OCO— | Ph | — | Py1 | — | — | $OCH_2C_6F_{13}$ |
| 1-30 | 2 | 1 | 2 | 1 | —O— | Py2 | — | Cy | — | — | $C_{10}H_{21}$ |
| 1-31 | 2 | 2 | 2 | 2 | —O— | Ph | $CH_2CH_2$ | Ph | — | — | $OCH_2C_6H_{13}$ |
| 1-32 | 2 | 6 | 2 | 6 | —O— | Ph | — | Ph3F | — | — | $C_6H_{13}$ |
| 1-33 | 3 | 1 | 2 | 1 | — | Ph | — | Py2 | — | — | $C_8H_{17}$ |
| 1-34 | 3 | 1 | 2 | 1 | —O— | Pr2 | — | Ph | —OCO— | Ph | $C_6H_{13}$ |
| 1-35 | 3 | 1 | 2 | 1 | —O— | Ph | — | Ph | — | — | $C_{16}H_{33}$ |
| 1-36 | 3 | 2 | 2 | 2 | —O— | Ph | — | Py1 | — | — | $C_{13}H_{27}$ |
| 1-37 | 4 | 1 | 2 | 1 | —O— | Ph | — | Py1 | — | — | $OC_5H_{11}$ |
| 1-38 | 4 | 1 | 2 | 1 | —OCO— | Ph | — | Ep2 | — | — | $C_6H_{13}$ |
| 1-39 | 4 | 1 | 2 | 1 | —O— | Ph | —COO— | Ph | — | Tn | $C_4H_9$ |
| 1-40 | 4 | 2 | 2 | 2 | — | Ph | —$CH_4O$— | Ph | — | — | $OCH(CH_3)CH_2OC_3H_7$ |
| 1-41 | 4 | 3 | 2 | 5 | —O— | Ph | — | Py1 | — | — | $C_{10}H_{21}$ |
| 1-42 | 5 | 1 | 2 | 1 | —O— | Ph | — | Py1 | — | — | $C_{10}F_{21}$ |
| 1-43 | 5 | 1 | 2 | 1 | —O— | Ph | — | Tz1 | — | Ph | $C_6H_{13}$ |
| 1-44 | 5 | 2 | 2 | 2 | — | Ph | —COO— | Ph | — | — | $OC_8H_{17}$ |
| 1-45 | 5 | 3 | 2 | 4 | —O— | Ph | — | Ph | — | Py1 | $C_6H_{13}$ |
| 1-46 | 6 | 1 | 2 | 1 | —O— | Py2 | — | Ph | $CH_2CH_2$ | Cy | $C_7H_{15}$ |
| 1-47 | 6 | 1 | 2 | 1 | —O— | Ph | — | Pd | — | — | $C_6H_{13}$ |
| 1-48 | 6 | 1 | 2 | 1 | —O— | Py2 | — | Cm2 | — | — | $C_{10}H_{21}$ |
| 1-49 | 6 | 1 | 2 | 1 | —OCO— | Ph | —C≡C— | Ph | — | — | $OC_{11}H_{13}$ |
| 1-50 | 7 | 1 | 2 | 1 | —O— | Ph | — | Ep1 | — | — | $C_{10}H_{21}$ |
| 1-51 | 7 | 2 | 2 | 2 | —C≡C— | Ph | — | Py1 | — | — | $C_5H_{11}$ |
| 1-52 | 7 | 1 | 2 | 1 | —O— | Ph | — | Cy | — | — | $C_9H_{19}$ |
| 1-53 | 8 | 1 | 2 | 5 | —O— | Ph | — | Ph | —OCO— | Ph2TF | $C_4H_9$ |
| 1-54 | 8 | 1 | 2 | 1 | —O— | Ph | — | Py1 | — | — | $C_{12}H_{25}$ |
| 1-55 | 9 | 2 | 2 | 2 | — | Ph | —OCO— | Ph | — | — | $C_2H_6$ |
| 1-56 | 9 | 1 | 2 | 1 | —O— | Ep2 | — | — | — | — | $OCOC_6H_{13}$ |
| 1-57 | 10 | 1 | 2 | 1 | —O— | Ph | — | Ph | — | Cy | $C_6H_{17}$ |
| 1-58 | 11 | 1 | 2 | 1 | —O— | Ph | — | Py2 | — | Ph | $C_6H_{13}$ |
| 1-59 | 12 | 2 | 2 | 1 | —O— | Ph | — | Np | — | — | $C_7H_{15}$ |
| 1-60 | 14 | 1 | 2 | 1 | —O— | Pr2 | — | Ph | —OCO— | Cy | $C_5H_{11}$ |
| 1-61 | 1 | 6 | 3 | 3 | —O— | Ph | — | Pr1 | — | — | $OC_{11}H_{23}$ |
| 1-62 | 1 | 11 | 3 | 1 | —O— | Ph | —COO— | Ph | — | Ph | $C_{12}H_{25}$ |
| 1-63 | 2 | 1 | 3 | 1 | —O— | Py2 | — | Ph | —OCO— | Tn | $C_3H_7$ |
| 1-64 | 2 | 1 | 3 | 1 | —$OCH_2$— | Ph | —COO— | Ph | — | — | $C_6H_{13}$ |
| 1-65 | 2 | 3 | 3 | 3 | —O— | Ph | — | Tz2 | — | Ph | $C_8H_{17}$ |
| 1-66 | 3 | 1 | 3 | 1 | —O— | Ph | — | Py1 | — | — | $C_8H_{17}$ |
| 1-67 | 3 | 1 | 3 | 1 | —O— | Ph | — | Py1 | — | — | $C_{18}H_{37}$ |
| 1-68 | 3 | 1 | 3 | 1 | —CH=CH— | Ph | — | Ph | — | — | $C_6H_{13}$ |
| 1-69 | 3 | 1 | 3 | 1 | —O— | Py2 | — | Ph | — | — | $C_{10}H_{21}$ |
| 1-70 | 4 | 1 | 3 | 1 | —OCO— | Ph | — | Py1 | — | — | $C_9H_{19}$ |
| 1-71 | 4 | 1 | 3 | 1 | —OCO— | Ph | — | Ph | — | — | $OC_5H_{11}$ |
| 1-72 | 4 | 3 | 3 | 3 | —O— | Pr2 | — | Cy | — | — | $C_{10}H_{21}$ |
| 1-73 | 5 | 1 | 3 | 1 | —O— | Ph | —$OCH_2$— | Ph | — | — | $C_{12}H_{25}$ |
| 1-74 | 5 | 1 | 3 | 1 | —O— | Ph | — | Ep1 | — | — | $C_6H_{13}$ |
| 1-75 | 5 | 1 | 3 | 1 | —$OCH_2$— | Ph | — | Pr1 | — | — | $C_8H_{17}$ |

-continued

| Ex. Comp. | $C_mH_{2m+1}O(CH_2)_n(CF_2)_p(CH_2)_q$—$Y^1$ | | | | | $A^1$ | | | | | $R^1$ |
|---|---|---|---|---|---|---|---|---|---|---|---|
| No. | m | n | p | q | —$Y^1$— | $A^2$ | $X^1$ | $A^3$ | $X^2$ | $A^4$ | $R^1$ |
| 1-76 | 6 | 1 | 3 | 1 | —O— | Ph | — | Ph | — | Ph | $C_5H_{11}$ |
| 1-77 | 6 | 1 | 3 | 1 | —O— | Ph | —OCO— | Ph | — | — | $O(CH_2)_5CH(CH_3)CH_3$ |
| 1-78 | 7 | 1 | 3 | 1 | —O— | Py2 | — | Boa2 | — | Ph | $C_9H_{19}$ |
| 1-79 | 7 | 2 | 3 | 2 | —O— | Ph | — | Py2 | — | — | $C_6H_{13}$ |
| 1-80 | 7 | 1 | 3 | 1 | —O— | Pr2 | — | Ph | —OCO— | Tn | $C_4H_9$ |
| 1-81 | 8 | 1 | 3 | 1 | —O— | Ph | $CH_2CH_2$ | Ph | — | — | $C_9H_{19}$ |
| 1-82 | 8 | 1 | 3 | 5 | —O— | Ph | — | Py1 | — | — | $C_6H_{13}$ |
| 1-83 | 8 | 1 | 3 | 1 | —O— | Cy | — | Ph | —OCH$_2$— | Ph | $C_7H_{15}$ |
| 1-84 | 9 | 1 | 3 | 1 | —O— | Ph | — | Ph | — | — | $COOC_4H_9$ |
| 1-85 | 9 | 1 | 3 | 1 | —O— | Ph | — | Ph23F | — | — | $C_6H_{13}$ |
| 1-86 | 10 | 1 | 3 | 1 | —O— | Ph | — | Td | — | Ph | $C_8H_{17}$ |
| 1-87 | 11 | 1 | 3 | 1 | —O— | Py2 | — | Ph | $CH_2CH_2$ | Ph | $C_{10}H_{21}$ |
| 1-88 | 13 | 1 | 3 | 1 | — | Py2 | — | Btb2 | — | Ph | $C_5H_{11}$ |
| 1-89 | 14 | 1 | 3 | 1 | —O— | Py2 | — | Ph3F | — | — | $C_6H_{13}$ |
| 1-90 | 1 | 2 | 4 | 2 | —O— | Ph | —CH$_2$O— | Ph | — | — | $C_3H_7$ |
| 1-91 | 1 | 4 | 4 | 4 | —O— | Ph | — | Id2 | — | — | $C_8H_{17}$ |
| 1-92 | 2 | 1 | 4 | 1 | —O— | Cy | — | Ph | —OCO— | Id2 | $C_5H_{11}$ |
| 1-93 | 2 | 1 | 4 | 1 | —O— | Ph | — | Gp1 | — | — | $C_{11}H_{23}$ |
| 1-94 | 2 | 3 | 4 | 3 | —O— | Ph | — | Py1 | — | — | $C_7H_{15}$ |
| 1-95 | 3 | 1 | 4 | 1 | —OCO— | Ph | — | Btb1 | — | — | $C_6H_{13}$ |
| 1-96 | 3 | 1 | 4 | 1 | — | Ph | —COO— | Ph | — | — | $OCH_2C_8H_{17}$ |
| 1-97 | 3 | 1 | 4 | 1 | —O— | Py2 | — | Np | — | — | $OCH_2C_{10}F_{21}$ |
| 1-98 | 3 | 2 | 4 | 2 | —O— | Ph | — | Dx2 | — | Ph | $C_6H_{13}$ |
| 1-99 | 4 | 1 | 4 | 1 | —O— | Ph | — | Tz1 | — | Ph | $C_6H_{13}$ |
| 1-100 | 4 | 1 | 4 | 1 | —O— | Gp2 | — | — | — | — | $C_6H_{13}$ |
| 1-101 | 4 | 1 | 4 | 1 | —O— | Ph | — | Ph | — | — | $C_{14}H_{29}$ |
| 1-102 | 4 | 1 | 4 | 1 | —O— | Ph | — | Dt1 | — | Ph | $C_{10}H_{21}$ |
| 1-103 | 4 | 2 | 4 | 2 | —OCO— | Ph | — | Pa | — | — | $C_9H_{19}$ |
| 1-104 | 5 | 1 | 4 | 1 | —O— | Py2 | — | Io2 | — | — | $C_8H_{17}$ |
| 1-105 | 5 | 1 | 4 | 1 | —O— | Ph | — | Ph | — | Cy | $C_6H_{13}$ |
| 1-106 | 5 | 2 | 4 | 2 | —O— | Ph | — | Py1 | — | — | $C_6H_{13}$ |
| 1-107 | 5 | 1 | 4 | 1 | —O— | Ph | — | Ph | — | Py1 | $C_5H_{11}$ |
| 1-108 | 6 | 2 | 4 | 1 | —O— | Py2 | — | Ph | — | — | $C_9H_{19}$ |
| 1-109 | 6 | 1 | 4 | 1 | —O— | Ph2F | — | Ph | — | Py1 | $C_8H_{17}$ |
| 1-110 | 6 | 1 | 4 | 1 | —O— | Ph | —C≡C— | Ph | — | — | $C_{10}H_{21}$ |
| 1-111 | 7 | 1 | 4 | 1 | — | Ph | — | Np | — | — | $OC_4H_{19}$ |
| 1-112 | 7 | 1 | 4 | 2 | —O— | Ph | — | Ph | — | Ph | $C_6H_{13}$ |
| 1-113 | 8 | 1 | 4 | 1 | —O— | Py2 | — | Ph | —OCH$_2$— | Id2 | $C_9H_{19}$ |
| 1-114 | 8 | 1 | 4 | 1 | —O— | Ph | —OCH$_2$— | Ph | — | — | $C_{10}H_{21}$ |
| 1-115 | 8 | 1 | 4 | 1 | —O— | Py2 | — | Ph | —OCO— | Id2 | $C_6H_{13}$ |
| 1-116 | 9 | 1 | 4 | 1 | —OCH$_2$— | Ph | — | Dt2 | — | — | $C_5H_{11}$ |
| 1-117 | 9 | 1 | 4 | 3 | —O— | Ph | — | Tz1 | — | Ph | $C_5H_{11}$ |
| 1-118 | 4 | 1 | 3 | 1 | —O— | Ph | — | Pr1 | — | — | $C_{10}H_{21}$ |
| 1-119 | 10 | 1 | 4 | 1 | —O— | Ph | — | Py1 | — | Ph | $OC_9H_{19}$ |
| 1-120 | 12 | 1 | 4 | 1 | —O— | Cy | — | Ph | $CH_2CH_2$ | Tn | $C_3H_7$ |
| 1-121 | 1 | 1 | 5 | 1 | —O— | Ph | — | Tn | — | — | $C_{11}H_{23}$ |
| 1-122 | 1 | 3 | 5 | 3 | —O— | Ph | —COO— | Ph | —COO— | Ph | $C_8H_{17}$ |
| 1-123 | 2 | 1 | 5 | 1 | —O— | Ph | — | Py1 | — | — | $C_6H_{13}$ |
| 1-124 | 2 | 1 | 5 | 1 | —O— | Ph | — | Ph | —CH$_2$O— | Ph | $C_7H_{15}$ |
| 1-125 | 2 | 3 | 5 | 1 | —O— | Ph | — | Ph | — | Tz1 | $C_6H_{13}$ |
| 1-126 | 3 | 1 | 5 | 1 | —O— | Ph | — | Gp1 | — | — | $OC_8H_{17}$ |
| 1-127 | 3 | 1 | 5 | 1 | —O— | Ph | — | Id2 | — | — | $C_{10}H_{21}$ |
| 1-128 | 3 | 2 | 5 | 2 | —O— | Ph | — | Pr1 | — | — | $OCH_2CH(CH_3)OC_4H_9$ |
| 1-129 | 4 | 1 | 5 | 1 | —O— | Ph | — | Tz2 | — | — | $C_6H_{13}$ |
| 1-130 | 4 | 1 | 5 | 1 | —O— | Ph | — | Btb1 | — | — | $C_5H_{11}$ |
| 1-131 | 4 | 1 | 5 | 1 | —O— | Ph | — | Ep1 | — | — | $C_{13}H_{27}$ |
| 1-132 | 4 | 2 | 5 | 2 | —O— | Ph | — | Cy | — | — | $C_9H_{19}$ |
| 1-133 | 4 | 1 | 5 | 1 | —O— | Ph | — | Bob1 | — | — | $C_3H_7$ |
| 1-134 | 5 | 2 | 5 | 1 | —O— | Ph | — | Ph | — | — | $COOC_{14}H_{29}$ |
| 1-135 | 5 | 1 | 5 | 1 | —O— | Ph | — | Ep2 | — | — | $C_7H_{15}$ |
| 1-136 | 5 | 1 | 5 | 2 | —O— | Cy | — | Ph | —OCO— | Tn | $C_6H_{13}$ |
| 1-137 | 5 | 1 | 5 | 1 | —O— | Py2 | — | Id2 | — | — | $C_8H_{17}$ |
| 1-138 | 6 | 1 | 5 | 2 | —O— | Ph | — | Btb2 | — | Cy | $C_5H_{11}$ |
| 1-139 | 6 | 1 | 5 | 1 | —O— | Cy | — | Ph | —OCH$_2$— | Cy | $C_{12}H_{25}$ |
| 1-140 | 6 | 1 | 5 | 1 | —OC— | Ph | —COO— | Ph | — | — | $OC_6H_{13}$ |
| 1-141 | 7 | 1 | 5 | 1 | —O— | Ph | — | Py1 | — | — | $OC_8H_{17}$ |
| 1-142 | 7 | 1 | 5 | 1 | — | Ph | — | Py2 | — | Ph3Cl | $C_9H_{19}$ |
| 1-143 | 8 | 1 | 5 | 1 | —O— | Ph | —C≡C— | Ph | — | Ph | $C_{10}H_{21}$ |
| 1-144 | 8 | 1 | 5 | 1 | —O— | Py2 | — | Ph | —OCH$_2$— | Tn | $C_7H_{15}$ |
| 1-145 | 9 | 1 | 5 | 1 | —COO— | Ph | — | Gp2 | — | — | $C_6H_{13}$ |
| 1-146 | 10 | 1 | 5 | 1 | —O— | Ph | — | Pr2 | — | — | $C_9H_{19}$ |
| 1-147 | 1 | 1 | 6 | 1 | —O— | Np | — | — | — | — | $C_{10}H_{21}$ |
| 1-148 | 1 | 3 | 6 | 5 | —O— | Ph | — | Pa | — | Ph | $C_6H_{13}$ |
| 1-149 | 2 | 1 | 6 | 1 | —O— | Ph | — | Py2 | — | Ph | $C_5H_{11}$ |
| 1-150 | 2 | 2 | 6 | 2 | —O— | Ph | — | Ph | — | Py1 | $C_7H_{15}$ |

-continued

| Ex. Comp. No. | $C_mH_{2m+1}O(CH_2)_n(CF_2)_p(CH_2)_q$—$Y^1$ | | | | | $A^1$ | | | | | $R^1$ |
|---|---|---|---|---|---|---|---|---|---|---|---|
| | m | n | p | q | —$Y^1$— | $A^2$ | $X^1$ | $A^3$ | $X^2$ | $A^4$ | |
| 1-151 | 2 | 1 | 6 | 1 | —O— | Ph | —OCO— | Ph | — | — | $C_{10}H_{21}$ |
| 1-152 | 3 | 1 | 6 | 1 | —O— | Ph | — | Tz2 | — | Ph | $C_4H_9$ |
| 1-153 | 3 | 2 | 6 | 2 | —O— | Ph | $CH_2CH_2$ | Ph | — | — | $C_{12}H_{25}$ |
| 1-154 | 3 | 1 | 6 | 1 | —O— | Ph | —OCO— | Ph3F | — | Py1 | $C_6H_{13}$ |
| 1-155 | 3 | 1 | 6 | 1 | —O— | Ph | — | Tz2 | — | Ph | $C_8H_{17}$ |
| 1-156 | 4 | 1 | 6 | 1 | —OCO— | Ph | — | Ep1 | — | — | $C_9H_{19}$ |
| 1-157 | 4 | 1 | 6 | 1 | —O— | Ph | — | Pr1 | — | — | $C_5H_{11}$ |
| 1-158 | 4 | 2 | 6 | 1 | —O— | Pr2 | — | Ph | —OCO— | Id2 | $C_7H_{15}$ |
| 1-159 | 5 | 1 | 6 | 1 | —O— | Ph | — | Py1 | — | — | $COOC_6H_{13}$ |
| 1-160 | 5 | 1 | 6 | 1 | —O— | Cy | — | Ph | $CH_2CH_2$ | Cy | $C_3H_7$ |
| 1-161 | 5 | 2 | 6 | 1 | — | Ph | — | Ph | — | Cm2 | $C_{12}H_{25}$ |
| 1-162 | 6 | 1 | 6 | 1 | — | Ph | — | Ph | — | Py1 | $C_6H_{13}$ |
| 1-163 | 6 | 1 | 6 | 1 | —O— | Pr2 | — | Np | — | — | $SC_8H_{17}$ |
| 1-164 | 7 | 1 | 6 | 1 | —O— | Ph | —COO— | Ph | — | — | $C_9H_{19}$ |
| 1-165 | 7 | 1 | 6 | 1 | —O— | Cy | — | Ph | —OCH$_2$— | Tn | $C_3H_7$ |
| 1-166 | 8 | 1 | 6 | 1 | —O— | Ph | — | Ph | —COO— | Tn | $C_8H_{17}$ |
| 1-167 | 10 | 1 | 6 | 1 | —O— | Py2 | — | Ph | —OCO— | Ph | F |
| 1-168 | 1 | 1 | 7 | 1 | —O— | Py2 | — | Ph | —OCH$_2$— | Cy | $C_4H_9$ |
| 1-169 | 1 | 1 | 7 | 1 | —O— | Ph | — | Ph | — | Id2 | $C_5H_{11}$ |
| 1-170 | 1 | 2 | 7 | 2 | — | Ph | — | Btb1 | — | — | $C_6H_{13}$ |
| 1-171 | 2 | 1 | 7 | 1 | —O— | Ph | — | Py1 | — | — | $C_7H_{15}$ |
| 1-172 | 2 | 1 | 7 | 1 | —O— | Py2 | — | Id2 | — | — | $C_{10}H_{21}$ |
| 1-173 | 2 | 2 | 7 | 2 | —O— | Ep2 | — | — | — | — | $C_9H_{19}$ |
| 1-174 | 3 | 1 | 7 | 1 | —O— | Ph | —CH$_2$O— | Ph | — | — | $C_6H_{13}$ |
| 1-175 | 3 | 1 | 7 | 1 | —O— | Ph | —C≡C— | Ph | — | Py1 | $C_{10}H_{21}$ |
| 1-176 | 3 | 2 | 7 | 1 | —O— | Ph | — | Pr2 | — | Ph | $C_{12}H_{25}$ |
| 1-177 | 3 | 1 | 7 | 1 | — | Ph | — | Pr1 | — | — | $C_5H_{11}$ |
| 1-178 | 4 | 1 | 7 | 1 | —O— | Ph | — | Ph | — | Td | $C_6H_{13}$ |
| 1-179 | 4 | 1 | 7 | 1 | —O— | Pr2 | — | Ph | —OCH$_2$— | Cy | $C_8H_{17}$ |
| 1-180 | 4 | 1 | 7 | 2 | —O— | Ph | —COO— | Ph | — | — | $C_{10}H_{21}$ |
| 1-181 | 5 | 1 | 7 | 1 | —O— | Ph | — | Pa | — | — | $C_9H_{19}$ |
| 1-182 | 5 | 1 | 7 | 1 | —O— | Ph | — | Ph | — | — | $OCOC_6H_{13}$ |
| 1-183 | 5 | 1 | 7 | 1 | —O— | Cy | — | Ph | $CH_2CH_2$ | Ph | $C_3H_7$ |
| 1-184 | 6 | 1 | 7 | 1 | —O— | Ph | — | Ph | — | Py1 | $C_6H_{13}$ |
| 1-185 | 6 | 1 | 7 | 1 | —O— | Ph | — | Cy | — | — | $OCOCH_2CH(CN)C_2H_5$ |
| 1-186 | 7 | 1 | 7 | 1 | —O— | Cy | — | Ph | —OCO— | Cy | $C_8H_{17}$ |
| 1-187 | 1 | 1 | 8 | 1 | —O— | Ph | — | Td | — | — | $C_9H_{19}$ |
| 1-188 | 1 | 1 | 8 | 1 | —O— | Pr2 | — | Ph | —OCH$_2$— | Tn | $C_{10}H_{21}$ |
| 1-189 | 1 | 1 | 8 | 1 | —O— | Pr1 | — | Id2 | — | — | $C_6H_{13}$ |
| 1-190 | 2 | 1 | 8 | 1 | —O— | Ph | — | Cy | — | Ph | $C_7H_{15}$ |
| 1-191 | 2 | 1 | 8 | 1 | —O— | Ph | — | Py1 | — | — | $C_9H_{19}$ |
| 1-192 | 2 | 1 | 8 | 1 | —O— | Py2 | — | Ph | —OCH$_2$— | Ph | $C_5H_{11}$ |
| 1-193 | 2 | 2 | 8 | 2 | —O— | Ph | — | Tz1 | — | — | $C_6H_{13}$ |
| 1-194 | 3 | 1 | 8 | 1 | —O— | Ph | — | Bta1 | — | — | $C_{10}H_{21}$ |
| 1-195 | 3 | 1 | 8 | 1 | —OCO— | Ph | — | Pd | — | Ph | $C_{12}H_{25}$ |
| 1-196 | 3 | 1 | 8 | 1 | —O— | Py2 | — | Ph | $CH_2CH_2$ | Id2 | $C_6H_{13}$ |
| 1-197 | 3 | 1 | 8 | 1 | —O— | Ph | — | Pr2 | — | Ph | $C_4H_9$ |
| 1-198 | 4 | 1 | 8 | 1 | —O— | Ph | — | Bob2 | — | Cy | $OC_8H_{17}$ |
| 1-199 | 4 | 1 | 8 | 1 | —O— | Btb2 | — | Ph | — | — | $C_{12}H_{25}$ |
| 1-200 | 4 | 1 | 8 | 1 | —O— | Ph | — | Ph | — | — | $C≡CC_9H_{19}$ |
| 1-201 | 5 | 1 | 8 | 1 | —O— | Ph | — | Pr2 | — | — | $C_6H_{13}$ |
| 1-202 | 5 | 1 | 8 | 1 | —O— | Np | — | — | — | — | $OC_5H_{11}$ |
| 1-203 | 6 | 1 | 8 | 1 | —O— | Ph | — | Tn | — | — | $C_{10}H_{21}$ |
| 1-204 | 7 | 1 | 8 | 1 | —O— | Cy | — | Ph | —OCO— | Ph | $C_6H_{13}$ |
| 1-205 | 1 | 1 | 9 | 1 | — | Ph | — | Tz1 | — | Ph | $C_8H_{17}$ |
| 1-206 | 1 | 1 | 9 | 1 | —O— | Ph | —C≡C— | Pd | — | — | $C_4H_9$ |
| 1-207 | 1 | 2 | 9 | 2 | —O— | Ph2M | — | Tz1 | — | Ph | $C_8H_{16}CH=CH_2$ |
| 1-208 | 2 | 1 | 9 | 1 | —O— | Ph | — | Py1 | — | — | $C_9H_{19}$ |
| 1-209 | 2 | 1 | 9 | 1 | —O— | Ph | — | Ep1 | — | — | $OC_{10}H_{21}$ |
| 1-210 | 2 | 1 | 9 | 2 | —OCO— | Ph | — | Py2 | — | Ph | $C_6H_{13}$ |
| 1-211 | 3 | 1 | 9 | 1 | —O— | Ph | — | Btb1 | — | — | $C_5H_{11}$ |
| 1-212 | 3 | 1 | 9 | 1 | —O— | Ph | — | Ph2CN | — | — | $OC_6H_{13}$ |
| 1-213 | 4 | 1 | 9 | 1 | —O— | Ph | —COO— | Ph | — | — | $C_7H_{15}$ |
| 1-214 | 4 | 1 | 9 | 1 | —O— | Ep2 | — | — | — | — | $C_9H_{19}$ |
| 1-215 | 1 | 1 | 10 | 1 | —O— | Ph | — | Dx1 | — | — | $C_6H_{13}$ |
| 1-216 | 2 | 1 | 10 | 1 | —O— | Ph | — | Pr2 | — | — | $C_{12}H_{25}$ |
| 1-217 | 3 | 1 | 10 | 1 | — | Boa2 | — | Ph | — | — | $OC_4H_9$ |
| 1-218 | 4 | 1 | 10 | 1 | —O— | Pr2 | — | Cm2 | — | — | $C_7H_{15}$ |
| 1-219 | 2 | 1 | 11 | 1 | —O— | Ph | — | Ph | — | — | H |
| 1-220 | 3 | 1 | 11 | 1 | —O— | Ph | — | Ph | — | — | $COOC_{10}H_{21}$ |
| 1-221 | 4 | 1 | 11 | 1 | —O— | Ph | — | Btb1 | — | — | $C_5H_{11}$ |
| 1-222 | 2 | 1 | 12 | 1 | —O— | Gp2 | — | — | — | — | $C_6H_{13}$ |
| 1-223 | 4 | 1 | 12 | 1 | —O— | Ph | — | Py1 | — | — | $C_3H_7$ |
| 1-224 | 3 | 1 | 13 | 1 | —O— | Ph | — | Tz1 | — | Ph3Br | $C_4H_9$ |
| 1-225 | 2 | 1 | 14 | 1 | —O— | Cy | — | — | — | — | $C_2H_5$ |

-continued

| Ex. Comp. No. | $C_mH_{2m+1}O(CH_2)_n(CF_2)_p(CH_2)_q-Y^1$ | | | | | $A^1$ | | | | | $R^1$ |
|---|---|---|---|---|---|---|---|---|---|---|---|
| | m | n | p | q | —$Y^1$— | $A^2$ | $X^1$ | $A^3$ | $X^2$ | $A^4$ | |
| 1-226 | 1 | 1 | 15 | 1 | —OCO— | Cy | — | Ph | —OCH$_2$— | Id2 | CH$_3$ |
| 1-227 | 1 | 1 | 16 | 1 | —O— | Ph | — | Ph2F | — | — | C$_6$H$_{13}$ |
| 1-228 | 4 | 1 | 3 | 1 | —O— | Ph | — | Py1 | — | — | OCH$_2$(CF$_2$)$_4$CH$_2$OCH$_2$ |
| 1-229 | 3 | 2 | 4 | 2 | —O— | Ph | — | Ph | — | — | OCH$_2$(CF$_2$)$_2$CH$_2$OC$_4$H$_9$ |
| 1-230 | 4 | 1 | 4 | 1 | —O— | Py2 | — | Ph | — | — | C$_8$F$_{17}$ |
| 1-231 | 5 | 1 | 3 | 1 | —O— | Py2 | — | Ph | — | — | OCH$_2$C$_5$H$_{11}$ |
| 1-232 | 4 | 1 | 3 | 1 | —O— | Ph | — | Py1 | — | — | C$_{10}$H$_{21}$ |

Specific examples of the optically active mesomorphic compound of the formula (I) may include those represented by the following structural formulae 2-1 to 2-231 including the abbreviations for respective cyclic groups described above.

| Ex. Comp. No. | $C_mH_{2m+1}O(CH_2)_n(CF_2)_p(CH_2)_q-Y^1$ | | | | | $A^1$ | | | | | $R^1$ |
|---|---|---|---|---|---|---|---|---|---|---|---|
| | m | n | p | q | —$Y^1$— | $A^2$ | $X^1$ | $A^3$ | $X^2$ | $A^4$ | |
| 2-1 | 1 | 4 | 1 | 4 | —O— | Ph | — | Ph | — | — | CH$_3$<br>\|<br>O(CH$_2$)$_5$*CHC$_2$H$_5$ |
| 2-2 | 2 | 1 | 1 | 1 | —O— | Py2 | — | Ph | — | — | F<br>\|<br>OCH$_2$*CHC$_6$H$_{13}$ |
| 2-3 | 3 | 1 | 4 | 1 | —OCO— | Ph | — | Ph | — | — | CH$_3$<br>\|<br>(CH$_2$)$_3$*CHC$_2$H$_5$ |
| 2-4 | 3 | 7 | 1 | 7 | —O— | Ep2 | — | Ph | — | — | CN<br>\|<br>O(CH$_2$)$_6$*CHC$_6$H$_{13}$ |
| 2-5 | 3 | 4 | 1 | 4 | —O— | Py2 | — | Ph | —OCO— | Ph | CH$_3$<br>\|<br>O(CH$_2$)$_7$*CHC$_3$H$_7$ |
| 2-6 | 4 | 1 | 1 | 1 | —O— | Ph | — | Btb1 | — | — | F<br>\|<br>OCH$_2$*CHC$_8$H$_{17}$ |
| 2-7 | 4 | 1 | 1 | 1 | —O— | Ph | —COO— | Ph2F | — | — | OCO—Thf |
| 2-8 | 4 | 2 | 1 | 2 | —O— | Py2 | — | Ph | — | — | CH$_3$<br>\|<br>OCH$_2$*CHC$_2$H$_5$ |
| 2-9 | 5 | 1 | 1 | 1 | —O— | Ph | —COO— | Ph | — | — | F<br>\|<br>O(CH$_2$)$_2$*CHC$_5$H$_{11}$ |
| 2-10 | 5 | 1 | 1 | 1 | —O— | Py2 | — | Ph | — | Ph | CF$_3$<br>\|<br>O(CH$_2$)$_2$*CHC$_8$H$_{17}$ |
| 2-11 | 5 | 1 | 1 | 8 | —O— | Py2 | — | Ph | — | — | CF$_3$<br>\|<br>COO*CHC$_6$H$_{13}$ |
| 2-12 | 6 | 1 | 1 | 1 | —O— | Ph | — | Cy | — | — | CN<br>\|<br>OCH$_2$*C(CH$_3$)C$_4$H$_9$ |
| 2-13 | 6 | 3 | 1 | 3 | —O— | Ph | — | Ph | — | — | OCH$_2$—Lc2(5,5) |
| 2-14 | 6 | 2 | 1 | 2 | —COO— | Ph | —OCO— | Ph | — | — | CH$_3$<br>\|<br>O(CH$_2$)$_2$*CHOC$_9$H$_{19}$ |
| 2-15 | 7 | 2 | 1 | 2 | — | Py2 | — | Ph | — | — | F<br>\|<br>OCO*CHC$_2$H$_5$ |

-continued

| Ex. Comp. | $C_mH_{2m+1}O(CH_2)_n(CF_2)_p(CH_2)_q-Y^1$ | | | | | $A^1$ | | | | | |
|---|---|---|---|---|---|---|---|---|---|---|---|
| No. | m | n | p | q | $-Y^1-$ | $A^2$ | $X^1$ | $A^3$ | $X^2$ | $A^4$ | $R^1$ |
| 2-16 | 4 | 1 | 3 | 1 | $-O-$ | Ph | — | Ep1 | — | — | Cl  CH$_3$<br>\|   \|<br>OCO*CH*CHC$_2$H$_5$ |
| 2-17 | 8 | 1 | 1 | 1 | — | Tn | $-COO-$ | Ph | — | Py1 | CH$_3$<br>\|<br>OCO*CHOC$_{12}$H$_{25}$ |
| 2-18 | 8 | 2 | 1 | 2 | $-O-$ | Ph | CH=CH | Ph | — | — | CF$_3$<br>\|<br>OCOCH$_2$*CHC$_7$H$_{15}$ |
| 2-19 | 9 | 1 | 1 | 1 | $-O-$ | Ph | — | Boa1 | — | — | CH$_3$<br>\|<br>O(CH$_2$)$_2$*CHC$_8$H$_{17}$ |
| 2-20 | 10 | 1 | 1 | 1 | $-O-$ | Bta2 | — | Ph | — | — | F<br>\|<br>OCH$_2$*CHC$_{12}$H$_{25}$ |
| 2-21 | 11 | 1 | 1 | 1 | $-O-$ | Py2 | — | Cm2 | — | — | CF$_3$<br>\|<br>(CH$_2$)$_2$*CHC$_6$H$_{13}$ |
| 2-22 | 12 | 2 | 1 | 2 | — | Ph | — | Ph | — | Pr1 | CN<br>\|<br>O(CH$_2$)$_2$*CHC$_5$H$_{11}$ |
| 2-23 | 13 | 2 | 1 | 2 | $-O-$ | Ph | $-OCH_2-$ | Ph | — | — | CH$_3$<br>\|<br>O(CH$_2$)$_2$*CHOC$_3$H$_7$ |
| 2-24 | 14 | 1 | 1 | 1 | $-O-$ | Ph | — | Py1 | — | Ph | F<br>\|<br>OCO*CHC$_9$H$_{19}$ |
| 2-25 | 15 | 1 | 1 | 1 | $-O-$ | Ph | — | — | — | — | CF$_3$<br>\|<br>O(CH$_2$)$_2$*CHC$_5$H$_{11}$ |
| 2-26 | 16 | 1 | 1 | 1 | $-O-$ | Ph | — | Gp1 | — | — | OCH$_2$—Lc1(8,0) |
| 2-27 | 1 | 1 | 2 | 1 | $-O-$ | Pr2 | — | Ph | — | — | F<br>\|<br>OCH$_2$*C(CH$_3$)C$_6$H$_{13}$ |
| 2-28 | 1 | 2 | 2 | 2 | $-O-$ | Py2 | — | Ph | $-OCO-$ | Cy | CF$_3$<br>\|<br>(CH$_2$)$_3$*CHC$_{11}$H$_{23}$ |
| 2-29 | 2 | 1 | 2 | 1 | $-OCO-$ | Py2 | — | Ph | — | — | F<br>\|<br>OCH$_2$*CHC$_3$H$_7$ |
| 2-30 | 2 | 1 | 2 | 1 | $-O-$ | Py2 | — | Cy | — | — | CH$_3$<br>\|<br>O(CH$_2$)$_2$*CHC$_9$H$_{19}$ |
| 2-31 | 2 | 2 | 2 | 2 | $-O-$ | Ph | CH$_2$CH$_2$ | Ph | — | — | CN<br>\|<br>OCH$_2$*CHC$_8$H$_{17}$ |
| 2-32 | 2 | 6 | 2 | 6 | $-O-$ | Ph | — | Ph3F | — | — | OCH$_2$—La2(6,0) |
| 2-33 | 3 | 1 | 2 | 1 | — | Ph | — | Py2 | — | — | F<br>\|<br>OCH$_2$*CHC$_6$H$_{13}$ |
| 2-34 | 3 | 1 | 2 | 1 | $-O-$ | Pr2 | — | Ph | $-OCO-$ | Ph | F<br>\|<br>O(CH$_2$)$_5$*CHC$_4$H$_9$ |
| 2-35 | 3 | 1 | 2 | 1 | $-O-$ | Ph | — | Ph | — | — | OCH$_2$—Thf |
| 2-36 | 3 | 2 | 2 | 2 | $-O-$ | Ph | — | Py1 | — | — | CF$_3$<br>\|<br>COO*CHC$_8$H$_{17}$ |

-continued

| Ex. Comp. No. | $C_mH_{2m+1}O(CH_2)_n(CF_2)_p(CH_2)_q-Y^1$ | | | | | A¹ | | | | | R¹ |
|---|---|---|---|---|---|---|---|---|---|---|---|
| | m | n | p | q | —Y¹— | A² | X¹ | A³ | X² | A⁴ | |
| 2-37 | 4 | 1 | 2 | 1 | —O— | Ph | — | Py1 | — | — | CH₃ \| O*CHC₁₀H₂₁ |
| 2-38 | 4 | 1 | 2 | 1 | —OCO— | Ph | — | Ep2 | — | — | CH₃ \| OCH₂*CHOCOC₂H₅ |
| 2-39 | 4 | 1 | 2 | 1 | —O— | Ph | —COO— | Ph | — | Tn | CH₃ \| CH₂*CHC₂H₅ |
| 2-40 | 4 | 2 | 2 | 2 | — | Ph | —CH₂O— | Ph | — | — | O—Dp(2) |
| 2-41 | 4 | 3 | 2 | 5 | —O— | Ph | — | Py1 | — | — | CN \| O(CH₂)₄*CHC₅H₁₁ |
| 2-42 | 5 | 1 | 2 | 1 | —O— | Ph | — | Py1 | — | — | F \| OCH₂*CHC₉H₁₉ |
| 2-43 | 5 | 1 | 2 | 1 | —O— | Ph | — | Tz1 | — | Ph | CH₃ \| CH₂OCOCH₂*CHC₂H₅ |
| 2-44 | 5 | 2 | 2 | 2 | — | Ph | —COO— | Ph | — | — | CH₃ \| (CH₂)₂*CHC₇H₁₅ |
| 2-45 | 5 | 3 | 2 | 4 | —O— | Ph | — | Ph | — | Py1 | O—Lc2(3,3) |
| 2-46 | 6 | 1 | 2 | 1 | —O— | Py2 | — | Ph | CH₂CH₂ | Cy | CN \| (CH₂)₂*CHC₈H₁₇ |
| 2-47 | 6 | 1 | 2 | 1 | —O— | Ph | — | Pd | — | — | CH₃ \| O*CHC₉H₁₉ |
| 2-48 | 6 | 1 | 2 | 1 | —O— | Py2 | — | Cm2 | — | — | F \| —*CHC₂H₅ |
| 2-49 | 6 | 1 | 2 | 1 | —OCO— | Ph | —C≡C— | Ph | — | — | COO—La1(1,1) |
| 2-50 | 7 | 1 | 2 | 1 | —O— | Ph | — | Ep1 | — | — | F \| OCH₂*CHC₄H₉ |
| 2-51 | 7 | 2 | 2 | 2 | —C≡C— | Ph | — | Py1 | — | — | CF₃ \| OCO*CHC₈H₁₇ |
| 2-52 | 7 | 1 | 2 | 1 | —O— | Cy | —COO— | Ph | — | — | F \| OCH₂*CHC₈H₁₇ |
| 2-53 | 8 | 1 | 2 | 5 | —O— | Ph | — | Ph | —OCO— | Ph2TF | CH₃ \| O(CH₂)₄*CHOC₅H₁₁ |
| 2-54 | 8 | 1 | 2 | 1 | —O— | Ph | — | Py1 | — | — | CH₃ \| OCH₂*CHC₂H₅ |
| 2-55 | 9 | 2 | 2 | 2 | — | Ph | —OCO— | Ph | — | — | CF₃ \| COO*CHC₅H₁₁ |
| 2-56 | 9 | 1 | 2 | 1 | —O— | Ep2 | — | — | — | — | CN \| OCH₂*CHC₂H₅ |
| 2-57 | 10 | 1 | 2 | 1 | —O— | Ph | — | Ph | — | Cy | OCH₂—Lc1(6,0) |
| 2-58 | 11 | 1 | 2 | 1 | —O— | Ph | — | Py2 | — | Ph | F \| O(CH₂)₄*CHC₅H₁₁ |

-continued

| Ex. Comp. No. | $C_mH_{2m+1}O(CH_2)_n(CF_2)_p(CH_2)_q-Y^1$ | | | | | $A^1$ | | | | | $R^1$ |
|---|---|---|---|---|---|---|---|---|---|---|---|
| | m | n | p | q | $-Y^1-$ | $A^2$ | $X^1$ | $A^3$ | $X^2$ | $A^4$ | |
| 2-59 | 12 | 2 | 2 | 1 | $-O-$ | Ph | — | Np | — | — | $\underset{O(CH_2)_4*CHC_5H_{11}}{CH_3}$ |
| 2-60 | 14 | 1 | 2 | 1 | $-O-$ | Pr2 | — | Ph | $-OCO-$ | Cy | $\underset{O(CH_2)_2*CHC_4H_9}{F}$ |
| 2-61 | 1 | 6 | 3 | 3 | $-O-$ | Ph | — | Pr1 | — | — | $\underset{OCH_2*C(CH_3)C_5H_{11}}{CN}$ |
| 2-62 | 1 | 1 | 3 | 1 | $-O-$ | Ph | $-COO-$ | Ph | — | Ph | $OCO-La2(5,0)$ |
| 2-63 | 2 | 1 | 3 | 1 | $-O-$ | Py2 | — | Ph | $-OCO-$ | Tn | $\underset{O(CH_2)_4*CHC_5H_{11}}{CF_3}$ |
| 2-64 | 2 | 1 | 3 | 1 | $-OCH_2-$ | Ph | $-COO-$ | Ph | — | — | $\underset{OCO(CH_2)_2*CHC_5H_{11}}{CN}$ |
| 2-65 | 2 | 3 | 3 | 3 | $-O-$ | Ph | — | Tz2 | — | Ph | $\underset{OCH_2*C(CH_3)C_2H_5}{F}$ |
| 2-66 | 3 | 1 | 3 | 1 | $-O-$ | Py2 | — | Ph | — | — | $OCO-Dp(0)$ |
| 2-67 | 3 | 1 | 3 | 1 | $-O-$ | Ph | — | Py1 | — | — | $\underset{O(CH_2)_2*CHC_6H_{13}}{CF_3}$ |
| 2-68 | 3 | 1 | 3 | 1 | $-CH=CH-$ | Ph | — | Ph | — | — | $\underset{OCH_2*CHC_8H_{17}}{F}$ |
| 2-69 | 3 | 1 | 3 | 1 | $-O-$ | Py2 | — | Py | — | — | $\underset{OCH_2*C(CH_3)C_6H_{13}}{CN}$ |
| 2-70 | 4 | 1 | 3 | 1 | $-O-$ | Ph | — | Py1 | — | — | $\underset{O(CH_2)_2*CHC_4H_9}{CF_3}$ |
| 2-71 | 4 | 2 | 3 | 2 | — | Btb2 | — | Ph | — | — | $\underset{OCH_2*CHC_3H_7}{F}$ |
| 2-72 | 4 | 3 | 3 | 3 | $-O-$ | Pr2 | — | Cy | — | — | $OCH_2-Thf$ |
| 2-73 | 5 | 1 | 3 | 1 | $-O-$ | Ph | $-OCH_2-$ | Ph | — | — | $\underset{OCH_2*CHC_7H_{15}}{CF_3}$ |
| 2-74 | 5 | 1 | 3 | 1 | $-O-$ | Ph | — | Ep1 | — | — | $\underset{O(CH_2)_4*CHOC_3H_7}{CH_3}$ |
| 2-75 | 5 | 1 | 3 | 1 | $-OCH_2-$ | Ph | — | Pr1 | — | — | $\underset{OCH_2*CHC_{10}H_{21}}{F}$ |
| 2-76 | 6 | 1 | 3 | 1 | $-O-$ | Ph | — | Ph | — | Ph | $\underset{OCH_2*CHC_2H_5}{CN}$ |
| 2-77 | 6 | 1 | 3 | 1 | $-O-$ | Ph | $-OCO-$ | Ph | — | — | $\underset{OCO*CHC_6H_{13}}{CF_3}$ |
| 2-78 | 7 | 1 | 3 | 1 | $-O-$ | Py2 | — | Boa2 | — | Ph | $\underset{(CH_2)_2*CHC_8H_{17}}{F}$ |
| 2-79 | 7 | 2 | 3 | 2 | $-O-$ | Ph | — | Py1 | — | — | $OCH_2-Lc2(1,1)$ |
| 2-80 | 7 | 1 | 3 | 1 | $-O-$ | Pr2 | — | Ph | $-OCO-$ | Tn | $\underset{CH_2*C(CH_3)C_2H_5}{CN}$ |

-continued

| Ex. Comp. No. | $C_mH_{2m+1}O(CH_2)_n(CF_2)_p(CH_2)_q-Y^1$ | | | | | $A^1$ | | | | | $R^1$ |
|---|---|---|---|---|---|---|---|---|---|---|---|
| | m | n | p | q | $-Y^1-$ | $A^2$ | $X^1$ | $A^3$ | $X^2$ | $A^4$ | |
| 2-81 | 8 | 1 | 3 | 1 | $-O-$ | Ph | $CH_2CH_2$ | Ph | — | — | $\underset{O(CH_2)_4*CHC_4H_9}{\overset{CF_3}{|}}$ |
| 2-82 | 8 | 1 | 3 | 5 | $-O-$ | Ph | — | Py1 | — | — | $\underset{OCH_2*CHC_2H_5}{\overset{F}{|}}$ |
| 2-83 | 8 | 1 | 3 | 1 | $-O-$ | Cy | — | Ph | $-OCH_2-$ | Ph | $\underset{(CH_2)_2*CHC_5H_{11}}{\overset{CF_3}{|}}$ |
| 2-84 | 9 | 1 | 3 | 1 | $-O-$ | Ph | — | Ph | — | — | $\underset{COOCH_2*CHC_8H_{17}}{\overset{CH_3}{|}}$ |
| 2-85 | 9 | 1 | 3 | 1 | $-O-$ | Ph | — | Ph23F | — | — | $\underset{OCH_2*CHC_2H_5}{\overset{F}{|}}$ |
| 2-86 | 10 | 1 | 3 | 1 | $-O-$ | Ph | — | Td | — | Ph | $\underset{O(CH_2)_5*CHC_9H_{19}}{\overset{CH_3}{|}}$ |
| 2-87 | 11 | 1 | 3 | 1 | $-O-$ | Py2 | — | Ph | $CH_2CH_2$ | Ph | $OCH_2-Lc(1,1)$ |
| 2-88 | 13 | 1 | 3 | 1 | — | Py2 | — | Btb2 | — | Ph | $\underset{O(CH_2)_3*CHC_7H_{15}}{\overset{CF_3}{|}}$ |
| 2-89 | 14 | 1 | 3 | 1 | $-O-$ | Py2 | — | Ph3F | — | — | $\underset{OCH_2*C(CH_3)C_{10}H_{21}}{\overset{CN}{|}}$ |
| 2-90 | 1 | 2 | 4 | 2 | $-O-$ | Ph | $-CH_2O-$ | Ph | — | — | $\underset{O(CH_2)_8*CHC_5H_{11}}{\overset{CH_3}{|}}$ |
| 2-91 | 1 | 4 | 4 | 4 | $-O-$ | Ph | — | Id2 | — | — | $\underset{CH_2*CHC_6H_{13}}{\overset{CH_3}{|}}$ |
| 2-92 | 2 | 1 | 4 | 1 | $-O-$ | Cy | — | Ph | $-OCO-$ | Id2 | $\underset{(CH_2)_4*CHC_{13}H_{27}}{\overset{CH_3}{|}}$ |
| 2-93 | 2 | 1 | 4 | 1 | $-O-$ | Ph | — | Gp1 | — | — | $OCH_2-La2(8,0)$ |
| 2-94 | 2 | 3 | 4 | 3 | $-O-$ | Ph | — | Py1 | — | — | $\underset{O(CH_2)_2*CHOC_7H_{15}}{\overset{CH_3}{|}}$ |
| 2-95 | 3 | 1 | 4 | 1 | $-O-$ | Ph | — | Cy | — | — | $\underset{OCH_2*C(CH_3)C_{10}H_{21}}{\overset{F}{|}}$ |
| 2-96 | 3 | 1 | 4 | 1 | — | Ph | $-COO-$ | Ph | — | — | $\underset{OCO*CHC_5H_{11}}{\overset{CF_3}{|}}$ |
| 2-97 | 4 | 1 | 3 | 1 | $-OCO-$ | Ph | — | Ph | — | — | $\underset{OCH_2*CHOC_5H_{11}}{\overset{CH_3}{|}}$ |
| 2-98 | 3 | 2 | 4 | 2 | $-O-$ | Ph | — | Dx2 | — | Ph | $OCO-Pla$ |
| 2-99 | 4 | 1 | 4 | 1 | $-O-$ | Ph | — | Tz1 | — | Ph | $\underset{OCH_2*CHC_4H_9}{\overset{F}{|}}$ |
| 2-100 | 4 | 1 | 4 | 1 | $-O-$ | Gp2 | — | — | — | — | $\underset{O(CH_2)_4*CHC_6H_{13}}{\overset{CF_3}{|}}$ |
| 2-101 | 4 | 1 | 4 | 1 | $-O-$ | Ph | — | Ph | — | — | $OCH_2-La(1,1)$ |
| 2-102 | 4 | 1 | 4 | 1 | $-O-$ | Ph | — | Dt1 | — | Ph | $\underset{OCH_2*C(CH_3)C_8H_{17}}{\overset{CF_3}{|}}$ |

-continued

| Ex. Comp. No. | $C_mH_{2m+1}O(CH_2)_n(CF_2)_p(CH_2)_q-Y^1$ | | | | | | | A$^1$ | | | | |
|---|---|---|---|---|---|---|---|---|---|---|---|---|
| | m | n | p | q | $-Y^1-$ | A$^2$ | X$^1$ | A$^3$ | X$^2$ | A$^4$ | R$^1$ | |
| 2-103 | 4 | 2 | 4 | 2 | $-OCO-$ | Ph | — | Pa | — | — | $\underset{O(CH_2)_2{}^*CHC_4H_9}{\overset{CN}{\vert}}$ | |
| 2-104 | 5 | 1 | 4 | 1 | $-O-$ | Py2 | — | Io2 | — | — | $\underset{CH_2{}^*CHC_2H_5}{\overset{CF_3}{\vert}}$ | |
| 2-105 | 5 | 1 | 4 | 1 | $-O-$ | Ph | — | Ph | — | Cy | OCO-Thf | |
| 2-106 | 5 | 2 | 4 | 2 | $-O-$ | Ph | — | Py1 | — | — | $\underset{OCH_2{}^*C(CH_3)C_6H_{13}}{\overset{F}{\vert}}$ | |
| 2-107 | 5 | 1 | 4 | 1 | $-O-$ | Ph | — | Ph | — | Py1 | $\underset{(CH_2)_2{}^*CHC_9H_{19}}{\overset{CF_3}{\vert}}$ | |
| 2-108 | 6 | 2 | 4 | 1 | $-O-$ | Py2 | — | Ph | — | — | $\underset{OCH_2{}^*CHC_5H_{11}}{\overset{CF_3}{\vert}}$ | |
| 2-109 | 6 | 1 | 4 | 1 | $-O-$ | Ph2F | — | Ph | — | Py1 | $\underset{-C\equiv C(CH_2)_2{}^*CHC_2H_5}{\overset{CH_3}{\vert}}$ | |
| 2-110 | 6 | 1 | 4 | 1 | $-O-$ | Ph | $-C\equiv C-$ | Ph | — | — | $OCH_2-Lc2(6,0)$ | |
| 2-111 | 7 | 1 | 4 | 1 | — | Ph | — | Np | — | — | $\underset{OCH_2{}^*CHC_{13}H_{27}}{\overset{F}{\vert}}$ | |
| 2-112 | 7 | 1 | 4 | 2 | $-O-$ | Ph | — | Ph | — | Ph | $\underset{OCH_2{}^*C(CH_3)C_3H_7}{\overset{F}{\vert}}$ | |
| 2-113 | 8 | 1 | 4 | 1 | $-O-$ | Py2 | — | Ph | $-OCH_2-$ | Id2 | $\underset{(CH_2)_3{}^*CHC_{12}H_{26}}{\overset{CH_3}{\vert}}$ | |
| 2-114 | 8 | 1 | 4 | 1 | $-O-$ | Ph | $-OCH_2-$ | Ph | — | — | $\underset{OCH_2{}^*CHC_6H_{13}}{\overset{F}{\vert}}$ | |
| 2-115 | 8 | 1 | 4 | 1 | $-O-$ | Py2 | — | Ph | $-OCO-$ | Id2 | $\underset{(CH_2)_2{}^*CHC_4H_9}{\overset{CF_3}{\vert}}$ | |
| 2-116 | 9 | 1 | 4 | 1 | $-OCH_2-$ | Ph | — | Dt2 | — | — | $OCH_2-La2(8,0)$ | |
| 2-117 | 9 | 1 | 4 | 3 | $-O-$ | Ph | — | Tz1 | — | Ph | $\underset{O(CH_2)_5{}^*CHC_5H_{11}}{\overset{CH_3}{\vert}}$ | |
| 2-118 | 4 | 1 | 3 | 1 | $-O-$ | Ph | — | Td | — | — | $\underset{{}^*CHC_6H_{13}}{\overset{F}{\vert}}$ | |
| 2-119 | 10 | 1 | 4 | 1 | $-O-$ | Ph | — | Py1 | — | Ph | $\underset{OCH_2{}^*CHC_7H_{15}}{\overset{F}{\vert}}$ | |
| 2-120 | 12 | 1 | 4 | 1 | $-O-$ | Cy | — | Ph | $CH_2CH_2$ | Tn | $\underset{CH_2{}^*C(CH_3)C_{11}H_{23}}{\overset{CN}{\vert}}$ | |
| 2-121 | 1 | 1 | 5 | 1 | $-O-$ | Ph | — | Tn | — | — | $\underset{CO(CH_2)_3{}^*CHC_6H_{13}}{\overset{CF_3}{\vert}}$ | |
| 2-122 | 1 | 3 | 5 | 3 | $-O-$ | Ph | $-COO-$ | Ph | $-COO-$ | Ph | $\underset{OCH_2{}^*CHC_4H_9}{\overset{F}{\vert}}$ | |
| 2-123 | 2 | 1 | 5 | 1 | $-O-$ | Ph | — | Py1 | — | — | $OCH_2-La2(8,0)$ | |

-continued

| Ex. Comp. No. | $C_mH_{2m+1}O(CH_2)_n(CF_2)_p(CH_2)_q-Y^1$ | | | | | $A^1$ | | | | | |
|---|---|---|---|---|---|---|---|---|---|---|---|
| | m | n | p | q | $-Y^1-$ | $A^2$ | $X^1$ | $A^3$ | $X^2$ | $A^4$ | $R^1$ |
| 2-124 | 4 | 1 | 3 | 1 | $-OCO-$ | Ph | — | Ph | — | — | $\underset{OCH_2*CHC_6H_{13}}{F}$ |
| 2-125 | 2 | 3 | 5 | 1 | $-O-$ | Ph | — | Ph | — | Tz1 | $\underset{OCH_2*CHOCO*CHC_2H_5}{CH_3 \quad CH_3}$ |
| 2-126 | 3 | 1 | 5 | 1 | $-O-$ | Ph | — | Gp1 | — | — | $OCO-Dp(2)$ |
| 2-127 | 3 | 1 | 5 | 1 | $-O-$ | Ph | — | Id2 | — | — | $\underset{CH_2*CHC_5H_{11}}{CH_3}$ |
| 2-128 | 3 | 2 | 5 | 2 | $-O-$ | Pr2 | — | Ph | — | — | $\underset{S-(CH_2)_4*CHC_4H_9}{CH_3}$ |
| 2-129 | 4 | 1 | 5 | 1 | $-O-$ | Ph | — | Tz2 | — | — | $\underset{O(CH_2)_2*CHC_{11}H_{23}}{CF_3}$ |
| 2-130 | 4 | 1 | 5 | 1 | $-O-$ | Ph | — | Btb1 | — | — | $\underset{OCH_2*C(CH_3)C_3H_7}{CN}$ |
| 2-131 | 4 | 1 | 5 | 1 | $-O-$ | Ep2 | — | Ph | — | — | $\underset{O(CH_2)_5*CHC_8H_{17}}{CF_3}$ |
| 2-132 | 4 | 2 | 5 | 2 | $-O-$ | Ph | — | Cy | — | — | $OCH_2-Lc2(5,0)$ |
| 2-133 | 4 | 1 | 5 | 1 | $-O-$ | Ph | — | Bob1 | — | — | $\underset{(CH_2)_2*CHC_{12}H_{25}}{F}$ |
| 2-134 | 5 | 2 | 5 | 1 | $-O-$ | Ph | — | Ph | — | — | $\underset{OCH_2*CHC_3H_7}{CF_3}$ |
| 2-135 | 5 | 1 | 5 | 1 | $-O-$ | Ph | — | Ep2 | — | — | $\underset{O(CH_2)_4*CHC_5H_{11}}{CH_3}$ |
| 2-136 | 5 | 1 | 5 | 2 | $-O-$ | Cy | — | Ph | $-OCO-$ | Tn | $CH_2O-Lal(6,0)$ |
| 2-137 | 5 | 1 | 5 | 1 | $-O-$ | Py2 | — | Id2 | — | — | $\underset{(CH_2)_3*CHC_6H_{13}}{F}$ |
| 2-138 | 6 | 1 | 5 | 2 | $-O-$ | Ph | — | Btb2 | — | Cy | $\underset{OCH_2*C(CH_3)C_5H_{11}}{CN}$ |
| 2-139 | 6 | 1 | 5 | 1 | $-O-$ | Cy | — | Ph | $-OCH_2$ | Cy | $\underset{OCH_2*CHC_{14}H_{29}}{F}$ |
| 2-140 | 6 | 1 | 5 | 1 | $-OC-$ | Ph | $-COO-$ | Ph | — | — | $\underset{O(CH_2)_2*CHC_8H_{17}}{CH_3}$ |
| 2-141 | 7 | 1 | 5 | 1 | $-O-$ | Ph | — | Py1 | — | — | $OCH_2-La2(6,0)$ |
| 2-142 | 7 | 1 | 5 | 1 | — | Ph | — | Py2 | — | Ph3Cl | $\underset{OCO*CHC_6H_{13}}{CF_3}$ |
| 2-143 | 8 | 1 | 5 | 1 | $-O-$ | Ph | $-C{\equiv}C-$ | Ph | — | Ph | $\underset{O(CH_2)_4*CHC_9H_{19}}{CF_3}$ |
| 2-144 | 8 | 1 | 5 | 1 | $-O-$ | Py2 | — | Ph | $-OCH_2-$ | Tn | $\underset{CH_2*CHC_7H_{15}}{CH_3}$ |
| 2-145 | 9 | 1 | 5 | 1 | $-COO-$ | Ph | — | Gp2 | — | — | $OCH_2-Lc2(1,1)$ |

-continued

| Ex. Comp. No. | $C_mH_{2m+1}O(CH_2)_n(CF_2)_p(CH_2)_q-Y^1$ | | | | | $A^1$ | | | | | |
|---|---|---|---|---|---|---|---|---|---|---|---|
| | m | n | p | q | $-Y^1-$ | $A^2$ | $X^1$ | $A^3$ | $X^2$ | $A^4$ | $R^1$ |
| 2-146 | 10 | 1 | 5 | 1 | $-O-$ | Ph | — | Pr2 | — | — | $\underset{O(CH_2)_5*CHC_4H_9}{\overset{CH_3}{|}}$ |
| 2-147 | 1 | 1 | 6 | 1 | $-O-$ | Np | — | — | — | — | $\underset{OCO*C(CH_3)C_6H_{17}}{\overset{CN}{|}}$ |
| 2-148 | 1 | 3 | 6 | 5 | $-O-$ | Ph | — | Pa | — | Ph | $\underset{(CH_2)_3*CHC_3H_7}{\overset{CF_3}{|}}$ |
| 2-149 | 2 | 1 | 6 | 1 | $-O-$ | Ph | — | Py2 | — | Ph | $\underset{OCO*CHC_7H_{15}}{\overset{-CF_3}{|}}$ |
| 2-150 | 2 | 2 | 6 | 2 | $-O-$ | Ph | — | Ph | — | Py1 | $\underset{(CH_2)_5*CHC_4H_9}{\overset{CH_3}{|}}$ |
| 2-151 | 2 | 1 | 6 | 1 | $-O-$ | Ph | $-OCO-$ | Ph | — | — | $OCH_2-La2(4,0)$ |
| 2-152 | 3 | 1 | 6 | 1 | $-O-$ | Ph | — | Tz2 | — | Ph | $\underset{OCH*CHC_{12}H_{25}}{\overset{CH_3}{|}}$ |
| 2-153 | 3 | 2 | 6 | 2 | $-O-$ | Ph | $CH_2CH_2$ | Ph | — | — | $\underset{O(CH_2)_3*CHC_6H_{13}}{\overset{CF_3}{|}}$ |
| 2-154 | 3 | 1 | 6 | 1 | $-O-$ | Ph | $-OCO-$ | Ph3F | — | Py1 | $OCO-Thf$ |
| 2-155 | 3 | 1 | 6 | 1 | $-O-$ | Ph | — | Tz2 | — | Ph | $\underset{O(CH_2)_2*CHC_8H_{17}}{\overset{F}{|}}$ |
| 2-156 | 4 | 1 | 6 | 1 | $-OCO-$ | Ph | — | Ep1 | — | — | $\underset{OCH_2*C(CH_3)C_6H_{13}}{\overset{CN}{|}}$ |
| 2-157 | 4 | 1 | 6 | 1 | $-O-$ | Ph | — | Pr1 | — | — | $\underset{O(CH_2)_4*CHC_8H_{17}}{\overset{Cl}{|}}$ |
| 2-158 | 4 | 2 | 6 | 1 | $-O-$ | Pr2 | — | Ph | $-OCO-$ | Id2 | $\underset{CH_2*CHC_6H_{13}}{\overset{CH_3}{|}}$ |
| 2-159 | 5 | 1 | 6 | 1 | $-O-$ | Ph | — | Py1 | — | — | $OCO-Dp(0)$ |
| 2-160 | 5 | 1 | 6 | 1 | $-O-$ | Cy | — | Ph | $CH_2CH_2$ | Cy | $\underset{OCH_2*CHCH_2CH=CH_2}{\overset{CF_3}{|}}$ |
| 2-161 | 5 | 2 | 6 | 1 | — | Ph | — | Ph | — | Cm2 | $COOCH_2-La1(3,3)$ |
| 2-162 | 6 | 1 | 6 | 1 | — | Ph | — | Ph | — | Py1 | $\underset{(CH_2)_3*CHC_{12}H_{25}}{\overset{F}{|}}$ |
| 2-163 | 6 | 1 | 6 | 1 | $-O-$ | Pr2 | — | Np | — | — | $\underset{O(CH_2)_6*CHC_6H_{13}}{\overset{CF_3}{|}}$ |
| 2-164 | 7 | 1 | 6 | 1 | $-O-$ | Ph | $-COO-$ | Ph | — | — | $\underset{OCH_2*C(CH_3)C_{12}H_{25}}{\overset{CN}{|}}$ |
| 2-165 | 7 | 1 | 6 | 1 | $-O-$ | Cy | — | Ph | $-OCH_2-$ | Tn | $\underset{(CH_2)_3*CHC_6H_{13}}{\overset{CH_3}{|}}$ |
| 2-166 | 8 | 1 | 6 | 1 | — | Tn | $-COO-$ | Ph | — | Ph | $\underset{O(CH_2)_2*CHC_8H_{17}}{\overset{CF_3}{|}}$ |
| 2-167 | 10 | 1 | 6 | 1 | $-O-$ | Py2 | — | Ph | $-OCO-$ | Ph | $OCO-Thf$ |

-continued

| Ex. Comp. No. | $C_mH_{2m+1}O(CH_2)_n(CF_2)_p(CH_2)_q-Y^1$ | | | | | $A^1$ | | | | | $R^1$ |
|---|---|---|---|---|---|---|---|---|---|---|---|
| | m | n | p | q | $-Y^1-$ | $A^2$ | $X^1$ | $A^3$ | $X^2$ | $A^4$ | |
| 2-168 | 1 | 1 | 7 | 1 | $-O-$ | Py2 | — | Ph | $-OCH_2-$ | Cy | CN<br>\|<br>$OCH_2*C(CH_3)C_6H_{13}$ |
| 2-169 | 1 | 1 | 7 | 1 | $-O-$ | Ph | — | Ph | — | Id2 | $CF_3$<br>\|<br>$(CH_2)_3*CHC_6H_{13}$ |
| 2-170 | 1 | 2 | 7 | 2 | — | Ph | — | Btb1 | — | — | F<br>\|<br>$COCH_2*CHC_7H_{15}$ |
| 2-171 | 2 | 1 | 7 | 1 | $-O-$ | Ph | — | Py1 | — | — | $CH_3$<br>\|<br>$O(CH_2)_8*CHC_6H_{13}$ |
| 2-172 | 2 | 1 | 7 | 1 | $-O-$ | Py2 | — | Id2 | — | — | F<br>\|<br>$CH_2*C(CH_3)C_3H_7$ |
| 2-173 | 2 | 2 | 7 | 2 | $-O-$ | Ep2 | — | — | — | — | $CF_3$<br>\|<br>$O(CH_2)_5*CHC_5H_{11}$ |
| 2-174 | 3 | 1 | 7 | 1 | $-O-$ | Ph | $-CH_2O-$ | Ph | — | — | $OCO-Dp(1)$ |
| 2-175 | 3 | 1 | 7 | 1 | $-O-$ | Ph | $-C\equiv C-$ | Ph | — | Py1 | $CH_3$<br>\|<br>$OCH_2*CHOCH_2C_3F_7$ |
| 2-176 | 3 | 2 | 7 | 1 | $-O-$ | Ph | — | Pr2 | — | Ph | $CF_3$<br>\|<br>$OCH_2*CHC_5H_{11}$ |
| 2-177 | 3 | 1 | 7 | 1 | — | Ph | — | Pr1 | — | — | $CF_3$<br>\|<br>$O(CH_2)_2*CHC_4H_9$ |
| 2-178 | 4 | 1 | 7 | 1 | $-O-$ | Ph | — | Ph | — | Td | F<br>\|<br>$-*CHC_6H_{13}$ |
| 2-179 | 4 | 1 | 7 | 1 | $-O-$ | Pr2 | — | Ph | $-OCH_2-$ | Cy | $OCH_2-La1(5,2)$ |
| 2-180 | 4 | 1 | 7 | 2 | $-O-$ | Ph | $-COO-$ | Ph | — | — | F<br>\|<br>$OCH_2*CHC_{10}H_{21}$ |
| 2-181 | 5 | 1 | 7 | 1 | $-O-$ | Ph | — | Pa | — | — | $CF_3$<br>\|<br>$O(CH_2)_4*CHC_8H_{17}$ |
| 2-182 | 5 | 1 | 7 | 1 | $-O-$ | Ph | — | Ph | — | — | $CH_3$<br>\|<br>$O(CH_2)_6*CHC_6H_{13}$ |
| 2-183 | 5 | 1 | 7 | 1 | $-O-$ | Cy | — | Ph | $CH_2CH_2$ | Ph | $OCH_2-La2(2,0)$ |
| 2-184 | 6 | 1 | 7 | 1 | $-O-$ | Ph | — | Ph | — | Py1 | CN<br>\|<br>$OCH_2*C(CH_3)C_{12}H_{25}$ |
| 2-185 | 6 | 1 | 7 | 1 | $-O-$ | Ph | — | Cy | — | — | $CF_3$<br>\|<br>$O(CH_2)_2*CHC_6H_{13}$ |
| 2-186 | 7 | 1 | 7 | 1 | $-O-$ | Cy | — | Ph | $-OCO-$ | Cy | $OCH_2-Lc1(6,6)$ |
| 2-187 | 1 | 1 | 8 | 1 | $-O-$ | Ph | — | Td | — | — | $CH_3$<br>\|<br>$O(CH_2)_2O*CHC_4H_9$ |
| 2-188 | 1 | 1 | 8 | 1 | $-O-$ | Pr2 | — | Ph | $-OCH_2-$ | Tn | F<br>\|<br>$(CH_2)_2*CHC_3H_7$ |
| 2-189 | 1 | 1 | 8 | 1 | $-O-$ | Pr1 | — | Id2 | — | — | F<br>\|<br>$CH_2*CHC_4H_9$ |

-continued

| Ex. Comp. No. | $C_mH_{2m+1}O(CH_2)_n(CF_2)_p(CH_2)_q-Y^1$ | | | | | A¹ | | | | | R¹ |
|---|---|---|---|---|---|---|---|---|---|---|---|
| | m | n | p | q | —Y¹— | A² | X¹ | A³ | X² | A⁴ | |
| 2-190 | 2 | 1 | 8 | 1 | —O— | Ph | — | Cy | — | Ph | CH₃<br>\|<br>(CH₂)₃*CHC₅H₁₁ |
| 2-191 | 2 | 1 | 8 | 1 | —O— | Ph | — | Py1 | — | — | OCH₂—Lc2(3,3) |
| 2-192 | 2 | 1 | 8 | 1 | —O— | Py2 | — | Ph | —OCH₂— | Ph | F<br>\|<br>OCH₂*CHC₆H₁₃ |
| 2-193 | 2 | 2 | 8 | 2 | —O— | Ph | — | Tz1 | — | — | CF₃<br>\|<br>(CH₂)₂*CHC₈H₁₇ |
| 2-194 | 3 | 1 | 8 | 1 | —O— | Ph | — | Bta1 | — | — | CH₃<br>\|<br>O(CH₂)₃*CHC₆H₁₃ |
| 2-195 | 3 | 1 | 8 | 1 | —OCO— | Ph | — | Pd | — | Ph | F<br>\|<br>OCO*C(CH₃)C₃H₇ |
| 2-196 | 3 | 1 | 8 | 1 | —O— | Py2 | — | Ph | CH₂CH₂ | Id2 | CF₃<br>\|<br>(CH₂)₂*CHC₄H₉ |
| 2-197 | 3 | 1 | 8 | 1 | —O— | Ph | — | Pr2 | — | Ph | CH₃<br>\|<br>OCH₂*CHC₆H₁₃ |
| 2-198 | 4 | 1 | 8 | 1 | —O— | Ph | — | Bob2 | — | Cy | COO—La1(6,0) |
| 2-199 | 4 | 1 | 8 | 1 | —O— | Btb2 | — | Ph | — | — | CH₃<br>\|<br>OCH₂*CHOCOC₃H₇ |
| 2-200 | 4 | 1 | 8 | 1 | —O— | Ph | — | Ph | — | — | OCH₂—Thf |
| 2-201 | 5 | 1 | 8 | 1 | —O— | Ph | — | Pr2 | — | — | F<br>\|<br>OCH₂*CHC₅H₁₁ |
| 2-202 | 5 | 1 | 8 | 1 | —O— | Np | — | — | — | — | CF₃<br>\|<br>O(CH₂)₃*CHC₅H₁₁ |
| 2-203 | 6 | 1 | 8 | 1 | —O— | Ph | — | Tn | — | — | CH₃<br>\|<br>(CH₂)₅*CHC₆H₁₃ |
| 2-204 | 7 | 1 | 8 | 1 | —O— | Cy | — | Ph | —OCO— | Ph | COO—La1(5,0) |
| 2-205 | 1 | 1 | 9 | 1 | — | Ph | — | Tz1 | — | Ph | CF₃<br>\|<br>O(CH₂)₂*CHC₇H₁₅ |
| 2-206 | 1 | 1 | 9 | 1 | —O— | Ph | —C≡C— | Pd | — | — | F<br>\|<br>OCH₂*CHC₃H₇ |
| 2-207 | 1 | 2 | 9 | 2 | —O— | Ph2M | — | Tz1 | — | Ph | OCH₂—Lc2(4,4) |
| 2-208 | 2 | 1 | 9 | 1 | —O— | Ph | — | Py1 | — | — | CH₃<br>\|<br>O(CH₂)₂*CHC₂H₅ |
| 2-209 | 2 | 1 | 9 | 1 | —O— | Ph | — | Ep1 | — | — | CH₃<br>\|<br>OCH₂*CHC₆H₁₃ |
| 2-210 | 2 | 1 | 9 | 2 | —OCO— | Ph | — | Py2 | — | Ph | CF₃<br>\|<br>O(CH₂)₂*CHC₄H₉ |
| 2-211 | 3 | 1 | 9 | 1 | —O— | Ph | — | Btb1 | — | — | CH₃<br>\|<br>O(CH₂)₃*CHC₃H₇ |

-continued

| Ex. Comp. No. | $C_mH_{2m+1}O(CH_2)_n(CF_2)_p(CH_2)_q-Y^1$ | | | | | $A^1$ | | | | | |
|---|---|---|---|---|---|---|---|---|---|---|---|
| | m | n | p | q | $-Y^1-$ | $A^2$ | $X^1$ | $A^3$ | $X^2$ | $A^4$ | $R^1$ |
| 2-212 | 3 | 1 | 9 | 1 | $-O-$ | Ph | — | Ph2CN | — | — | $\underset{OCO*C(CH_3)C_5H_{11}}{\overset{CN}{\mid}}$ |
| 2-213 | 4 | 1 | 9 | 1 | $-O-$ | Ph | $-COO-$ | Ph | — | — | $CH_2O-Lc1(6,0)$ |
| 2-214 | 4 | 1 | 9 | 1 | $-O-$ | Ep2 | — | — | — | — | $\underset{OCH_2*CHC_4H_9}{\overset{F}{\mid}}$ |
| 2-215 | 1 | 1 | 10 | 1 | $-O-$ | Ph | — | Dx1 | — | — | $\underset{(CH_2)_2*CHC_8H_{17}}{\overset{CF_3}{\mid}}$ |
| 2-216 | 2 | 1 | 10 | 1 | $-O-$ | Ph | — | Pr2 | — | — | $\underset{O(CH_2)_2*CHC_6H_{13}}{\overset{CH_3}{\mid}}$ |
| 2-217 | 3 | 1 | 10 | 1 | — | Boa2 | — | Ph | — | — | $OCH_2-Lc2(3,0)$ |
| 2-218 | 4 | 1 | 10 | 1 | $-O-$ | Pr2 | — | Cm2 | — | — | $\underset{CH_2*C(CH_3)C_7H_{15}}{\overset{F}{\mid}}$ |
| 2-219 | 2 | 1 | 11 | 1 | $-O-$ | Ph | — | Ph | — | — | $\underset{OCO*CHC_6H_{13}}{\overset{CF_3}{\mid}}$ |
| 2-220 | 3 | 1 | 11 | 1 | $-O-$ | Ph | — | — | — | — | $\underset{OCH_2*CHC_3H_7}{\overset{F}{\mid}}$ |
| 2-221 | 4 | 1 | 11 | 1 | $-O-$ | Ph | — | Btb1 | — | — | $\underset{O(CH_2)_8*CHC_4H_5}{\overset{CH_3}{\mid}}$ |
| 2-222 | 2 | 1 | 12 | 1 | $-O-$ | Gp2 | — | — | — | — | $\underset{O(CH_2)_2*CHC_5H_{11}}{\overset{CH_3}{\mid}}$ |
| 2-223 | 4 | 1 | 12 | 1 | $-O-$ | Ph | — | Py1 | — | — | $\underset{OCO*CHC_3H_7}{\overset{F}{\mid}}$ |
| 2-224 | 3 | 1 | 13 | 1 | $-O-$ | Ph | — | Tz1 | — | Ph3Br | $OCH_2-Pla$ |
| 2-225 | 2 | 1 | 14 | 1 | $-O-$ | Cy | — | — | — | — | $\underset{COOCH_2*CHC_5H_{11}}{\overset{CF_3}{\mid}}$ |
| 2-226 | 1 | 1 | 15 | 1 | $-OCO-$ | Cy | — | Ph | $-OCH_2-$ | Id2 | $\underset{O(CH_2)_2*CHC_6H_{13}}{\overset{CH_3}{\mid}}$ |
| 2-227 | 1 | 1 | 16 | 1 | $-O-$ | Ph | — | Ph2F | — | — | $\underset{OCH_2*C(CH_3)C_2H_5}{\overset{CN}{\mid}}$ |
| 2-228 | 4 | 1 | 3 | 1 | $-O-$ | Ph | — | Py1 | — | — | $OCH_2-Lc1(0,0)$ |
| 2-229 | 3 | 2 | 4 | 2 | $-O-$ | Ph | — | Ph | — | — | $OCH_2-La2(0,0)$ |
| 2-230 | 4 | 1 | 4 | 1 | $-O-$ | Py2 | — | Ph | — | — | $\underset{O(CH_2)_2*CHOCOC_6H_{13}}{\overset{CH_3}{\mid}}$ |
| 2-231 | 5 | 1 | 3 | 1 | $-O-$ | Py2 | — | Ph | — | — | $\underset{O(CH_2)_3*CHC_3H_7}{\overset{F}{\mid}}$ |

The liquid crystal composition according to the present invention may be obtained by mixing at least one species of the mesomorphic compound represented by the formula (I) and at least one species, preferably 1–50 species, more preferably 1–30 species, particularly 3–30 species, of another mesomorphic compound, in appropriate proportions determined by taking account of usage or uses of a liquid crystal device using the composition, characteristics required therefor, etc.

The liquid crystal composition according to the present invention may preferably be formulated as a liquid crystal composition capable of showing ferroelectricity, particularly a liquid crystal composition showing a chiral smectic phase.

Specific examples of another mesomorphic compound described above may include those disclosed in, e.g., Japanese Laid-Open Patent Application (JP-A) 4-272989. More specifically, on pages 23–39 of JP-A 4-272989, the following mesomorphic compounds are disclosed as another mesomorphic compound.

Formulae (III) and (IV): pyrimidine ring-based mesomorphic compound,

Formula (V): benzene ring-based mesomorphic compound,

Formula (VI): benzene ring- or cyclohexane ring-based mesomorphic compound,

Formula (VII): naphthalene ring-based mesomorphic compound,

Formula (VIII): pyrazine ring-based mesomorphic compound,

Formula (IX): pyridazine ring-based mesomorphic compound,

Formula (X) and (XI): pyridine ring-based mesomorphic compound, and

Formula (XII): thiadiazole ring-based mesomorphic compound.

Further, JP-A 4-272989 disclosed preferred mesomorphic compounds of the formulae (IIIa) to (XIId) and particularly preferred mesomorphic compounds of the formulae (IIIaa) to (XIIdb).

In the above mesomorphic compounds of the formulae (III) to (XII), (IIIa) to (XIId) and (IIIaa) to (XIIdb), at least one terminal group (i.e., $R_1'$ and/or $R_2'$, $R_3'$ and/or $R_4'$, or $R_5'$ and/or $R_6'$) may be the group:

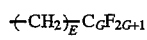

in which E is an integer of 0–10 and G is an integer of 1–15.

In the present invention, mesomorphic compounds represented by the following formulae (XIII) to (XVIII) may also be used as another mesomorphic compound.

Specific examples of another mesomorphic compound may also include those represented by the following formulae (XIII) to (XVIII) including abbreviations for respective cyclic groups listed below in addition to those described above.

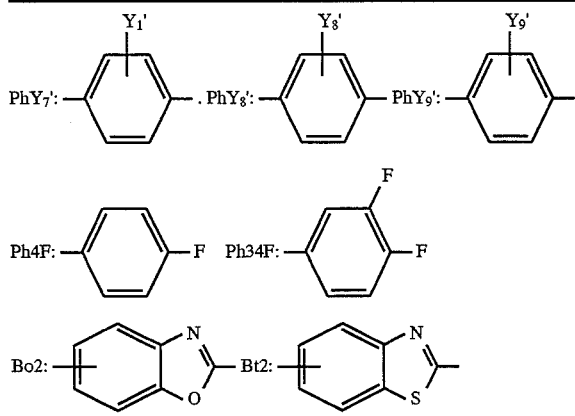

| | |
|---|---|
| $R_7'-(Py2)-X_7'-(Ph)-X_8'-(PhY_7')_N-(Tn)-R_8'$ | (XIII) |
| $R_7'-(Py2)-(Ph)-OCO-(Ph4F)$ | (XIV) |
| $R_7'-(Py2)-(Ph)-OCO-(Ph34F)$ | (XV) |
| $R_7'-(PhY_7')_Q-(Tz1)-(PhY_8')-X_7'-(PhY_9')_R-(Cy)_T-R_8'$ | (XVI) |
| $R_7'-(Bo2)-A_4'-R_8'$ | (XVII) |
| $R_7'-(Bt2)-A_4'-R_8'$ | (XVIII) |

Herein, $R_7'$ and $R_8'$ respectively denote hydrogen or a linear or branched alkyl group having 1–18 carbon atoms capable of including one or non-neighboring two or more methylene groups which can be replaced with —O—, —CO—, —CH(CN)— or —CCH$_3$(CN)— provided that heteroatoms are not adjacent to each other and capable of including at least one H which can be replaced with F.

Further, preferred examples of $R_7'$ and $R_8'$ may respectively include those represented by the following groups (i) to (viii):

i) a linear alkyl group having 1–15 carbon atoms;

ii)

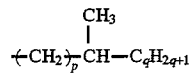

wherein p denotes an integer of 0–5 and q denotes an integer of 2–11 (optically active or inactive);

iii)

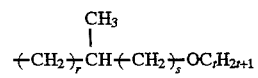

wherein r denotes an integer of 0–6, s denotes 0 or 1, and t denotes an integer of 1–14 (optically active or inactive);

iv)

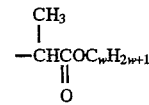

wherein w denotes an integer of 1–15 (optically active or inactive):

v)

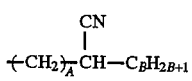

wherein A denotes an integer of 0–2 and B denotes an integer of 1–15 (optically active or inactive);

vi)

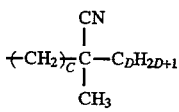

wherein C denotes an integer of 0–2 and D denotes an integer of 1–15 (optically active or inactive);

vii) $-(CH_2)_E-C_GF_{2G+1}$ wherein E is an integer of 0–10 and G is an integer of 1–15; and viii) H (hydrogen).

In the above formulae (XIII) to (XVIII); N, Q, R and T are 0 or 1; $Y_7'$, $Y_8'$ and $Y_9'$ are H or F; $A_4'$ is Ph or Np; and $X_7'$ and $X_8'$ respectively denote a single bond, —COO—, —OCO—, —CH$_2$O— or —OCH$_2$—.

The compound of the formula (XIII) may preferably include a compound represented by the following formula (XIIIa):

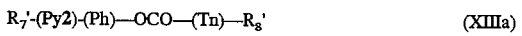  (XIIIa)

The compound of the formula (XVI) may preferably include compounds represented by the following formulae (XVIa) and (XVIb):

 (XVIa), and

 (XVIb).

The compound of the formula (XVII) may preferably include compounds represented by the following formulae (XVIIa) and (XVIIb):

 (XVIIa), and

 (XVIIb).

The compounds of the formula (XVIII) and may preferably include compounds represented by the following formulae (XVIIIa) to (XVIIIc):

 (XVIIIa),

 (XVIIIb), and

 (XVIIIc).

The compounds of the formula (XVIa) and (XVIb) may preferably include compounds represented by the following formulae (XVIa) to (XVIc):

 (XVIaa),

 (XVIba),

 (XVIbb), and

 (XVIbc).

In formulating the liquid crystal composition according to the present invention, the liquid crystal composition may desirably contain 1–80 wt. %, preferably 1–60 wt. %, more preferably 1–40 wt. % of a mesomorphic compound represented by the formula (I) (optically active or inactive).

Further, when two or more species of the mesomorphic compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I) (optically active or inactive).

The liquid crystal device according to the present invention may preferably be prepared by heating the liquid crystal composition as prepared above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity as prepared above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. In the present invention, the transparent electrode 3 may be formed on one of the substrates 2. The glass substrates 2 are placed or arranged opposite each other. Lead wires 6 are connected to the electrodes so as to apply a driving voltage to the liquid crystal layer 1 from a power supply. 7. Outside the substrates 2, a pair of polarizers 8 are disposed so as to modulate incident light $I_O$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to uniaxially align the liquid crystal molecules in the rubbing direction (uniaxial alignment treatment). Further, it is also possible to compose the alignment control layer 4 of two layers, e.g., by first forming an insulating layer of an inorganic material, such as silicon nitride, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer comprising the above-mentioned inorganic material or organic insulating alignment control layer comprising the above-mentioned organic material. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer 4 may have a thickness of ordinarily 10 Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, a sealing material comprising, e.g., an epoxy adhesive. Alternatively, a polymer film or glass fiber may also be used as a spacer. Between the two glass plates, a liquid crystal composition assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, a pair of polarizers 8 arranged in, e.g., right angle cross nicol relationship are applied. The device shown in FIG. 1 is of a transmission type and accordingly is provided with a light source 9 at the back of one of the polarizers 8.

Figure 2:
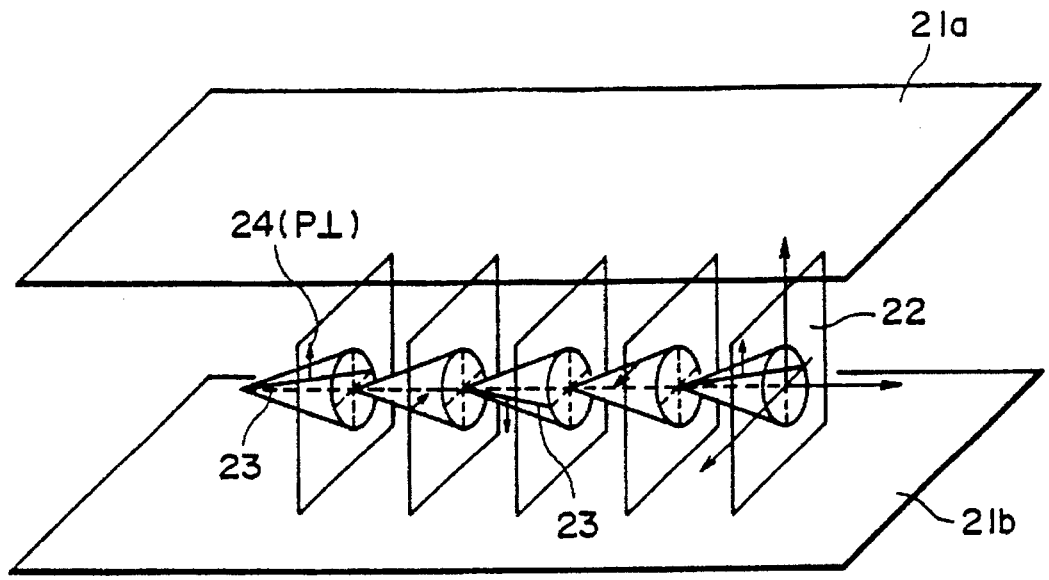
FIGS. 2 and 3 are schematic perspective views of a device cell embodiment for illustrating the operation principle liquid crystal device utilizing ferroelectricity of a liquid crystal composition.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Lines 23 show liquid crystal molecules. Each liquid crystal molecule 23 has a dipole moment ($P_\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments ($P_\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
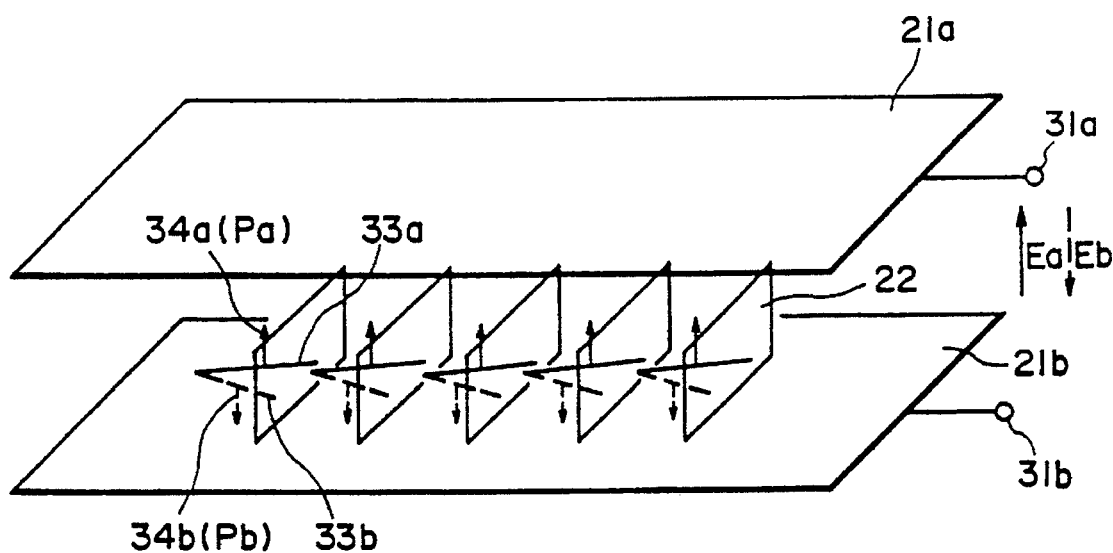

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 5B:
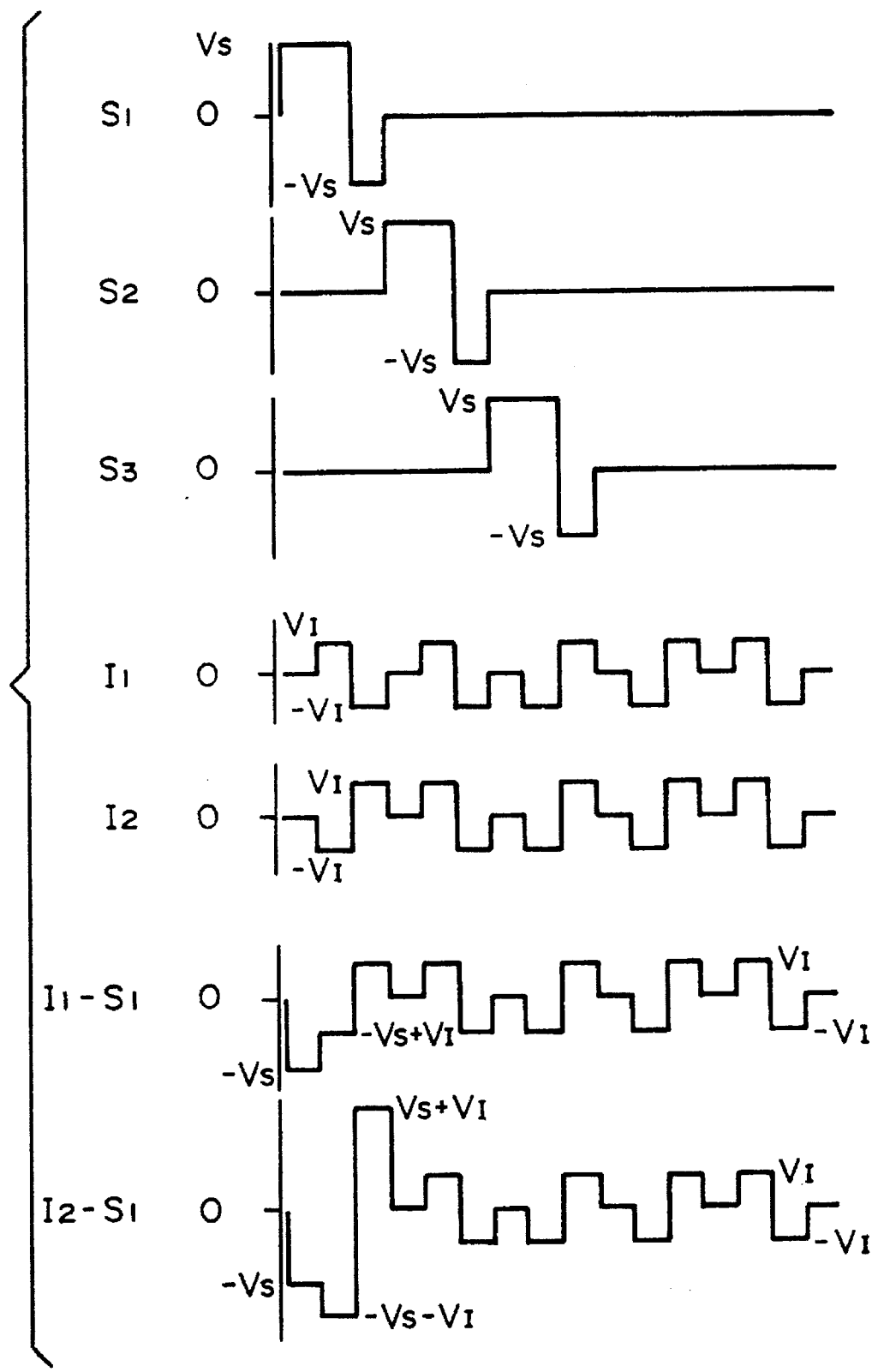
FIG. 5B is time-serial waveforms comprising a succession of such unit waveforms.

FIGS. 5A and 5B are waveform diagrams showing driving voltage waveforms adopted in driving a ferroelectric liquid crystal panel as an embodiment of the liquid crystal device according to the present invention.

Figure 6:
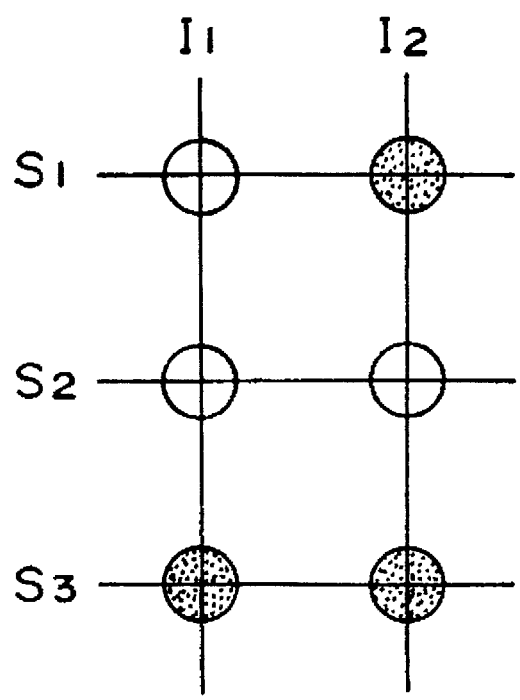
FIG. 6 is an illustration of a display pattern obtained by an actual drive using the time-serial waveforms show in FIG. 5B.

Referring to FIG. 5A, at $S_S$ is shown a selection scanning signal waveform applied to a selected scanning line, at $S_N$ is shown a non-selection scanning signal waveform applied to a non-selected scanning line, at $I_S$ is shown a selection data signal waveform (providing a black display state) applied to a selected data line, and at $I_N$ is shown a non-selection data signal waveform (providing a white display state) applied to a non-selected data line. Further, at ($I_S$–$S_S$) and ($I_N$–$S_S$) in the figure are shown voltage waveforms applied to pixels on a selected scanning line, whereby a pixel supplied with the voltage ($I_S$–$S_S$) assumes a black display state and a pixel supplied with the voltage ($I_N$–$S_S$) assumes a white display state. FIG. 5B shows a time-serial waveform used for providing a display state as shown in FIG. 6.

In the driving embodiment shown in FIGS. 5A and 5B, a minimum duration Δt of a single polarity voltage applied to a pixel on a selected scanning line corresponds to the period of a writing phase $t_2$, and the period of a one-line clearing phase $t_1$ is set to 2 Δt.

The parameters $V_S$, $V_I$ and Δt in the driving waveforms shown in FIGS. 5A and 5B are determined depending on switching characteristics of a ferroelectric liquid crystal material used. In this embodiment, the parameters are fixed at a constant value of a bias ratio $V_I/(V_I+V_S)=\frac{1}{3}$. It is of course possible to increase a range of a driving voltage allowing an appropriate matrix drive by increasing the bias ratio. However, a large bias ratio corresponds to a large amplitude of a data signal and leads to an increase in flickering and a lower contrast, thus being undesirable in respect of image quality. According to our study, a bias ratio of about ⅓¼ was practical.

The liquid crystal device according to the present invention is used as an element, particularly a display element, for various liquid crystal apparatus.

Figure 7:
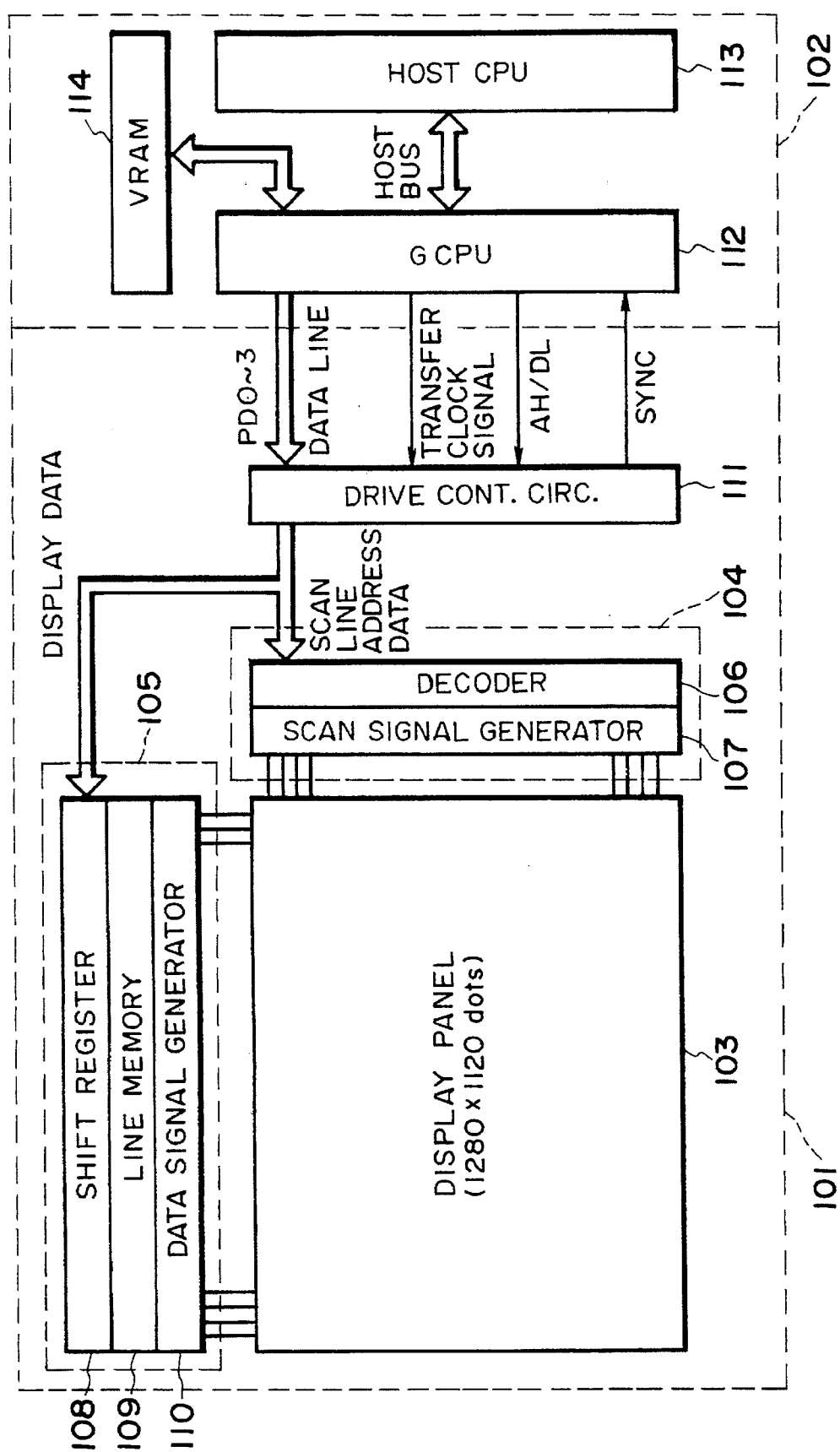
FIG. 7 is block diagram showing a display apparatus comprising liquid crystal device utilizing ferroelectricity of a liquid crystal composition and a graphic controller.
Figure 8:
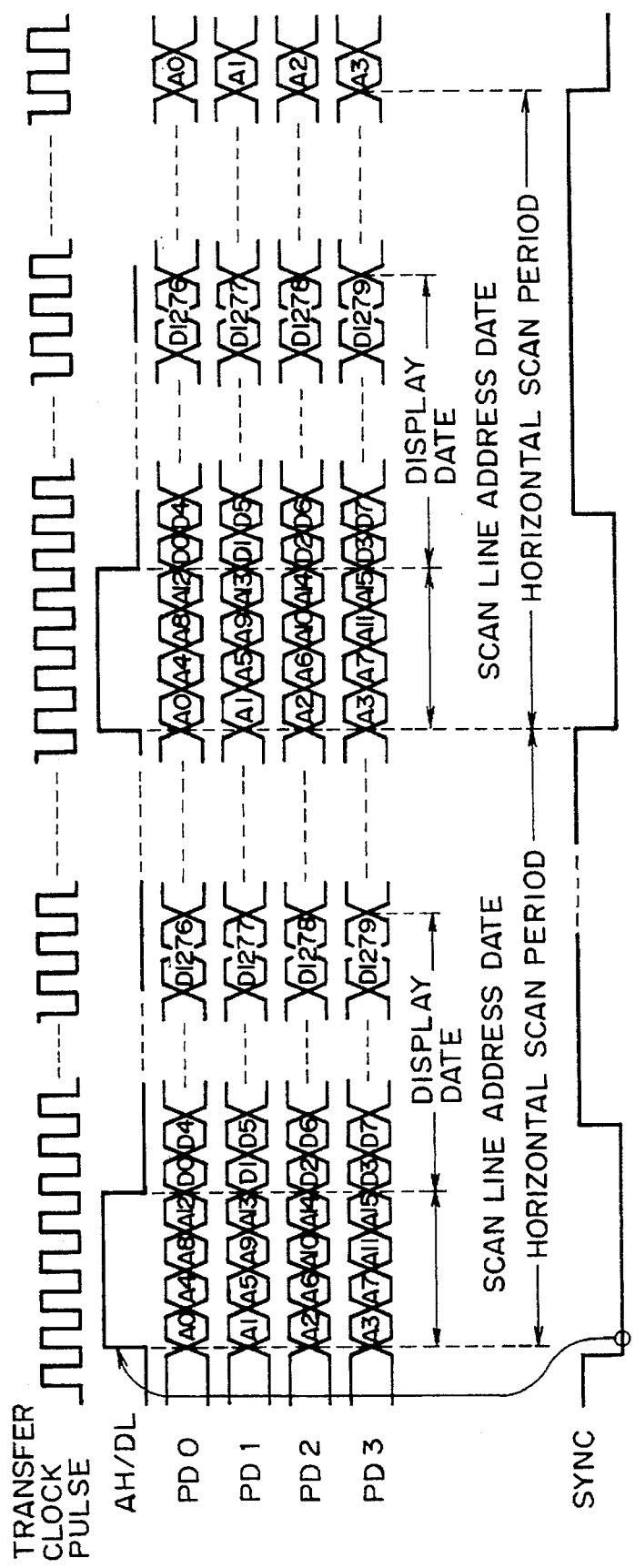
FIG. 8 is time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 7 and 8, there is provided a liquid crystal display apparatus of the present invention which uses the liquid crystal device according to the present invention as a display panel portion.

Referring to FIG. 7, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally performed by the graphic controller 102. A light source (not shown) is disposed at the back of the display panel 103.

Hereinbelow, the present invention will be explained more specifically with reference to examples. It is however to be understood that the present invention is not restricted to these examples.

In the following examples, the respective symbols denote the following phase; Iso: isotropic phase; Ch: cholesteric phase; SmA: smectic A phase; SmC: smectic C phase; SmC*: chiral smectic phase; and Cryst.: crystal.

EXAMPLE 1—1

Production of 2-[4-(6-propoxy-1H,1H,6H,6H-perfluorohexyloxycarbonyl)phenyl]-6-hexylbenzothiazole (Example Compound No. 1-95)

(Step 1)

Production of 6-propoxy-1H,1H,6H,6H-perfluorohexanol

In a 2 liter-three necked flask, 50 g (190.8 mM) of 1H,1H,6H,6H-perfluoro-1,6-hexanediol and 511 ml of N,N-dimethylformamide (DMF) were placed and mutually solved. Under stirring on an ice bath, 7.63 g (190.8 mM) of 60%-sodium hydride in oil was added to the solution in 25 minutes at 6°–10° C. (inner temperature), followed by stirring for 1 hour at 20°–23° C. To the mixture, 32.4 g (190.6 mM) of propyl iodide was added dropwise in 15 minutes at 6°–8° C. under stirring on an ice bath, followed by stirring for 4.5 hours at 35°–40° C. The reaction mixture was left standing overnight, poured into 1.5 liters of water, acidified by 5% hydrochloric acid (pH=1), and subjected to extraction with ether. The organic layer was washed three times with saturated common salt water and dried with anhydrous magnesium sulfate, followed by distilling-off of the solvent to obtain a residue. The residue was purified by silica gel column chromatography (eluent: hexane/ethyl acetate=4/1) to obtain 20.1 g of pale yellow liquid 6-propoxy-1H,1H,6H,6H-perfluorohexanol (Yield: 34.7%).

(Step 2)

Production of 2-[4-(6-propoxy-1H,1H,6H,6H-perfluorohexyloxycarbonyl)phenyl]-6-hexylbenzothiazole 0.3 g (0.88 mM) of 2-(4-carboxyphenyl)-6-hexylbenzothiazole, 0.27 g (0.89 mM) of 6-propoxy-1H,1H,6H,6H-perfluorohexanol, 0.18 g (0.87 mM) of dicyclohexylcarbodiimide (DCC), 0.02 g of 4-dimethylaminopyridine, and 6 ml of dichloromethane were placed in a 50 ml-round bottomed flask and stirred for 24 hours at room temperature. After the reaction, the reaction mixture was filtered to obtain a filtrate. The filtrate was condensed into a crude product. The crude product was purified by silica gel column chromatography (eluent: toluene/ethyl acetate=50/1) and recrystallized from a mixture solvent (toluene/hexane) to obtain 0.30 g of 2-[4-(6-propoxy-1H,6H,6H-perfluorohexyloxycarbonyl)phenyl]-6-hexylbenzothiazole (Yield: 54%; melting point (m.p.): 103.1° C.).

EXAMPLE 1-2

Production of 2-[4-(5-butyloxy-1H,1H,5H,5H-perfluoropentyloxycarbonyl)phenyl]- 5-nonylpyrimidine (Ex. Comp. No. 1-70)

(Step 1)

Production of 5-butyloxy-1H,1H,5H,5H-perfluoropentanol

In a 1 liter-three necked flask, 48.3 g (228 mM) of 1H,1H,5H,5H-perfluoro-1,5-pentanediol and 735 ml of dry DMF were placed. To the mixture, 9.22 g (231 mM) of 60%-sodium hydride in oil was added at 10° C. or below, followed by stirring for 10 minutes at the temperature and stirring for 1 hour at room temperature. The resultant mixture was cooled to 10° C. or below. To the mixture, 31.4 g (229 mM) of n-butyl bromide was added dropwise in 10 minutes, followed by stirring for 6 hours at 35° C. After the reaction, the reaction mixture was poured into 1 liter of water and acidified by diluted hydrochloric acid. The mixture was saturated with common salt and subjected to extraction with ethyl acetate. The organic layer was washed with common salt water and dried with anhydrous magnesium sulfate, followed by distilling-off of the solvent to obtain a residue. The residue was subjected to reduced-pressure distillation (boiling point (b.p.): 86°–98° C./4 torr) and purified by silica gel column chromatography (eluent: hexane/ethyl acetate=4/1) to obtain 32.5 g of 5-butyloxy-1H,1H,5H,5H-perfluoropentanol (Yield: 53%).

(Step 2)

Production of 2-[4-(5-butyloxy-1H,1H,5H,5H-perfluoropentyloxycarbonyl)phenyl]-5-nonylpyrimidine 0.35 g (1.07 mM) of 2-(4-carboxyphenyl)-5-nonylpyrimidine, 0.30 g (1.12 mM) of 5-butyloxy-1H,1H, 5H,5H-perfluoropentanol, 0.22 g (1.07 mM) of DCC, 0.03 g of 4-dimethylaminopyridine, and 8 ml of dichloromethane were placed in a 50 ml-round bottomed flask and stirred for 14 hours at room temperature. After the reaction, the reaction mixture was filtered to obtain a filtrate. The filtrate was condensed into a crude product. The crude product was purified by silica gel column chromatography (eluent: toluene/ethyl acetate=100/1) and recrystallized from a mixture solvent (toluene/methanol) to obtain 0.37 g of 2-[4-(5-butyloxy-1H,1H,5H,5H-perfluoropentyloxycarbonyl) phenyl]-5-nonylpyrimidine (Yield: 66%; m.p.: 65.2° C.).

EXAMPLE 1-3

Production of 5-butyloxy-1H,1H,5H,5H-perfluoropentyl 4-pentyloxy-4'-biphenyl carboxylate (Ex. Comp. No. 1-71)

0.30 g (1.06 mM) of 4-pentyloxy-4'-bipheylcarboxylic acid, 0.30 g (1.12 mM) of 5-butyloxy-1H,1H,5H,5H-perfluoropentanol, 0.22 g (1.07 mM) of DCC, 0.03 g of 4-dimethylaminopyridine, and 8 ml of dichloromethane were placed in a 50 ml-round bottomed flask and stirred for 14 hours at room temperature. After the reaction, the reaction mixture was filtered to obtain a filtrate. The filtrate was condensed into a crude product. The crude product was purified by silica gel column chromatography (eluent: toluene/ethyl acetate=100/1) and recrystallized from a mixture solvent (toluene/methanol) to obtain 0.06 g of 5-butyloxy-1H,1H,5H,5H-perfluoropentyl 4-pentyloxy-4'-biphenyl carboxylate (Yield: 10%).

Phase transition temperature (° C.)

$$\text{Cryst.} \underset{25.1}{\overset{38.4}{\rightleftarrows}} \text{SmA} \underset{44.3}{\overset{45.9}{\rightleftarrows}} \text{Iso.}$$

EXAMPLE 1-4

Production of 2-[4-(5-butyloxy-1H,1H,5H,5H-perfluoropentyloxy)phenyl]-5-decylpyrimidine (Ex. Comp. No. 1-232)

(Step 1)

Production of 5-butyloxy-1H,1H,5H,5H-perfluoropentyl trifluoromethanesulfonate

In a 100 ml-round bottomed flask, 1.34 g (5.0 mM) of 5-butyloxy-1H,1H,5H,5H-perfluoropentanol and 1.19 g (15.0 mM) of pyridine were placed and cooled. To the mixture, 2.82 g (10.0 mM) of trifluoromethanesulfonic anhydride was added dropwise, followed by stirring for 1 hour at room temperature. After the reaction, ice water was added to the reaction mixture and subjected to extraction with ethyl acetate. The extract was washed with 3M-hydrochloric acid and water and dried with anhydrous sodium sulfate, followed by distilling-off of the solvent to obtain 1.78 g (4.45 mM) of 5-butyloxy-1H,1H,5H,5H-perfluoropentyl trifluoromethanesulfonate (Yield: 89%).

(Step 2)

Production of 2-[4-(5-butyloxy-1H,1H,5H,5H-perfluoropentyloxy)phenyl]-5-decylpyrimidine In a 50 ml-round bottomed flask, 0.08 g (2.00 mM) of 60%-sodium hydride and 3 ml of DMF were placed. To the mixture, 0.52 g (1.66 mM) of 5-decyl-2-(4-hydroxyphenyl)pyrimidine was added, followed by stirring for 30 minutes at room temperature. To the resultant mixture, a mixture liquid of 0.66 g (1.66 mM) of 5-butyloxy-1H,1H,5H,5H-perfluoropentyl trifluoromethanesulfonate and 2 ml of DMF was added, followed by stirring for 1 hour at 100° C. After the reaction, water was added to the reaction mixture and subjected to extraction with ethyl acetate. The extract was washed with 3M-hydrochloric acid and water and dried with anhydrous sodium sulfate, followed by distilling-off of the solvent to obtain a crude product. The crude product was purified by silica gel column chromatography (eluent: toluene) and recrystallized from methanol to obtain 0.31 g (0.55 mM) of 2-[4-(5-butyloxy-1H,1H,5H,5H-perfluoropentyloxy)phenyl]-5-decylpyrimidine (Yield: 33%).

Phase transition temperature (° C.)

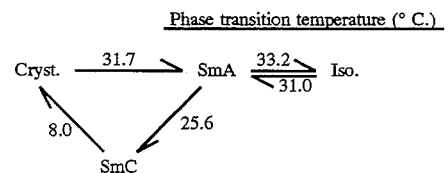

EXAMPLE 1-5

A liquid crystal composition 1-A was prepared by mixing the following compounds in the indicated proportions.

| Structural formula | wt. parts |
| --- | --- |
| $C_9H_{19}$—Py2—Ph—$OC_9H_{19}$ | 6 |
| $C_{10}H_{21}$—Py2—Ph—$OC_8H_{17}$ | 6 |
| $C_8H_{17}O$—Pr1—Ph—$O(CH_2)_5$*$CH(CH_3)C_2H_5$ | 7 |
| $C_{11}H_{23}O$—Py2—Ph—$O(CH_2)_2$*$CH(CH_3)C_2H_5$ | 14 |
| $C_{10}H_{21}$—Pr2—Ph—$C_6H_{13}$ | 8 |
| $C_6H_{13}$—Py2—Ph—Ph—$C_4H_9$ | 4 |
| $C_8H_{17}$—Ph—Pr2—Ph—$OC_5H_{11}$ | 2 |
| $C_3H_7$—Cy—COO—Ph—Py1—$C_{12}H_{25}$ | 10 |
| $C_5H_{11}$—Cy—COO—Ph—Py1—$C_{12}H_{25}$ | 5 |
| $C_{10}H_{21}O$—Ph—COS—Ph—$OC_8H_{17}$ | 10 |
| $C_6H_{13}$—Ph—COO—Ph—Ph—$OCH_2CH(CH_3)C_2H_5$ | 7 |
| $C_3H_7$—Cy—$CH_2O$—Ph—Py1—$C_8H_{17}$ | 7 |
| $C_{10}H_{21}$—Ph—Ph—$OCH_2$—Ph—$C_7H_{15}$ | 5 |
| $C_{12}H_{25}$—Py2—Ph—$OCH_2$*$CH(F)C_5H_{11}$ | 2 |
| $C_5H_{11}$—Cy—COO—Ph—$OCH_2$*$CH(F)C_6H_{13}$ | 2 |
| $C_{12}H_{25}O$—Ph—Pa—COO$(CH_2)_3$*$CH(CH_3)C_2H_5$ | 2 |
| $C_{12}H_{25}O$—Ph—Pa—$O(CH_2)_3$*$CH(CH_3)OC_3H_7$ | 3 |

The liquid crystal composition 1-A was further mixed with the following example compounds in the indicated proportions to provide a liquid crystal composition 1-B.

| Ex. Comp. No. | Structural formula | wt. parts |
| --- | --- | --- |
| 1-3 | $C_2H_5O(CH_2)_2CF_2(CH_2)_2$—O—Ph—Py1—$C_7H_{15}$ | 3 |
| 1-75 | $C_5H_{11}OCH_2(CF_2)_3CH_2$—$OCH_2$—Ph—Pr1—$C_8H_{17}$ | 3 |
|  | Composition 1-A | 94 |

EXAMPLE 1-6

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After silica beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition 1-B prepared in Example 1-5 was heated into an isotropic liquid, and injected into the above prepared cell under vacuum and, after sealing, was gradually cooled to 25° C. at a rate of 20° C./hour to prepare a ferroelectric liquid crystal device. The cell gap was found to be about 2 microns as measured by a Berek compensator.

The ferroelectric liquid crystal device was subjected to measurement of an optical response time (time from voltage application until the transmittance change reaches 90% of the maximum under the application of a peak-to-peak voltage Vpp of 20 V in combination with right-angle cross-nicol polarizers) and observation of switching states. In the device, a monodomain with a good and uniform alignment characteristic was observed. The results of the measurement of response time are shown below.

| | 10° C. | 25° C. | 40° C. |
|---|---|---|---|
| Response time (μsec) | 551 | 295 | 164 |

COMPARATIVE EXAMPLE 1—1

A ferroelectric liquid crystal device was prepared end subjected to measurement of response time in the same manner as in Examples 1–6 except for injecting the composition 1-A prepared in Examples 1–5 into a blank cell, whereby the following results were obtained.

| | 10° C. | 25° C. | 40° C. |
|---|---|---|---|
| Response time (μsec) | 668 | 340 | 182 |

EXAMPLE 1–7

A liquid crystal composition 1-C was prepared by mixing the following Example Compounds instead of those of Examples 1–5 in the indicated proportions with the liquid crystal composition 1-A.

| Ex. Comp. No. | Structural formula | wt. parts |
|---|---|---|
| 1-31 | $C_2H_5O(CH_2)_2(CF_2)_2(CH_2)_2$—O—Ph—$CH_2CH_2$—Ph—$OCH_2C_9F_{19}$ | 3 |
| 1-130 | $C_4H_9OCH_2(CF_2)_5CH_2$—O—Ph—Btb1—$C_5H_{11}$ | 2 |
| | Composition 1-A | 95 |

A ferroelectric liquid crystal device was prepared in the same manner as in Example 1–6 except that the above liquid crystal composition 1-C was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 547 | 293 | 162 |

EXAMPLE 1–8

A liquid crystal composition 1-D was prepared by mixing the following Example Compounds instead of those of Example 1–5 in the indicated proportions with the liquid crystal composition 1-A.

| Ex. Comp. No. | Structural formula | wt. parts |
|---|---|---|
| 1-32 | $C_2H_5O(CH_2)_6(CF_2)_2(CH_2)_6$—O—Ph—Ph3F—$C_6H_{13}$ | 1 |
| 1-95 | $C_3H_7OCH_2(CF_2)_4CH_2$—OCO—Ph—Btb1—$C_6H_{13}$ | 2 |
| 1-127 | $C_3H_7OCH_2(CF_2)_5CH_2$—O—Ph—Id2—$C_{10}H_{21}$ | 3 |
| | Composition 1-A | 94 |

A ferroelectric liquid crystal device was prepared in the same manner as in Example 1–6 except that the above liquid crystal composition 1-D was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 544 | 292 | 162 |

EXAMPLE 1–9

A liquid crystal composition 1-E was prepared by mixing the following compounds in the indicated proportions.

| Structural formula | wt. parts |
|---|---|
| $C_7H_{15}$—Py2—Ph—$OC_9H_{19}$ | 12 |
| $C_{11}H_{23}$—Py2—Ph—$OC_6H_{13}$ | 10 |
| $C_8H_{17}$—Pr2—Ph—$O(CH_2)_5$*$CH(CH_3)C_2H_5$ | 10 |
| $C_{10}H_{21}$—Py2—Ph—$O(CH_2)_4CH(CH_3)OCH_3$ | 3 |

-continued

| Structural formula | wt. parts |
|---|---|
| $C_8H_{17}$—Py2—Ph—Ph—$OC_6H_{13}$ | 8 |
| $C_6H_{13}$O—Ph—OCO—Np—$OC_9H_{19}$ | 4 |
| $C_3H_7$—Cy—COO—Ph—Py1—$C_{11}H_{23}$ | 6 |
| $C_8H_{17}$—Cy—COO—Ph—Py1—$C_{11}H_{23}$ | 2 |
| $C_5H_{11}$—Cy—COO—Ph—Py1—$C_{11}H_{23}$ | 8 |
| $C_{10}H_{21}$O—Ph—COO—Ph—$OCH_2$*$CH(CH_3)C_2H_5$ | 15 |
| $C_4H_9$—Cy—$CH_2$O—Ph—Py1—$C_6H_{13}$ | 7 |
| $C_5H_{11}$—Cy—$CH_2$O—Ph—Py1—$C_6H_{13}$ | 7 |
| $C_9H_{19}$O—Ph—$OCH_2$—Ph—Ph—$C_7H_{15}$ | 4 |
| $C_6H_{13}$*$CH(CH_3)$O—Ph—COO—Ph—Ph—OCO*$CH(CH_3)OC_4H_9$ | 2 |
| $C_{12}H_{25}$—Py2—Ph—OCO*CH(Cl)*$CH(CH_3)C_2H_5$ | 2 |

The liquid crystal composition 1-E was further mixed with the following compounds in the proportions indicated below to provide a liquid crystal composition 1-F.

| Ex. Comp. No. | Structural formula | wt. parts |
| --- | --- | --- |
| 1-53 | $C_8H_{17}OCH_2(CF_2)_2(CH_2)_5$—O—Ph—Ph—OCO—Ph2TF—$C_4H_9$ | 2 |
| 1-80 | $C_7H_{15}OCH_2(CF_2)_3CH_2$—O—Pr2—Ph—OCO—Tn—$C_4H_9$ | 1 |
| 1-117 | $C_9H_{19}OCH_2(CF_2)_4(CH_2)_3$—O—Ph—Tz1—Ph—$C_5H_{11}$ | 3 |
| | Composition 1-E | 94 |

A ferroelectric liquid crystal device was prepared in the same manner as in Example 1–6 except that the above liquid crystal composition 1-F was used, and the device was subjected to measurement of optical response time. The results are shown below.

| | 10° C. | 25° C. | 40° C. |
| --- | --- | --- | --- |
| Response time (μsec) | 601 | 310 | 168 |

COMPARATIVE EXAMPLE 1-2

A ferroelectric liquid crystal device was prepared and subjected to measurement of response time in the same manner as in Example 1–6 except for injecting the composition 1-E alone used in Example 1–9 into a blank cell, whereby the following results were obtained.

| | 10° C. | 25° C. | 40° C. |
| --- | --- | --- | --- |
| Response time (μsec) | 784 | 373 | 197 |

EXAMPLE 1-10

A liquid crystal composition 1-G was prepared by mixing the following Example Compounds instead of those of Example 1–9 in the indicated proportions with the liquid crystal composition 1-E.

| Ex. Comp. No. | Structural formula | wt. parts |
| --- | --- | --- |
| 1-28 | $CH_3O(CH_2)_2(CF_2)_2(CH_2)_2$—O—Py2—Ph—OCO—Cy—$C_6H_{13}$ | 1 |
| 1-63 | $C_2H_5OCH_2(CF_2)_3CH_2$—O—Py2—Ph—OCO—Tn—$C_3H_7$ | 2 |
| 1-193 | $C_2H_5O(CH_2)_2(CF_2)_8(CH_2)_2$—O—Ph—Tz1—$C_6H_{13}$ | 2 |
| | Composition 1-E | 95 |

A ferroelectric liquid crystal device was prepared in the same manner as in Example 1–6 except that the above liquid crystal composition 1-G was used, and the device was subjected to measurement of optical response time and observation of switching states. In the device, a monodomain with a good and uniform alignment characteristic was observed. The results of the measurement are shown below.

| | 10° C. | 25° C. | 40° C. |
| --- | --- | --- | --- |
| Response time (μsec) | 610 | 321 | 177 |

EXAMPLE 1-11

A liquid crystal composition 1-H was prepared by mixing the following Example Compounds instead of those of Example 1–9 in the indicated proportions with the liquid crystal composition 1-E.

| Ex. Comp. No. | Structural formula | wt. parts |
| --- | --- | --- |
| 1-110 | $C_6H_{13}OCH_2(CF_2)_4CH_2$—O—Ph—C≡C—Ph—$C_{10}H_{21}$ | 3 |
| 1-202 | $C_5H_{11}OCH_2(CF_2)_8CH_2$—O—Np—$OC_5H_{11}$ | 3 |
| | Composition 1-E | 94 |

A ferroelectric liquid crystal device was prepared in the same manner as in Example 1–6 except that the above liquid crystal composition 1-H was used, and the device was subjected to measurement of optical response time and observation of switching states. In the device, a monodomain with a good and uniform alignment characteristic was observed. The results of the measurement are shown below.

| | 10° C. | 25° C. | 40° C. |
| --- | --- | --- | --- |
| Response time (μsec) | 604 | 313 | 172 |

EXAMPLE 1-12

A liquid crystal composition 1-I was prepared by mixing the following compounds in the indicated proportions.

| Structural formula | wt. parts |
| --- | --- |
| $C_8H_{17}$—Py2—Ph—$OC_6H_{13}$ | 10 |
| $C_8H_{17}$—Py2—Ph—$OC_9H_{19}$ | 5 |
| $C_{10}H_{21}$—Py2—Ph—$OCOC_8H_{17}$ | 7 |
| $C_{10}H_{21}$—Py2—Ph—$O(CH_2)_3CH(CH_3)OC_3H_7$ | 7 |
| $C_{12}H_{25}$—Py2—Ph—$O(CH_2)_4CH(CH_3)OCH_3$ | 6 |
| $C_5H_{11}$—Py2—Ph—Ph—$C_6H_{13}$ | 5 |
| $C_7H_{15}$—Py2—Ph—Ph—$C_6H_{13}$ | 5 |
| $C_4H_9$—Cy—COO—Ph—Py1—$C_{12}H_{25}$ | 8 |
| $C_3H_7$—Cy—COO—Ph—Py1—$C_{10}H_{21}$ | 8 |
| $C_9H_{19}O$—Ph—COO—Ph—$OC_5H_{11}$ | 20 |
| $C_8H_{17}$—Ph—COO—Ph—Ph—$OCH_2CH(CH_3)C_2H_5$ | 5 |
| $C_8H_{17}$—Ph—OCO—Ph—Ph—*$CH(CH_3)OCOC_6H_{13}$ | 5 |
| $C_6H_{13}$—Ph—$OCH_2$—Ph—Ph—$C_7H_{15}$ | 6 |
| $C_{12}H_{25}$—Py2—Ph—$OCH_2$*$CH(F)C_6H_{13}$ | 3 |

The liquid crystal composition 1-I was further mixed with the following compounds in the proportions indicated below to provide a liquid crystal composition 1-J.

| Ex. Comp. No. | Structural formula | wt. parts |
|---|---|---|
| 1-21 | $C_{11}H_{23}OCH_2CF_2CH_2$—O—Py2—Cm2—$C_6H_{13}$ | 3 |
| 1-78 | $C_7H_{15}OCH_2(CF_2)_3CH_2$—O—Py2—Boa2—Ph—$C_9H_{19}$ | 1 |
| 1-170 | $CH_3O(CH_2)_2(CF_2)_7(CH_2)_2$—Ph—Btb1—$C_6H_{13}$ | 2 |
| | Composition 1-I | 94 |

A ferroelectric liquid crystal device was prepared in the same manner as in Example 1–6 except that the above liquid crystal composition 1-J was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 509 | 257 | 133 |

A ferroelectric liquid crystal device was prepared in the same manner as in Example 1–6 except that the above liquid crystal composition 1-K was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 518 | 262 | 136 |

EXAMPLE 1–14

A liquid crystal composition 1-L was prepared by mixing the following Example Compounds instead of those of Example 1–12 in the indicated proportions with the liquid crystal composition 1-I.

| Ex. Comp. No. | Structural formula | wt. parts |
|---|---|---|
| 1-33 | $C_3H_7OCH_2(CF_2)_2CH_2$—Ph—Py2—$C_8H_{17}$ | 1 |
| 1-40 | $C_4H_9O(CH_2)_2(CF_2)_2(CH_2)_2$—Ph—$CH_2O$—Ph—$OCH(CH_3)CH_2OC_3H_7$ | 3 |
| 1-131 | $C_4H_9OCH_2(CF_2)_5CH_2$—O—Ph—Ep1—$C_{13}H_{27}$ | 1 |
| | Composition 1-I | 95 |

COMPARATIVE EXAMPLE 1–3

A ferroelectric liquid crystal device was prepared and subjected to measurement of response time in the same manner as in Example 1–6 except for injecting the composition 1-I alone used in Example 1–12 into the cell, whereby the following results were obtained.

| | 10° C. | 25° C. | 40° C. |
|---|---|---|---|
| Response time (μsec) | 653 | 317 | 159 |

EXAMPLE 1–13

A liquid crystal composition 1-K was prepared by mixing the following Example Compounds instead of those of Example 1–12 in the indicated proportions with the liquid crystal composition 1-I.

| Ex. Comp. No. | Structural formula | wt. parts |
|---|---|---|
| 1-45 | $C_5H_{11}O(CH_2)_3(CF_2)_2(CH_2)_4$—O—Ph—Ph—Py1—$C_6H_{13}$ | 3 |
| 1-145 | $C_9H_{19}OCH_2(CF_2)_5CH_2$—COO—Ph—Gp2—$C_6H_{13}$ | 2 |
| 1-215 | $CH_3OCH_2(CF_2)_{10}CH_2$—O—Ph—Dx1—$C_6H_{13}$ | 1 |
| | Composition 1-I | 94 |

A ferroelectric liquid crystal device was prepared in the same manner as in Example 1–6 except that the above liquid crystal composition 1-L was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 498 | 254 | 132 |

As apparent from the above Example 1–5 to 1–14, the ferroelectric liquid crystal device including the liquid crystal compositions 1-B, 1-C, 1-D, 1-F, 1-G, 1-H, 1-J, 1-K, and 1-L i.e., compositions containing a mesomorphic compound of the formula (I) according to the present invention, provided improved operation characteristic at a lower temperature, high speed responsiveness and a decreased temperature dependence of response speed.

EXAMPLE 1-15

A blank cell was prepared in the same manner as in Example 1-6 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition 1-8 used in Example 1-5. The liquid crystal device was subjected to measurement of response time in the same manner as in Example 1-6. The results are shown below.

|  | 10° C. | 25° C. | 40° C. |
|---|---|---|---|
| Response time (μsec) | 550 | 294 | 164 |

EXAMPLE 1-16

A blank cell was prepared in the same manner as in Example 1-6 except for omitting the $SiO_2$ layer to form an alignment control layer composed of the polyimide resin layer alone on each electrode plate. A ferroelectric liquid crystal device was prepared by filling such a blank cell with liquid crystal composition 1-B used in Example 1-5. The liquid crystal device was subjected to measurement of response time in the same manner as in Example 1-6. The results are shown below.

|  | 10° C. | 25° C. | 40° C. |
|---|---|---|---|
| Response time (μsec) | 540 | 288 | 160 |

As is apparent from the above Example 1-15 and 1-16, also in the case of a different device structure, the device containing the ferroelectric liquid crystal composition 1-B according to the present invention provided an improved low-temperature operation characteristic and a decreased temperature dependence of response speed similarly as in Examples 1-6.

EXAMPLE 1-17

A liquid crystal composition 1-M was prepared by mixing the following compounds in the indicated proportions.

| Structural formula | wt. parts |
|---|---|
| $C_6H_{13}$—Py2—Ph—O $(CH_2)_4C_3F_7$ | 5 |
| $C_{11}H_{23}$—Py2—Ph—$OCH_2C_4F_9$ | 10 |
| $C_8H_{17}O$—Prl—Ph—O $(CH_2)_5CH(CH_3) C_2H_5$ | 5 |
| $C_{10}H_{21}$—Py2—Ph—O $(CH_2)_4CH(CH_3) OCH_3$ | 10 |
| $C_6H_{13}$—Py2—Ph—Ph—$C_8H_{17}$ | 7 |
| $C_8H_{17}$—Py2—Ph—$OC_6H_{13}$ | 15 |
| $C_5H_{11}$—Cy—COO—Ph—Pyl—$C_{12}H_{25}$ | 5 |
| $C_4H_9$—Cy—COO—Ph—Pyl—$C_{11}H_{23}$ | 5 |
| $C_3H_7$—Cy—COO—Ph—Pyl—$C_{11}H_{23}$ | 5 |
| $C_{12}H_{25}O$—Ph—Pa—CO $(CH_2)_3$*CH $(CH_3) C_2H_5$ | 2 |
| $C_{10}H_{21}$—Py2—Ph—$OCH_2$*CH (F) $C_2H_5$ | 5 |
| $C_6H_{13}$—Cy—COO—Ph—$OCH_2$*CH (F) $C_6H_{13}$ | 2 |
| $C_8H_{17}$—Ph—OCO—Ph—Ph—CH $(CH_3)$ $OCOC_6H_{13}$ | 6 |
| $C_8H_{17}$—Py2—Ph—OCO—Ph—F | 2 |
| $C_7H_{15}O$—Ph—Tzl—Ph—$C_5H_{11}$ | 3 |
| $C_6H_{13}O$—Btb2—Ph—OCO $(CH_2)_6C_2F_5$ | 3 |
| $C_8H_{17}O$—Ph—COS—Ph—$OCH_2C_3F_7$ | 10 |

The liquid crystal composition 1-M was further mixed with the following example compounds in the indicated proportions to provide a liquid crystal composition 1-N.

| Ex. Comp. No. | Structural formula | wt. parts |
|---|---|---|
| 1-7 | $C_4H_9OCH_2CF_2CH_2O$—Ph—COO—Ph2F—$C_7H_{15}$ | 3 |
| 1-104 | $C_5H_{11}OCH_2 (CF_2)_4CH_2O$—Py2—Io2—$C_8H_{17}$ | 3 |
| | Compositoin 1-M | 94 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.0%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 120 Å-thick film.. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 1.5 microns as measured by a Berek compensator.

Then, the liquid crystal composition 1-N prepared above was heated into an isotropic liquid, and injected into the above prepared cell under vacuum and, after sealing, was gradually cooled to 25° C. at a rate of 20° C./hour to prepare a ferroelectric liquid crystal device.

The ferroelectric liquid crystal device was subjected to measurement of a contrast ratio at 30° C. when the device was driven by applying a driving voltage waveform shown in FIGS. 5A and 5B (bias ratio=⅓), whereby a contrast ratio at 30° C. of 19.1 was obtained.

COMPARATIVE EXAMPLE 1-4

A ferroelectric liquid crystal device was prepared and subjected to measurement of a contrast ratio in the same manner as in Example 1-17 except for injecting the composition 1-M alone used in Examples 1-17 into a blank cell, whereby a contrast ratio of 8.1 was obtained.

Example 1-18

A liquid crystal composition 1-O was prepared by mixing the following Example Compounds instead of those of Example 1-17 in the indicated proportions with the liquid crystal composition 1-M.

| Ex. Comp. No. | Structural formula | wt. parts |
| --- | --- | --- |
| 1-46 | $C_6H_{13}OCH_2(CF_2)_2O$—Py2—Ph—$CH_2CH_2$—Cy—$C_7H_{15}$ | 2 |
| 1-93 | $C_2H_5OCH_2(CF_2)_4CH_2O$—Ph—Gpl—$C_{11}H_{23}$ | 2 |
| 1-228 | $C_4H_5OCH_2(CF_2)_3CH_2O$—Ph—Pyl—$OCH_2(CF_2)_4CH_2OCH_3$ | 3 |
| | Composition 1-M | 93 |

A ferroelectric liquid crystal device was prepared in the same manner as in Example 1-17 except that the above liquid crystal composition 1-O was used, and the device was subjected to measurement of a contrast ratio, whereby a contrast ratio of 25.4 was obtained.

EXAMPLE 1-19

A liquid crystal composition 1-P was prepared by mixing the following Example Compounds instead of those of Example 1-17 in the indicated proportions with the liquid crystal composition 1-M.

| Ex. Comp. No. | Structural formula | wt. parts |
| --- | --- | --- |
| 1-56 | $C_9H_{19}OCH_2(CF_2)_2CH_2O$—Ep2—$OCOC_6H_{13}$ | 2 |
| 1-92 | $C_2H_5OCH_2(CF_2)_4CH_2O$—Cy—Ph—OCO—Id2—$C_5H_{11}$ | 2 |
| 1-128 | $C_3H_7O(CH_2)_2(CF_2)_5(CH_2)_2O$—Ph—Prl—$OCH_2CH(CH_3)OC_4H_9$ | 3 |
| | Composition 1-M | 93 |

A ferroelectric liquid crystal device was prepared in the same manner as in Example 1-17 except that the above liquid crystal composition 1-P was used, and the device was subjected to measurement of a contrast ratio, whereby a contrast ratio of 22.1 was obtained.

EXAMPLE 1-20

A liquid crystal composition 1-Q was prepared by mixing the following Example Compounds instead of those of Example 1-17 in the indicated proportions with the liquid crystal composition 1-M.

| Ex. Comp. No. | Structural formula | wt. parts |
| --- | --- | --- |
| 1-181 | $C_5H_{11}OCH_2(CF_2)_7CH_2O$—Ph—Pa—$C_9H_{19}$ | 3 |
| 1-187 | $CH_3OCH_2(CF_2)_8CH_2O$—Ph—Td—$C_9H_{19}$ | 2 |
| 1-195 | $C_3H_7OCH_2(CF_2)_8CH_2OCO$—Ph—Pd—Ph—$C_{12}H_{25}$ | 2 |
| | Composition 1-M | 93 |

A ferroelectric liquid crystal device was prepared in the same manner as in Example 1-17 except that the above liquid crystal composition 1-Q was used, and the device was subjected to measurement of a contrast ratio, whereby a contrast ratio of 21.9 was obtained.

As apparent from the above Example 1-17 to 1-20, the ferroelectric liquid crystal device including the liquid crystal compositions 1-N, 1-O, 1-P and 1-Q, i.e., compositions containing a mesomorphic compound of the formula (I) according to the present invention, provided improved a higher contrast ratio when driven.

EXAMPLE 1-21

A blank cell was prepared in the same manner as in Example 1-17 by using a 2% aqueous solution of polyvinyl alcohol resin (PVA-117, available from Kuraray K.K.) instead of the 1.0%-solution of polyimide resin precursor in dimethylacetoamide on each electrode plate. A ferroelectric liquid crystal device was prepared by filling the blank cell with the liquid crystal composition 1-N used in Example 1-17. The liquid crystal device was subjected to measurement of a contrast ratio in the same manner as in Examples 1-17, whereby a contrast ratio of 23.7 was obtained.

EXAMPLE 1-22

A blank cell was prepared in the same manner as in Example 1-17 except for omitting the $SiO_2$ layer to form an alignment control layer composed of the polyimide resin layer alone on each electrode plate. A ferroelectric liquid crystal device was prepared by filling such a blank cell with liquid crystal composition 1-N used in Example 1-17. The liquid crystal device was subjected to measurement of response time in the same manner as in Example 1-17, whereby a contrast ratio of 18.0 was obtained.

EXAMPLE 1-23

A blank cell was prepared in the same manner as in Example 1-17 except that a 1.0%-solution of polyamide acid (LQ-1802, available from Hitachi Kasei K.K.) in NMP (N-methylpyrrolidone) was used instead of the 1.0%-solution of polyimide resin precursor in dimethylacetoamide on each electrode plate and that the hot curing treatment thereof was effected at 270° C. for 1 hour. A ferroelectric liquid crystal device was prepared by filling the blank cell with the liquid crystal composition 1-N used in Example 1-17. The liquid crystal device was subjected to measurement of a contrast ratio in the same manner as in Example 1-17, whereby a contrast ratio of 35.0 was obtained.

As is apparent from the above Examples 1-21, 1-22 and 1-23, also in the case of a different device structure, the device containing the ferroelectric liquid crystal composition 1-N according to the present invention provided a higher contrast ratio similarly as in Example 1-17.

Further, when a driving voltage waveform different from that used in Example 1-17, a liquid crystal device using the liquid crystal composition according to the present invention provided a higher contrast ratio compared with a liquid crystal device using a liquid crystal composition containing no mesomorphic compound of the formula (I) of the present invention.

EXAMPLE 2-1

Production of optically active 4-(4-methylhexyl)-4'-(6-propoxy-1H,1H,6H,6H-perfluorohexyloxycarbonyl) oxycarbonyl)biphenyl (Ex. Comp. No. 2-3)

(Step 1)

Production of 6-propoxy-1H,1H,6H,6H-perfluorohexanol

In a 2 liter-three necked flask, 50 g (190.8 mM) of 1H,1H,6H,6H-perfluoro-1,6-hexyanediol and 511 ml of N,N-dimethylformamide (DMF) were placed and mutually solved. Under stirring on an ice bath, 7.63 g (190.8 mM) of 60%-sodium hydride in oil was added to the solution in 25 minutes at 6°–10° C. (inner temperature), followed by stirring for 1 hour at 20°–23° C. To the mixture, 32.4 g (190.6 mM) of propyl iodide was added dropwise in 15 minutes at 6°–8° C. under stirring on an ice bath, followed by stirring for 4.5 hours at 35°–40° C. The reaction mixture was left standing overnight, poured into 1.5 liters of water, acidified by 5% hydrochloric acid (pH=1), and subjected to extraction with ether. The organic layer was washed three times with saturated common salt water and dried with anhydrous magnesium sulfate, followed by distilling-off of the solvent to obtain a residue. The residue was purified by silica gel column chromatography (eluent: hexane/ethyl acetate=4/1) to obtain 20.1 g of pale yellow liquid 6-propoxy-1H,1H,6H,6H-perfluorohexanol (Yield: 34.7%).

(Step 2)

Production of optically active 4-(4-methylhexyl)-4'-(6-propoxy-1H,1H,6H,6H-perfluorohexyloxycarbonyl)biphenyl 0.26 g (0.88 mM) of optically active 4-(4-methylhexyl)biphenyl-4'-carboxylic acid, 0.27 g (0.89 mM) of 6-propoxy-1H,1H,6H,6H-perfluorohexanol and 6 ml of dichloromethane was placed in a 30 ml-round bottomed flask. To the mixture under stirring at room temperature, 0.18 g (0.87 mM) DCC and 0.02 g of 4-dimethylaminopyridine was successively added stirred for 2 hours at room temperature and left standing overnight. Then, a resulting N,N'-dicyclohexylurea was filtered off to obtain a filtrate. The filtrate was condensed under reduced pressure into a residue. The residue was purified by silica gel column chromatography (eluent: toluene/ethyl acetate=100/1) to obtain 0.35 g of oil optically active 4-(4-methylhexyl)-4'-(6-propoxy-1H,1H,6H,6H-perfluorohexyloxycarbonyl)biphenyl (Yield: 68.5%).

Phase transition temperature (° C.)

Cryst. ⇌(24.9/−6.4) Iso.

EXAMPLE 2—2

Production of optically active 4-(2-pentyloxypropoxy)-4'-(6-butyloxy-1H,1H,5H,5H-perfluoropentyloxycarbonyl)biphenyl (Ex. Comp. No. 2–97)

(Step 1)

Production of 5-butyloxy-1H,1H,5H,5H-perfluoropentanol

In a 1 liter-three necked flask, 48.3 g (228 mM) of 1H,1H,5H,5H-perfluoro-1,5-pentanediol and 735 ml of dry DMF were placed. To the mixture, 9.22 g (231 mM) of 60%-sodium hydride in oil was added at 10° C. or below, followed by stirring for 10 minutes at the temperature and stirring for 1 hour at room temperature. The resultant mixture was cooled to 10° C. or below. To the mixture, 31.4 g (229 mM) of n-butyl bromide was added dropwise in 10 minutes, followed by stirring for 6 hours at 35° C. After the reaction, the reaction mixture was poured into 1 liter of water and acidified by diluted hydrochloric acid. The mixture was saturated with common salt and subjected to extraction with ethyl acetate. The organic layer was washed with common salt water and dried with anhydrous magnesium sulfate, followed by distilling-off of the solvent to obtain a residue. The residue was subjected to reduced-pressure distillation (boiling point (b.p.): 86°–98° C./532 Pa) and purified by silica gel column chromatography (eluent: hexane/ethyl acetate=4/1) to obtain 32.5 g of 5-butyloxy-1H,1H,5H,5H-perfluoropentanol (Yield: 53%).

(Step 2)

Production of optically active 4-(2-pentyloxypropoxy)-4'-(6-butyloxy-1H,1H,5H,5H-perfluoropentyloxycarbonyl)biphenyl 0.16 g of oily optically active 4-(2-pentyloxypropoxy)-4'-(6-butyloxy-1H,1H,5H,5H-perfluoropentyloxycarbonyl)biphenyl was prepared in the same manner as in Step 2 of Example 2–1 except that 0.22 g (0.64 mM) of optically active 4-(2-pentyloxypropoxy)biphenyl-4'-carboxylic acid, 0.18 g (0.67 mM) of 5-butyloxy-1H,1H,5H,5H-perfluoropentanol, 5 ml of dichloromethane, 0.13 g (0.63 mM) of DCC and 0.02 g of 4-dimethylaminopyridine were used (Yield: 42.0%).

Phase transition temperature (° C.)

Cryst. ⇌(−9.2/−45) Iso.

EXAMPLE 2–3

Production of optically active 4-(2-fluorooctyloxy)-4'-(6-butyloxy-1H,1H,5H,5H-perfluoropentyloxycarbonyl)biphenyl (Ex. Comp. No. 2–124)

0.13 g of optically active 4-(2-fluorooctyloxy- 4'-(6-butyloxy-1H,1H,5H,5H-perfluoropentyloxycarbonyl)biphenyl was prepared in the same manner as in Step 2 of Example 2–1 except that 0.17 g (0.49 mM) of optically active 4-(2-fluorooctyloxy)biphenyl-4'-carboxylic acid, 0.14 g (0.52 mM) of 5-butyloxy-1H,1H,5H,5H-perfluoropentanol, 4 ml of dichloromethane, 0.10 g (0.48 mM) of DCC and 0.02 g of 4-dimethylaminopyridine were used (Yield: 44.3%).

Phase transition temperature (° C.)

Cryst. →(54.7) Iso.; Cryst. →(45.8) SmA →(48.9) Iso.

EXAMPLE 2-4

Production of optically active 2-(1-fluoroheptyl)-5-[4-(5-butyloxy-1H,1H,5H,5H-perfluoropentyloxy)phenyl]-1,3,4-thiadiazole (Ex. Comp. No. 2–118)

(Step 1)

Production of 5-butyloxy-1H,1H,5H,5H-perfluoropentyl trifluoromethanesulfonate

In a 100 ml-round bottomed flask, 1.34 g (5.0 mM) of 5-butyloxy-1H,1H,5H,5H-perfluoropentanol and 1.19 g (15.0 mM) of pyridine were placed and cooled. To the mixture, 2.82 g (10.0 mM) of trifluoromethanesulfonic anhydride was added dropwise, followed by stirring for 1 hour at room temperature. After the reaction, ice water was added to the reaction mixture and subjected to extraction with ethyl acetate. The extract was washed with 3M-hydrochloric acid and water and dried with anhydrous sodium sulfate, followed by distilling-off of the solvent to obtain 1.78 g (4.45 mM) of 5-butyloxy-1H,1H,5H,5H-perfluoropentyl trifluoromethanesulfonate (Yield: 89%).

(Step 2)

Production of optically active 2-(1-fluoroheptyl)-5-[4-(5-butyloxy-1H,1H,5H,5H-perfluoropentyloxy)phenyl]-1,3,4-thiadiazole In a 20 ml-round bottomed flask, 0.30 g (1.02 mM) of optically active 2-(1-fluoroheptyl)-5-(4-hydroxyphenyl)-1,3,4-thiadiazole and 3 ml of DMF were placed and mutually solved. To the mixture, 0.05 g (1.25 mM) of 60%-oily sodium hydride was added under stirring at room temperature. After the termination of foaming, to the resultant mixture, 0.40 g (1.00 mM) of 5-butyloxy-1H,1H,5H,5H-perfluoropentyl trifluoromethanesulfonate was added, followed by stirring for 35 minutes at 100° C. After the reaction, the reaction mixture was cooled to room temperature and poured into ice water to precipitate a crystal. The crystal was recovered by filtration, washed with water and dissolved in toluene. The solution was dried with anhydrous sodium sulfate, followed by distilling-off of the solvent to obtain a residue. The residue was purified by silica gel column chromatography (eluent: toluene/ethylacetate=50/1) and recrystallized from a toluene-methanol mixture solvent to obtain 0.14 g of optically active 2-(1-fluoroheptyl)-5-[4-(5-butyloxy-1H,1H,5H,5H-perfluoropentyloxy)phenyl]-1,3,4-thiadiazole (Yield: 25.2%).

Phase transition temperature (° C.)

Cryst. $\underset{38.2}{\overset{55.3}{\rightleftarrows}}$ Iso.

EXAMPLE 2-5

A liquid crystal composition 2-Z was prepared by mixing the following compounds including the Example Compound (Ex. Comp. No. 2-97) in the indicated proportions.

Phase transition temperature (° C.)

Cryst. $\underset{-31.7}{\overset{-9.9}{\rightleftarrows}}$ SmC* $\overset{45.1}{\rightleftarrows}$ SmA $\underset{58.6}{\overset{59.3}{\rightleftarrows}}$ Ch. $\underset{70.1}{\overset{70.2}{\rightleftarrows}}$ Iso.

EXAMPLE 2-6

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After silica beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition 2-Z prepared in Example 2-5 was heated into an isotropic liquid, and injected into the above prepared cell under vacuum and, after sealing, was gradually cooled to 25° C. at a rate of 20° C./hour to prepare a ferroelectric liquid crystal device. The cell gap was found to be about 2 microns as measured by a Berek compensator.

The ferroelectric liquid crystal device was subjected to measurement of the magnitude of spontaneous polarization

| Structural formula | wt. parts |
| --- | --- |
| $C_6H_{13}$—Py2—Ph—$OC_{12}H_{25}$ | 2.3 |
| $C_8H_{17}$—Py2—Ph—$OC_9H_{19}$ | 4.7 |
| $C_8H_{17}$—Py2—Ph—$OC_{10}H_{21}$ | 4.7 |
| $C_9H_{19}$—Py2—Ph—$OC_8H_{17}$ | 2.3 |
| $C_{10}H_{21}O$—Ph—COO—Ph—$OCH_2\overset{CH_3}{\underset{|}{C}}HC_2H_5$ | 26.0 |
| $C_6H_{13}$—Btb2—Ph—$OC_8H_{17}$ | 20.0 |
| $C_5H_{11}$—Ph—Td—Ph—$C_5H_{11}$ | 5.0 |
| $C_6H_{13}$—Ph—Td—Ph—$C_4H_9$ | 5.0 |
| $C_{11}H_{23}$—Py2—OCO—Tn—$C_4H_9$ | 6.7 |
| $C_{11}H_{23}$—Py2—Ph3F—OCO—Tn—$C_4H_9$ | 3.3 |
| $C_{10}H_{21}$—Py2—Ph—$OCH_2$*$\overset{F}{\underset{|}{C}}HC_6H_{13}$ | 10.0 |
| (Ex. Comp. No.) | |
| 2-97 $C_4H_9OCH_2(CF_2)_3CH_2$—OCO—Ph—Ph—$OCH_2\overset{CH_3}{\underset{|}{C}}HOC_5H_{11}$ | 10.0 |

The liquid crystal composition 2-Z showed the following phase transition series/

(Ps) and an optical response time (time from voltage application until the transmittance change reaches 90% of the maximum under the application of a peak-to-peak voltage Vpp of 20 V in combination with right-angle cross-nicol polarizers). The results of the measurement of response time are shown below.

|  | 10° C. | 20° C. | 30° C. |
|---|---|---|---|
| Response time (μsec) | 439 | 231 | 174 |
| Ps (nC/cm$^2$) | 12.9 | 10.6 | 7.8 |

EXAMPLE 2-7

A liquid crystal composition 2-A was prepared by mixing the following compounds in the indicated proportions.

| Structural formula | wt. parts |
|---|---|
| $C_9H_{19}$—Py2—Ph—$OC_9H_{19}$ | 6 |
| $C_{10}H_{21}$—Py2—Ph—$OC_8H_{17}$ | 6 |
| $C_8H_{17}O$—Prl—Ph—O $(CH_2)_5$*CH $(CH_3)$ $C_2H_5$ | 7 |
| $C_{11}H_{23}O$—Py2—Ph—O $(CH_2)_2$*CH $(CH_3)$ $C_2H_5$ | 14 |
| $C_{10}H_{21}$—Pr2—Ph—$C_6H_{13}$ | 8 |
| $C_6H_{13}$—Py2—Ph—Ph—$C_4H_9$ | 4 |
| $C_8H_{17}$—Ph—Pr2—Ph—$OC_5H_{11}$ | 2 |
| $C_3H_7$—Cy—COO—Ph—Pyl—$C_{12}H_{25}$ | 10 |
| $C_5H_{11}$—Cy—COO—Ph—Pyl—$C_{12}H_{25}$ | 5 |
| $C_{10}H_{21}O$—Ph—COS—Ph—$OC_8H_{17}$ | 10 |
| $C_6H_{13}$—Ph—COO—Ph—Ph—$OCH_2CH$ $(CH_3)$ $C_2H_5$ | 7 |
| $C_3H_7$—Cy—$CH_2O$—Ph—Pyl—$C_8H_{17}$ | 7 |
| $C_{10}H_{21}$—Ph—Ph—$OCH_2$—Ph—$C_7H_{15}$ | 5 |
| $C_{12}H_{25}$—Py2—Ph—$OCH_2$ *CH (F) $C_5H_{11}$ | 2 |
| $C_5H_{11}$—Cy—COO—Ph—$OCH_2$ *CH (F) $C_6H_{13}$ | 2 |
| $C_{12}H_{25}O$—Ph—Pa—COO $(CH_2)_3$*CH $(CH_3)$ $C_2H_5$ | 2 |
| $C_{12}H_{25}O$—Ph—Pa—O $(CH_2)_3$*CH $(CH_3)$ $OC_3H_7$ | 3 |

The liquid crystal composition 2-A was further mixed with the following example compounds in the indicated proportions to provide a liquid crystal composition 2-B.

A ferroelectric liquid crystal device was prepared in the same manner as in Example 2-6 except that the above liquid crystal composition 2-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 472 | 247 | 141 |

COMPARATIVE EXAMPLE 2-1

A ferroelectric liquid crystal device was prepared and subjected to measurement of response time in the same manner as in Example 2-6 except for injecting the composition 2-A prepared in Example 2-7 into a blank cell, whereby the following results were obtained.

|  | 10° C. | 25° C. | 40° C. |
|---|---|---|---|
| Response time (μsec) | 668 | 340 | 182 |

EXAMPLE 2-8

A liquid crystal composition 2-C was prepared by mixing the following Example Compounds instead of those of Example 2-7 in the indicated proportions with the liquid crystal composition 2-A.

| Ex. Comp. No. | Structural formula | wt. parts |
|---|---|---|
| 2—2 | $C_2H_5OCH_2CF_2CH_2O$—Py2—Ph—$OCH_2\underset{*}{C}HC_6H_{13}$ with F substituent | 2 |
| 2—19 | $C_9H_{19}OCH_2CF_2CH_2O$—Ph—Boal-$O(CH_2)_2\underset{*}{C}HC_8H_{17}$ with $CH_3$ substituent | 1 |
| 2—43 | $C_5H_{11}OCH_2(CF_2)_2CH_2O$—Ph—Tz1—Ph—$CH_2OCOCH_2\underset{*}{C}HC_2H_5$ with $CH_3$ substituent | 1 |
| Composition 2—A | | 96 |

| Ex. Comp. No. | Structural formula | wt. parts |
|---|---|---|
| 2—3 | $C_3H_7OCH_2(CF_2)_4CH_2-OCO-Ph-Ph-(CH_2)_{\overline{3}}\overset{*}{C}H C_2H_5$ with CH$_3$ branch | 2 |
| 2—31 | $C_2H_5O(CH_2)_2(CF_2)_2(CH_2)_2O-Ph-CH_2CH_2Ph-OCH_2\overset{*}{C}HC_8H_{17}$ with CN branch | 1 |
| 2—62 | $CH_3OCH_2(CF_2)_3CH_2O-Ph-COO-Ph-Ph-OCO-La2(5,0)$ | 1 |
| | Composition 2 — A | 96 |

A ferroelectric liquid crystal device was prepared in the same manner as in Example 2-6 except that the above liquid crystal composition 2-C was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 411 | 218 | 125 |

EXAMPLE 2-9

A liquid crystal composition 2-D was prepared by mixing the following Example Compounds instead of those of Example 2-8 in the indicated proportions with the liquid crystal composition 2-A.

| Ex. Comp. No. | Structural formula | wt. parts |
|---|---|---|
| 2—67 | $C_3H_7OCH_2(CF_2)_3CH_2O-Ph-Py1-O(CH_2)_2\overset{*}{C}HC_6H_{13}$ with CF$_3$ branch | 1 |
| 2—74 | $C_5H_{11}OCH_2(CF_2)_3CH_2O-Ph-Ep1-O(CH_2)_4\overset{*}{C}HOC_3H_7$ with CH$_3$ branch | 2 |
| 2—110 | $C_6H_{13}OCH_2(CF_2)_4CH_2O-Ph-C\equiv C-Ph-OCH_2-Lc2(6,0)$ | 1 |
| | Composition 2 — A | 96 |

A ferroelectric liquid crystal device was prepared in the same manner as in Example 2-6 except that the above liquid crystal composition 2-D was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 398 | 210 | 118 |

EXAMPLE 2-10

A liquid crystal composition 2-E was prepared by mixing the following compounds in the indicated proportions.

| Structural formula | wt. parts |
|---|---|
| $C_7H_{15}-Py2-Ph-OC_9H_{19}$ | 12 |
| $C_{11}H_{23}-Py2-Ph-OC_6H_{13}$ | 10 |
| $C_8H_{17}-Pr2-Ph-O(CH_2)_5*CH(CH_3)C_2H_5$ | 10 |
| $C_{10}H_{21}-Py2-Ph-O(CH_2)_4CH(CH_3)OCH_3$ | 3 |
| $C_8H_{17}-Py2-Ph-Ph-OC_6H_3$ | 8 |
| $C_6H_{13}O-Ph-OCO-Np-OC_9H_{19}$ | 4 |
| $C_3H_7-Cy-COO-Ph-Pyl-C_{11}H_{23}$ | 6 |
| $C_8H_{17}-Cy-COO-Ph-Pyl-C_{11}H_{23}$ | 2 |
| $C_5H_{11}-Cy-COO-Ph-Pyl-C_{11}H_{23}$ | 8 |
| $C_{10}H_{21}O-Ph-COO-Ph-OCH_2*CH(CH_3)C_2H_5$ | 15 |
| $C_4H_9-Cy-CH_2O-Ph-Pyl-C_6H_{13}$ | 7 |
| $C_5H_{11}-Cy-CH_2O-Ph-Pyl-C_6H_{13}$ | 7 |
| $C_9H_{19}O-Ph-OCH_2-Ph-Ph-C_7H_{15}$ | 4 |

-continued

| Structural formula | wt. parts |
|---|---|
| $C_6H_{13}*CH(CH_3)O-Ph-COO-Ph-Ph-OCO*CH(CH_3)OC_4H_9$ | 2 |
| $C_{12}H_{25}-Py2-Ph-OCO*CH(Cl)*CH(CH_3)C_2H_5$ | 2 |

The liquid crystal composition 2-E was further mixed with the following compounds in the proportions indicated below to provide a liquid crystal composition 2-F.

| Ex. Comp. No. | Structural Formula | wt. parts |
|---|---|---|
| 2—126 | C$_3$H$_7$OCH$_2$ (CF$_2$)$_5$CH$_2$O—Ph—Gp1—OCODp (2) | 1 |
| 2—147 | CH$_3$OCH$_2$(CF$_2$)$_6$CH$_2$O—Np—OCOC$\underset{*}{\text{C}}$(CH$_3$)C$_8$H$_{17}$ with CN substituent | 1 |
| 2—150 | C$_2$H$_5$O(CH$_2$)$_2$(CF$_2$)$_6$(CH$_2$)$_2$O—Ph—Ph—Py1—(CH$_2$)$_5\underset{*}{\text{C}}$HC$_4$H$_9$ with CH$_3$ substituent | 2 |
| Composition 2—E | | 96 |

A ferroelectric liquid crystal device was prepared in the same manner as in Example 2–6 except that the above liquid crystal composition 2-F was used, and the device was subjected to measurement of optical response time. The results are shown below.

| | 10° C. | 25° C. | 40° C. |
|---|---|---|---|
| Response time (μsec) | 481 | 238 | 135 |

COMPARATIVE EXAMPLE 2—2

A ferroelectric liquid crystal device was prepared and subjected to measurement of response time in the same manner as in Example 2–6 except for injecting the composition 2-E alone used in Examples 2–10 into a blank cell, whereby the following results were obtained.

| | 10° C. | 25° C. | 40° C. |
|---|---|---|---|
| Response time (μsec) | 784 | 373 | 197 |

EXAMPLE 2-11

A liquid crystal composition 2-G was prepared by mixing the following Example Compounds instead of those of Example 2-10 in the indicated proportions with the liquid crystal composition 2-E.

A ferroelectric liquid crystal device was prepared in the same manner as in Example 2–6 except that the above liquid crystal composition 2-G was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 468 | 235 | 136 |

EXAMPLE 2-12

A liquid crystal composition 2-H was prepared by mixing the following Example Compounds instead of those of Example 2-11 in the indicated proportions with the liquid crystal composition 2-E.

| Ex. Comp. No. | Structural formula | wt. parts |
|---|---|---|
| 2—122 | CH$_3$O(CH$_2$)$_3$(CF$_2$)$_5$(CH$_2$)$_3$O—Ph—COO—PhCOOPh—OCH$_2\underset{*}{\text{C}}$HC$_4$H$_9$ with F substituent | 1 |
| 2—177 | C$_3$H$_7$OCH$_2$(CF$_2$)$_7$CH$_2$—Ph—Pr1—O(CH$_2$)$_2\underset{*}{\text{C}}$HC$_4$H$_9$ with CF$_3$ substituent | 1 |
| 2—191 | C$_2$H$_5$OCH$_2$ (CF$_2$)$_8$CH$_2$O—Ph—Py1—OCH$_2$Lc2 (3,3) | 1 |
| Composition 2—E | | 97 |

| Ex. Comp. No. | Structural formula | wt. parts |
| --- | --- | --- |
| 2—23 | $C_{13}H_{27}O(CH_2)_2CF_2(CH_2)_2O—Ph—OCH_2—Ph—O(CH_2)_2\overset{*}{C}HC_3H_7$ with CH$_3$ branch | 1 |
| 2—72 | $C_4H_9O\ (CH_2)_3\ (CF_2)_3\ (CH_2)_3OPr2—Cy—OCH_2Tnf$ | 1 |
| 2—124 | $C_4H_9OCH_2(CF_2)_3CH_2OC(=O)—Ph—Ph—OCH_2\overset{*}{C}HC_6H_{13}$ with F branch | 1 |
| Composition 2—E | | 97 |

A ferroelectric liquid crystal device was prepared in the same manner as in Example 2-6 except that the above liquid crystal composition 2-H was used, and the device was subjected to measurement of optical response time and observation of switching states. In the device, a monodomain with a good and uniform alignment characteristic was observed. The results of the measurement are shown below.

| | 10° C. | 25° C. | 40° C. |
| --- | --- | --- | --- |
| Response time (μsec) | 523 | 263 | 156 |

EXAMPLE 2-13

A liquid crystal composition 2-I was prepared by mixing the following compounds in the indicated proportions.

| Structural formula | wt. parts |
| --- | --- |
| $C_8H_{17}$—Py2—Ph—$OC_6H_{13}$ | 10 |
| $C_8H_{17}$—Py2—Ph—$OC_9H_{19}$ | 5 |
| $C_{10}H_{21}$—Py2—Ph—$OCOC_8H_{17}$ | 7 |
| $C_{10}H_{21}$—Py2—Ph—O $(CH_2)_3CH\ (C_3)\ OC_3H_7$ | 7 |
| $C_{12}H_{25}$—Py2—Ph—O $(CH_2)_4CH\ (CH_3)\ OCH_3$ | 6 |
| $C_5H_{11}$—Py2—Ph—Ph—$C_6H_{13}$ | 5 |
| $C_7H_{15}$—Py2—Ph—Ph—$C_6H_{13}$ | 5 |
| $C_4H_9$—Cy—COO—Ph—Pyl—$C_{12}H_{25}$ | 8 |
| $C_3H_7$—Cy—COO—Ph—Pyl—$C_{10}H_{21}$ | 8 |
| $C_9H_{19}O$—Ph—COO—Ph—$OC_8H_{11}$ | 20 |
| $C_8H_{17}$—Ph—COO—Ph—Ph—$OCH_2CH\ (CH_3)\ C_2H_5$ | 5 |
| $C_8H_{17}$—Ph—OCO—Ph—Ph—*CH (CH$_3$) $OCOC_6H_{13}$ | 5 |
| $C_6H_{13}$—Ph—$OCH_2$—Ph—Ph—$C_7H_{15}$ | 6 |
| $C_{12}H_{25}$—Py2—Ph—$OCH_2$*CH (F) $C_6H_{13}$ | 3 |

The liquid crystal composition 2-I was further mixed with the following compounds in the proportions indicated below to provide a liquid crystal composition 2-J.

| Ex. Comp. No. | Structural formula | wt. parts |
| --- | --- | --- |
| 2—6 | $C_4H_9OCH_2CF_2CH_2O—Ph—Btb1—OCH_2\overset{*}{C}HC_8H_{17}$ with F branch | 1 |
| 2—32 | $C_2H_5O(CH_2)_6(CF_2)_2(CH_2)_6O—Ph—Ph3F—OCH_2La2\ (6,0)$ | 1 |
| 2—46 | $C_6H_{13}OCH_2(CF_2)_2CH_2O—Ph—Pd—O\overset{*}{C}HC_9H_{19}$ with CH$_3$ branch | 2 |
| Composition 2—I | | 96 |

A ferroelectric liquid crystal device was prepared in the same manner as in Example 2-6 except that the above liquid crystal composition 2-J was used, and the device was subjected to measurement of optical response time and observation of switching states. In the device, a monodomain with a good and uniform alignment characteristic was observed. The results of the measurement are shown below.

| | 10° C. | 25° C. | 40° C. |
| --- | --- | --- | --- |
| Response time (μsec) | 386 | 195 | 103 |

COMPARATIVE EXAMPLE 2-3

A ferroelectric liquid crystal device was prepared and subjected to measurement of response time in the same manner as in Example 2-6 except for injecting the composition 2-I alone used in Examples 2-13 into the cell, whereby the following results were obtained.

| | 10° C. | 25° C. | 40° C. |
| --- | --- | --- | --- |
| Response time (μsec) | 653 | 317 | 159 |

EXAMPLE 2-14

A liquid crystal composition 2-K was prepared by mixing the following Example Compounds instead of those of Example 1–13 in the indicated proportions with the liquid crystal composition 2-I.

| Ex. Comp. No. | Structural formula | wt. parts |
|---|---|---|
| 2–86 | $C_{10}H_{21}OCH_2(CF_2)_3CH_2O-Ph-Td-Ph-O(CH_2)_5\overset{*}{C}HC_9H_{19}$ with $CH_3$ branch | 1 |
| 2–91 | $CH_3O(CH_2)_4(CF_2)_4(CH_2)_4O-Ph-Id2-CH_2\overset{*}{C}HC_6H_{13}$ with $CH_3$ branch | 1 |
| 2–179 | $C_4H_9OCH_2(CF_2)_7CH_2O-Pr2-Ph-OCH_2-Cy-OCH_2Lal\ (5,2)$ | 1 |
| | Composition 2–I | 97 |

A ferroelectric liquid crystal device was prepared in the same manner as in Example 2–6 except that the above liquid crystal composition 2-K was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 412 | 206 | 112 |

EXAMPLE 2–15

A liquid crystal composition 2-L was prepared by mixing the following Example Compounds instead of those of Example 2–14 in the indicated proportions with the liquid crystal composition 2-I.

| Ex. Comp. No. | Structural formula | wt. parts |
|---|---|---|
| 2–98 | $C_3H_7O(CH_2)_2(CF_2)_4(CH_2)_2O-Ph-Dx2-Ph-OCOPla$ | 1 |
| 2–133 | $C_4H_9OCH_2(CF_2)_5CH_2O-Ph-Bob1-(CH_2)_2\overset{*}{C}HC_{12}H_{25}$ with $F$ branch | 1 |
| 2–181 | $C_5H_{11}OCH_2(CF_2)_7CH_2O-Ph-Pa-O(CH_2)_4\overset{*}{C}HC_8H_{17}$ with $CF_3$ branch | 1 |
| | Composition 2–I | 97 |

A ferroelectric liquid crystal device was prepared in the same manner as in Example 2–6 except that the above liquid crystal composition 2-L was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 445 | 220 | 116 |

As apparent from the above Example 2–7 to 2–15, the ferroelectric liquid crystal device including the liquid crystal compositions 2-B, 2-C, 2-D, 2-F, 2-G, 2-H, 2-J, 2-K, and 2-L i.e., compositions containing a mesomorphic compound of the formula (I) according to the present invention, provided improved operation characteristic at a lower temperature, high speed responsiveness and a decreased temperature dependence of response speed.

EXAMPLE 2–16

A blank cell was prepared in the same manner as in Example 2–6 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition 2-D used in Example 2–9. The liquid crystal device was subjected to measurement of response time in the same manner as in Example 2–6. The results are shown below.

| | 10° C. | 25° C. | 40° C. |
|---|---|---|---|
| Response time (μsec) | 396 | 208 | 120 |

EXAMPLE 2–17

A blank cell was prepared in the same manner as in Example 2–6 except for omitting the SiO$_2$ layer to form an alignment control layer composed of the polyimide resin layer alone on each electrode plate. A ferroelectric liquid crystal device was prepared by filling such a blank cell with liquid crystal composition 2-D used in Example 2-9. The liquid crystal device was subjected to measurement of response time in the same manner as in Example 2-6. The results are shown below.

|  | 10° C. | 25° C. | 40° C. |
| --- | --- | --- | --- |
| Response time (μsec) | 381 | 202 | 115 |

As is apparent from the above Example 2-16 and 2-17, also in the case of a different device structure, the device containing the ferroelectric liquid crystal composition 2-D according to the present invention provided an improved low-temperature operation characteristic and a decreased temperature dependence of response speed similarly as in Examples 2-9.

EXAMPLE 2-18

A liquid crystal composition 2-M was prepared by mixing the following compounds in the indicated proportions.

| Structural formula | wt. parts |
| --- | --- |
| $C_6H_{13}$—Py2—Ph—O $(CH_2)_4C_3F_7$ | 5 |
| $C_{11}H_{23}$—Py2—Ph—$OCH_2C_4F_9$ | 10 |
| $C_8H_{17}O$—Prl—Ph—O $(CH_2)_5CH\ (CH_3)\ C_2H_5$ | 5 |
| $C_{10}H_{21}$—Py2—Ph—O $(CH_2)_4CH\ (CH_3)\ OCH_3$ | 10 |
| $C_6H_{13}$—Py2—Ph—Ph—$C_8H_{17}$ | 7 |
| $C_8H_{17}$—Py2—Ph—$OC_6H_{13}$ | 15 |
| $C_5H_{11}$—Cy—COO—Ph—Pyl—$C_{12}H_{25}$ | 5 |
| $C_4H_9$—Cy—COO—Ph—Pyl—$C_{11}H_{23}$ | 5 |
| $C_3H_7$—Cy—COO—Ph—Pyl—$C_{11}H_{23}$ | 5 |
| $C_{12}H_{25}O$—Ph—Pa—CO $(CH_2)_3$*CH $(CH_3)\ C_2H_5$ | 2 |
| $C_{10}H_{21}$—Py2—Ph—$OCH_2$*CH (F) $C_2H_5$ | 5 |
| $C_6H_{13}$—Cy—COO—Ph—$OCH_2$*CH (F) $C_6H_{13}$ | 2 |
| $C_8H_{17}$—Ph—OCO—Ph—Ph—CH $(CH_3)\ OCOC_6H_{13}$ | 6 |
| $C_8H_{17}$—Py2—Ph—OCO—Ph—F | 2 |
| $C_7H_{15}O$—Ph—Tzl—Ph—$C_5H_{11}$ | 3 |
| $C_6H_{13}O$—Btb2—Ph—OCO $(CH_2)_6C_2F_5$ | 3 |
| $C_8H_{17}O$—Ph—COS—Ph—$OCH_2C_3F_7$ | 10 |

The liquid crystal composition 2-M was further mixed with the following example compounds in the indicated proportions to provide a liquid crystal composition 2-N.

| Ex. Comp. No. | Structural formula | wt. parts |
| --- | --- | --- |
| 2—16 | $C_4H_9OCH_2(CF_2)_3CH_2O$—Ph—Ep1—$OCOCHCHC_2H_5$ with Cl and $CH_3$ substituents (*,*) | 1 |
| 2—21 | $C_{11}H_{23}OCH_2CF_2CH_2O$—Py2—Cm2—$(CH_2)_2CHC_6H_{13}$ with $CF_3$ substituent (*) | 1 |
| | Composition 2—M | 98 |

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.0%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 120 Å-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 1.5 microns as measured by a Berek compensator.

Then, the liquid crystal composition 2-N prepared above was heated into an isotropic liquid, and injected into the above prepared cell under vacuum and, after sealing, was gradually cooled to 25° C. at a rate of 20° C./hour to prepare a ferroelectric liquid crystal device.

The ferroelectric liquid crystal device was subjected to measurement of a contrast ratio at 30° C. when the device was driven by applying a driving voltage waveform shown in FIGS. 5A and 5B (bias ratio=1/3), whereby a contrast ratio at 30° C. of 15.6 was obtained.

COMPARATIVE EXAMPLE 2-4

A ferroelectric liquid crystal device was prepared and subjected to measurement of a contrast ratio in the same manner as in Example 2-18 except for injecting the composition 2-M alone used in Examples 2-18 into a blank cell, whereby a contrast ratio of 8.1 was obtained.

EXAMPLE 2-19

A liquid crystal composition 2-O was prepared by mixing the following Example Compounds instead of those of Example 2-18 in the indicated proportions with the liquid crystal composition 2-M.

| Ex. Comp. No. | Structural formula | wt. parts |
| --- | --- | --- |
| 2—45 | $C_5H_{11}O(CH_2)_3(CF_2)_2(CH_2)_4O$—Ph—Ph—Pyl—O—Lc2 (3,3) | 1 |
| 2—51 | $C_7H_{15}O(CH_2)_2(CF_2)_2(CH_2)_2$—C≡C—Ph—Py1—$OCOCHC_6H_{17}$<br>$\overset{\|}{CF_3}$ * | 1 |
| 2—80 | $C_7H_{15}OCH_2(CF_2)_3CH_2O$—Pr2—Ph—OCO—Tn—$CH_2CH(CH_3)C_2H_5$<br>$\overset{\|}{CN}$ * | 1 |
| | Composition 2—M | 97 |

A ferroelectric liquid crystal device was prepared in the same manner as in Example 2–18 except that the above liquid crystal composition 2-O was used, and the device was subjected to measurement of a contrast ratio, whereby a contrast ratio of 19.3 was obtained.

EXAMPLE 2-20

A liquid crystal composition 2-P was prepared by mixing the following Example Compounds instead of those of Example 2–19 in the indicated proportions with the liquid crystal composition 2-M.

A ferroelectric liquid crystal device was prepared in the same manner as in Example 2–18 except that the above liquid crystal composition 2-Q was used, and the device was subjected to measurement of a contrast ratio, whereby a contrast ratio of 18.5 was obtained.

As apparent from the above Example 2–18 to 2–21, the ferroelectric liquid crystal device including the liquid crystal compositions 2-N, 2-O, 2-P and 2-Q, i.e., compositions containing a mesomorphic compound of the formula (I) according to the present invention, provided improved a higher contrast ratio when driven.

| Ex. Comp. No. | Structural formula | wt. parts |
| --- | --- | --- |
| 2—85 | $C_9H_{17}OCH_2(CF_2)_3CH_2O$—Ph—Ph23F—$OCH_2CHC_2H_5$<br>$\overset{\|}{F}$ * | 1 |
| 2—93 | $C_2H_5OCH_2(CF_2)_4CH_2O$—Ph—Gp1—$OCH_2$—La2 (8,0) | 1 |
| 2—105 | $C_5H_{11}OCH_2(CF_2)_4CH_2O$—Ph—Ph—Cy—OCO—Thf | 1 |
| | Composition 2—M | 97 |

A ferroelectric liquid crystal device was prepared in the same manner as in Example 2–18 except that the above liquid crystal composition 2-P was used, and the device was subjected to measurement of a contrast ratio, whereby a contrast ratio of 20.8 was obtained.

EXAMPLE 2-21

A liquid crystal composition 2-Q was prepared by mixing the following Example Compounds instead of those of Example 2–20 in the indicated proportions with the liquid crystal composition 2-M.

EXAMPLE 2-22

A blank cell was prepared in the same manner as in Example 2–18 by using a 2% aqueous solution of polyvinyl alcohol resin (PVA-117, available from Kuraray K.K.) instead of the 1.0%-solution of polyimide resin precursor in dimethylacetoamide on each electrode plate. A ferroelectric liquid crystal device was prepared by filling the blank cell with the liquid crystal composition 2-P used in Example 2–20. The liquid crystal device was subjected to measurement of a contrast ratio in the same manner as in Examples 2–18, whereby a contrast ratio of 21.3 was obtained.

| Ex. Comp. No. | Structural formula | wt. parts |
| --- | --- | --- |
| 2—137 | $C_6H_{11}OCH_2(CF_2)_5CH_2O$—Py2—Id2—$(CH_2)_3CHC_6H_{13}$<br>$\overset{\|}{F}$ * | 1 |
| 2—163 | $C_6H_{13}OCH_2(CF_2)_6CH_2O$—Pr2—Np—$O(CH_2)_6CHC_6H_{13}$<br>$\overset{\|}{CF_3}$ * | 1 |
| 2—228 | $C_4H_9OCH_2(CF_2)_3CH_2O$—Ph—Pyl—$OCH_2$—Lc1 (0,0) | 1 |
| | Composition 2—M | 97 |

EXAMPLE 2-23

A blank cell was prepared in the same manner as in Example 2-18 except for omitting the SiO$_2$ layer to form an alignment control layer composed of the polyimide resin layer alone on each electrode plate. A ferroelectric liquid crystal device was prepared by filling such a blank cell with liquid crystal composition 2-P used in Example 2-20. The liquid crystal device was subjected to measurement of response time in the same manner as in Example 2-18, whereby a contrast ratio of 17.7 was obtained.

EXAMPLE 2-24

A blank cell was prepared in the same manner as in Example 2-18 except that a 1.0%-solution of polyamide acid (LQ-1802, available from Hitachi Kasei K.K.) in NMP (N-methylpyrrolidone) was used instead of the 1.0%-solution of polyimide resin precursor in dimethylacetoamide on each electrode plate and that the hot curing treatment thereof was effected at 270° C. for 1 hour. A ferroelectric liquid crystal device was prepared by filling the blank cell with the liquid crystal composition 2-P used in Example 2-20. The liquid crystal device was subjected to measurement of contrast ratio in the same manner as in Example 2-18, whereby a contrast ratio of 33.2 was obtained.

As is apparent from the above Example 2-22, 2-23 and 2-24, also in the case of a different device structure, the device containing the ferroelectric liquid crystal composition 2-P according to the present invention provided a higher contrast ratio similarly as in Example 2-20.

Further, when a driving voltage waveform different from that used in Example 2-18, a liquid crystal device using the liquid crystal composition according to the present invention provided a higher contrast ratio compared with a liquid crystal device using a liquid crystal composition containing no mesomorphic compound of the formula (I) of the present invention.

As described hereinabove, according to the present invention, by utilizing a ferroelectricity exhibited by a liquid crystal composition containing at least one mesomorphic compound of the formula (I), there is provided a liquid crystal device providing improved characteristics such as a good alignment characteristic, a good switching property, high-speed responsiveness, a decreased temperature-dependence of response speed, and a high contrast ratio.

In addition, when the liquid crystal device is used as a display device in combination with a light source, drive circuit, etc., a liquid crystal apparatus, such as a liquid crystal display apparatus, providing good display characteristics can be realized.

What is claimed is:

1. A liquid crystal composition, said liquid crystal composition having a chiral smectic phase and comprising at least two different compounds, at least one of which is a mesomorphic compound represented by the following formula (I):

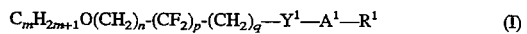

$$C_mH_{2m+1}O(CH_2)_n\text{-}(CF_2)_p\text{-}(CH_2)_q\text{-}Y^1\text{-}A^1\text{-}R^1 \qquad (I)$$

wherein R$^1$ denotes H, halogen, CN, or a linear or branched alkyl group having 1-30 carbon atoms or cyclized alkyl group having at most 6 carbon atoms, said alkyl group being capable of including at least one —CH$_2$— group which can be replaced with —O—, —S—, —CO—, —CH(Cl)—, —CH(CN)—, —CCH$_3$ (CN)—, —CH=CH— or —C≡C— provided that heteroatoms are not adjacent to each other and capable of including at least one H which can be replaced with F;

m, n, p and q independently denote an integer of 1-16 provided that m+n+p+q≦19;

Y$^1$ denotes a single bond, —O—, —CO—, —COO—, —OCO—, —CH=CH— or —C≡C—;

A$^1$ denotes —A$^2$—, —A$^2$—X$^1$—A$^3$— or —A$^2$—X$^1$—A$^3$—X$^2$—A$^4$ in which A$^2$, A$^3$ and A$^4$ independently denote a divalent cyclic group selected from 1,4-phenylene capable of having one or two substituents comprising F, Cl, Br, CH$_3$, CF$_3$ or CN; pyridine-2,5-diyl; pyrimidine-2,5-diyl; pyrazine-2,5-diyl; pyridazine-3,6-diyl; 1,4-cyclohexylene; 1,3-dioxane-2,5-diyl; 1,3-dithiane-2,5-diyl; thiophene-2,5-diyl; thiazole-2,5-diyl; thiadiazole-2,5-diyl; benzoxazole-2,5-diyl; benzoxazole-2,6-diyl; benzothiazole-2,5-diyl; benzothiazole-2,6-diyl; quinoxaline-2,6-diyl; quinoline-2,6-diyl; 2,6-naphthylene; indan-2,5-diyl; 2-alkylindan-2,5-diyl having a linear or branched alkyl group having 1-18 carbon atoms; indanone-2,6-diyl; 2-alkylindanone-2,6-diyl having a linear or branched alkyl group having 1-18 carbon atoms; coumaran-2,5-diyl; and 2-alkylcoumaran-2,5-diyl having a linear or branched alkyl group having 1-18 carbon atoms; and X$^1$ and X$^2$ independently denote a single bond —COO—, —OCO—, —CH$_2$O—, —OCH$_2$—, —CH$_2$CH$_2$—, —CH=CH— or —C≡C.

2. A liquid crystal composition according to claim 1, which comprises 1-80 wt. % of a mesomorphic compound of the formula (I).

3. A liquid crystal composition according to claim 1, which comprises 1-60 wt. % of a mesomorphic compound of the formula (I).

4. A liquid crystal composition according to claim 1, which comprises 1-40 wt. % of a mesomorphic compound of the formula (I).

5. A liquid crystal device, comprising a pair of substrates and a liquid crystal composition according to claim 1 disposed between the substrates.

6. A device according to claim 5, which further comprises an alignment control layer.

7. A device according to claim 6, wherein the alignment control layer has been subjected to uniaxial alignment treatment.

8. A device according to claim 5, wherein the liquid crystal composition is disposed in a thickness suppressing formation of a helical structure of liquid crystal molecules between the substrates.

9. A liquid crystal apparatus comprising a liquid crystal device according to claim 5.

10. An apparatus according to claim 9, wherein the liquid crystal device is used as a display device.

11. An apparatus according to claim 9, which further comprises a drive circuit for the liquid crystal device.

12. An apparatus according to claim 10, which further comprises a light source.

13. A display method, comprising:

providing a liquid crystal composition according to claim 1; and controlling the alignment direction of liquid crystal molecules to effect display.

* * * * *

UNITED STATES PATENT AND TRADEMARK OFFICE
CERTIFICATE OF CORRECTION

PATENT NO. : 5,653,913

DATED : August 5, 1997

INVENTOR(S): SHINICHI NAKAMURA ET AL.

It is certified that error appears in the above-identified patent and that said Letters Patent is hereby corrected as shown below:

<u>ON COVER PAGE, AT [73]</u>
  Line 1, "Kaishai" should read --Kaisha--.

<u>COLUMN 1</u>
  Line 46, "in" should read --in synchronism--;
  Line 48, "in" should read --in a-- and "electric" should read --electric field--;
  Line 52, "which" should read --which regions--;
  Line 53, "selected" should read --selected points--.

<u>COLUMN 2</u>
  Line 24, "optic" should read --optical--;
  Line 31, "electric" should read --electric field--;
  Line 32, "an" should read --an electric--;
  Line 33, "In" should read --In addition--;
  Line 65, "a" should be deleted.

<u>COLUMN 3</u>
  Line 9, "it" should read --if it--;
  Line 42, "with" should read --with a--.

<u>COLUMN 4</u>
  Line 2, "an" should read --a--.

UNITED STATES PATENT AND TRADEMARK OFFICE
CERTIFICATE OF CORRECTION

PATENT NO. : 5,653,913

DATED : August 5, 1997

INVENTOR(S): SHINICHI NAKAMURA ET AL.

It is certified that error appears in the above-identified patent and that said Letters Patent is hereby corrected as shown below:

COLUMN 5
Line 30, "taking" should read --taken--;
Line 45, "is" should read --shows--;
Line 48, "show" should read --shown--;
Line 51, "liquid" should read --a liquid--;
Line 67, "group" (second occurrence) should read --groups--.

COLUMN 6
Line 11, "H" should read --one H--;
Line 19, "—C≡—" should read -- —C≡C— --;
Line 53, "compound:" should read --compounds--.

COLUMN 7
Line 60, change "the the" to --the following mesomorphic compounds (Ibaa) to (Icea) of the--.

COLUMN 8
Line 20, "or two" should read --one or two--.

COLUMN 10
Line 42, "assumes" should read --assuming--.

COLUMN 14
Line 1-49, "$OC_{11}H_{13}$" should read --$OC_{11}H_{23}$--;
Line 1-66, "$C_8H_{17}$" should read --$C_9H_{19}$--.

UNITED STATES PATENT AND TRADEMARK OFFICE
CERTIFICATE OF CORRECTION

PATENT NO. : 5,653,913

DATED : August 5, 1997

INVENTOR(S): SHINICHI NAKAMURA ET AL.

It is certified that error appears in the above-identified patent and that said Letters Patent is hereby corrected as shown below:

COLUMN 16
 Line 1-96, "$OCH_2C_8H_{17}$" should read $OCH_2C_8F_{17}$--;
 Line 1-111, "$OC_4H_{19}$" should read --$OC_4H_9$--;
 Line 1-141, "$OC_8H_{17}$" should read --$C_8H_{17}$--.

COLUMN 20
 Line 1-228, "$CH_2OCH_2$" should read -- $CH_2OCH_3$--.

COLUMN 28
 Line 2-101, "--La(1,1)" should read --La2(1,1)--.

COLUMN 34
 Line 2-146, "$O(CH_2)_5$" should read --$O(CH_2)_8$--;
 Line 2-147, "$C_6H_{17}$" should read --$C_8H_{17}$--.

COLUMN 40
 Line 2-230, "$CHOCOC_6H_{13}$" should read --$CHOCOC_6F_{13}$--.

COLUMN 42
 Table, "$Y_1'$" should read --$Y_7'$--.

COLUMN 45
 Line 4, "with," should read --with--.

UNITED STATES PATENT AND TRADEMARK OFFICE
CERTIFICATE OF CORRECTION

PATENT NO. : 5,653,913

DATED : August 5, 1997

INVENTOR(S): SHINICHI NAKAMURA ET AL.

It is certified that error appears in the above-identified patent and that said Letters Patent is hereby corrected as shown below:

COLUMN 46
  Line 48, "⅓¼" should read --⅓-¼--.

COLUMN 47
  Line 51, "dicyclohexy-" should read --dicyclohexyl--;
  Line 52, "lcarbodiimide" should read --carbodiimide--;
  Line 60, "1H," should read --1H,1H,--.

COLUMN 50
  Line 31, "second" should read --seconds--.

COLUMN 57
  Line 35, "Example" should read --Examples--;
  Line 41, "Examples" should read --Example--.

COLUMN 58
  Line 7, "Compositoin" should read --Composition--.

COLUMN 59
  Line 1-46, "(CF$_2$)$_2$O—" should read --(CF$_2$)$_2$CH$_2$O—--;
  Line 62, "improved a" should read --an improved--.

COLUMN 60
  Line 16, "Examples" should read --Example--.

COLUMN 62
  Line 33, "fluorooctyloxy—" should read --fluorooctyloxy)—--.

UNITED STATES PATENT AND TRADEMARK OFFICE
CERTIFICATE OF CORRECTION

PATENT NO. : 5,653,913

DATED : August 5, 1997

INVENTOR(S): SHINICHI NAKAMURA ET AL.

It is certified that error appears in the above-identified patent and that said Letters Patent is hereby corrected as shown below:

COLUMN 63
  Ex 2-5, "—Py2" should read -- Py2—Ph---;
  Line 67, "series/" should read --series.--.

COLUMN 64
  Line 15, "second" should read --seconds--.

COLUMN 69
  Ex 2-147, "—OCOCC" should read ---OCOC--;
  Line 32, "Examples" should read --Example--.

COLUMN 72
  Line 56, "Examples" should read --Example--.

COLUMN 76
  Line 2, "second" should read --seconds--.

COLUMN 77
  Ex 2-20, "$C_9H_{17}$" should read --$C_9H_{19}$--;
  Ex 2-21, "$C_6H_{11}$" should read --$C_5H_{11}$--.

COLUMN 78
  Line 21, "Example" should read --Examples--;
  Line 25, "improved a" should read --an improved--;
  Line 49, "Examples" should read --Example--.

UNITED STATES PATENT AND TRADEMARK OFFICE
CERTIFICATE OF CORRECTION

PATENT NO. : 5,653,913

DATED       : August 5, 1997

INVENTOR(S): SHINICHI NAKAMURA ET AL.

It is certified that error appears in the above-identified patent and that said Letters Patent is hereby corrected as shown below:

<u>COLUMN 79</u>
Line 26, "Example" should read --Examples--.

<u>COLUMN 80</u>
Line 27, "$X^l$" should read --$X^1$--.

Signed and Sealed this

Thirtieth Day of June, 1998

Attest:

BRUCE LEHMAN

Attesting Officer

Commissioner of Patents and Trademarks